US007927835B2

(12) United States Patent
Larsen et al.

(10) Patent No.: US 7,927,835 B2
(45) Date of Patent: *Apr. 19, 2011

(54) NUCLEIC ACIDS ENCODING P-SELECTIN LIGAND FUSION PROTEINS

(75) Inventors: Glenn R. Larsen, Sudbury, MA (US); Dianne S. Sako, Boston, MA (US); Xiao-Jia Chang, Newtown Centre, MA (US); Geertruida M. Veldman, Sudbury, MA (US); Dale Cumming, Acton, MA (US); Ravindra Kumar, Belmont, MA (US); Gray Shaw, Cambridge, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/167,680

(22) Filed: Jul. 3, 2008

(65) Prior Publication Data
US 2008/0280327 A1 Nov. 13, 2008

Related U.S. Application Data

(60) Division of application No. 09/935,144, filed on Aug. 21, 2001, now Pat. No. 7,563,760, which is a continuation of application No. 08/713,556, filed on Aug. 30, 1996, now Pat. No. 6,277,975, which is a continuation-in-part of application No. 08/428,734, filed on Apr. 25, 1995, now Pat. No. 5,843,707, which is a continuation-in-part of application No. 08/316,305, filed on Sep. 30, 1994, now abandoned, which is a continuation-in-part of application No. 08/235,398, filed on Apr. 28, 1994, now abandoned, which is a continuation-in-part of application No. 08/112,608, filed on Aug. 26, 1993, now abandoned, which is a continuation-in-part of application No. 07/965,662, filed on Oct. 23, 1992, now abandoned.

(30) Foreign Application Priority Data

Oct. 22, 1993 (WO) .................. PCT/US93/10168

(51) Int. Cl.
*C07H 21/04* (2006.01)
*C12N 15/00* (2006.01)
*C12N 15/11* (2006.01)

(52) U.S. Cl. .................. 435/69.7; 536/23.1; 536/23.4; 536/23.5; 536/24.1

(58) Field of Classification Search .................. None
See application file for complete search history.

(56) References Cited

U.S. PATENT DOCUMENTS

| 4,657,853 | A | 4/1987 | Freytag et al. |
| 4,675,285 | A | 6/1987 | Clark et al. |
| 4,978,611 | A | 12/1990 | Hosoda et al. |
| 5,198,424 | A | 3/1993 | McEver |
| 5,304,640 | A | 4/1994 | Lasky et al. |
| 5,318,890 | A | 6/1994 | Rosen et al. |
| 5,360,733 | A | 11/1994 | Fukuda et al. |
| 5,378,464 | A | 1/1995 | McEver |
| 5,464,778 | A | 11/1995 | Cummings et al. |
| 5,614,615 | A | 3/1997 | Wong |
| 5,827,817 | A | 10/1998 | Larsen et al. |
| 5,840,679 | A | 11/1998 | Larsen et al. |
| 5,843,707 | A | 12/1998 | Larsen et al. |
| 6,277,975 | B1 | 8/2001 | Larsen et al. |

FOREIGN PATENT DOCUMENTS

| EP | 0 480 408 A1 | 4/1992 |
| WO | WO 90/01546 | 2/1990 |
| WO | WO 91/00868 | 1/1991 |
| WO | WO 91/06632 | 5/1991 |
| WO | WO 92/01718 | 2/1992 |
| WO | WO 92/09698 | 6/1992 |
| WO | WO 92/16612 | 10/1992 |
| WO | WO 92/19735 | 11/1992 |
| WO | WO 93/03052 | 2/1993 |
| WO | WO 93/04199 | 3/1993 |
| WO | WO 93/09250 | 5/1993 |
| WO | WO 93/13220 | 7/1993 |
| WO | WO 93/15228 | 8/1993 |
| WO | WO 94/07917 | 4/1994 |
| WO | WO 94/10309 | 5/1994 |
| WO | WO 94/11498 | 5/1994 |
| WO | WO 95/30001 | 11/1995 |
| WO | WO 97/06176 | 2/1997 |
| WO | WO 98/08949 | 3/1998 |

OTHER PUBLICATIONS

Pouyani et al., Cell, 1995, vol. 83:333-343.*
Peppel et al., J. Exp. Med., Dec. 1991, vol. 174(6):1483-1489.*
Eck & Wilson, 1996, in: Goodman & Gilman's The Pharmacological Basis of Therapeutics, Ninth Edition, McGraw-Hill, New York.*
Supplementary Partial European Search Report, mailed Oct. 17, 2001 for EP 99 96 4950.
International Search Report, mailed Dec. 5, 1995 for PCT/US95/04968.
International Search Report, mailed Feb. 7, 1995 for PCT/US93/10168.
International Search Report, mailed Aug. 1, 1996 for PCT/US95/04968.

(Continued)

*Primary Examiner* — Elizabeth C. Kemmerer
*Assistant Examiner* — Xiaozhen Xie
(74) *Attorney, Agent, or Firm* — Finnegan, Henderson, Farabow, Garrett & Dunner, L.L.P.

(57) ABSTRACT

A novel P-selectin ligand glycoprotein is disclosed, comprising the amino acid sequence set forth in SEQ ID NO:2 or by the amino acid sequence set forth in SEQ ID NO:4. DNA sequences encoding the P-selectin ligand protein are also disclosed, along with vectors, host cells, and methods of making the P-selectin ligand protein. Pharmaceutical compositions containing the P-selectin ligand protein and methods of treating inflammatory disease states characterized by P-selectin- and E-selectin-mediated intercellular adhesion are also disclosed.

16 Claims, 30 Drawing Sheets

OTHER PUBLICATIONS

International Search Report, mailed Mar. 11, 1991 for PCT/US90/06101.
Aruffo et al., "CD62/P-Selectin Recognition of Myeloid and Tumor Cell Sulfatides", *Cell*, vol. 67:35-44 (1991).
Bierhuizen et al., "Expression Cloning of cDNA Encoding UDP-Glc:Galbetal-3-GalNAc-R (GlcNAc to GalNAc) betal-6GlcNAc-R Transferase by Gene Transfer into CHO Cells Expressing Polymoma Large Tumor Antigen" *PNAS*, vol. 89:9326-9330 (Oct. 1992).
Campbell et al., "Regulatory Mutations in CHO Cells Induce Expression of the Mouse Embryonic Antigen SSEA-1" *Cell.*, vol. 35:303-309 (Nov. 1983).
Davenpeck et al., "Activation of Human Leukocytes Reduces Surface P-Selectin Glycoprotein Ligand-1 (PSGL-1, CD162) and Adhesion to P-Selectin In Vitro" *J. Immunol.*, vol. 165:2764-2772 (2000).
Goochee et al., "The Oligosaccharides of Glycoproteins Factors Affecting Their Synthesis and Their Influence on Glycoprotein Properties" *Frontiers in Bioprocessing II, Proc. of Frontiers in Biochemistry II*, pp. 198-240, Boulder, Colorado, (Jun. 17-21, 1990).
Johnston et al., "Cloning of GMP-140, a Granule Membrane Protein of Platelets and Endothelium: Sequence Similarity to Proteins Involved in Cell Adhesion and Inflammation" *Cell*, vol. 56:1033-1044 (Mar. 24, 1989).
Kruger et al., "Activated T Lymphocytes Bind In Situ to Stromal Tissue of Colon Carcinoma but lack Adhesion to Tumor Cells" *Eur. J. Immunol.*, 31:138-145 (2001).
Larkin et al., "Spectrum of Sialylated and Nonsialylated Fuco-oligosaccharides Bound by the Endothelial-Leukocyte Adhesion Molecule E-selectin" *J. Biol. Chem.*, vol. 267:13661-1368 (1992).
Larsen et al., "P-Selectin and E-Selectin" *J. Biol. Chem.*, vol. 267, No. 16:11104-11110 (Jun. 5, 1992).
Li et al., "Visualization of P-Selectin Glycoprotein Ligand-1 as a Highly Extended Molecule and Mapping of Protein Epitopes for Monoclonal Antibodies" *J. Biol. Chem.*, vol. 271, No. 11:6342-6348 (Mar. 15, 1996).
Maemura et al., "Poly-N-Acetyllactosaminyl O-Glycans Attached to Leukosialin" *J. Biol. Chem.*, vol. 267, No. 34:24379-24386 (1992).
Manjunath et al., "A Transgenic Mouse Model to Analyze CD8+ Effector T Cell Differentiation in vivo" *PNAS*, vol. 96, No. 24:13932-13937 (Nov. 23, 1999).
Moore et al., "Identification of a Specific Glycoprotein Ligand for P-Selectin (CD62 on Myeloid Cells" *J. Cell Biology*, vol. 118, No. 2:445-456 (Jul. 1992).
Moore et al., "The P-Selectin Glycoprotein Ligand from Human Neutrophils Displays Sialylated, Fucosylated, O-Linked Poly-N-Acetyllactosamine" *J. Biol. Chem.*, vol. 269, No. 37:23318-23327 (Sep. 16, 1994).
Mulligan et al., "Protective Effects of Oligosaccaharides in P-Selectin-Dependent Lung Injury" *Nature*, vol. 364:149-151 (Jul. 8, 1993).
Mulligan et al., "Protective Effects of Sialylated Oligosaccharides in Immune Complex-Induced Acute Lung Injury" *J. Exp. Med.*, vol. 178:623-631 (Aug. 1993).
Mulligan et al., "Neutrophil-dependent Acute Lung Injury" *J. Clin. Invest.*, vol. 90:1600-1607 (Oct. 1992).
Norgard et al., "Characterization of a Specific Ligand for P-Selectin on Myeloid Cells" *J. Biol. Chem.*, vol. 268, No. 17:12674-12774 (Jun. 15, 1993).
Paul, W.E., "Peripheral Circulation of T-Lymphocytes" *Fundamental Immunology*, Fourth Edition, Chapter 11: 393-397. (1999) .
Phillips et al., "ELAM-1 Mediates Cell Adhesion by Recognition of a Carbohydrate Ligand, Sialyl-Le$^x$", *Science*, vol. 250:1130-2 (Nov. 23, 1990).
Picker et al., The Neutrophil Selectin LECAM-1 Presents Carbohydrate Ligands to the Vascular Selectins ELAM-1 and GMP-140, *Cell*, vol. 66:921-933 (Sep. 6, 1991).
Polley et al., "CD62 and Endothelial Cell-Leukocyte Adhesion Molecule 1 (ELAM-1) Recognize the Same Carbohydrates Ligand, Sialyl-Lewis x", *PNAS*, vol. 88:6224-6228 (Jul. 1991).
Ridger et al., "L- and P-selectins collaborate to support leukocyte rolling in vivo when high-affinity P-selectin-P-selectin glycoprotein ligand-1 interaction is inhibited" *Am J Pathol.* 166: 945-52 (2005).
Sako, D., "Expression Cloning of a Functional Glycoprotein Ligand for P-Selectin" *Cell*, vol. 75:1179-1186 (Dec. 17, 1993).

Steininger et al., "The Glycoprotease of *Pasteurellla Haemolytica* A1 Eliminates Binding of Myeloid Cells to P-Selectin but not to E-Selectin" *Biochem. & Biophys. Res. Comm.*, vol. 188, No. 2:760-766 (Oct. 30, 1992).
Takada et al., "The Cytokine-Adhesion Molecule Cascade in Ischemia/Reperfusion Injury of the Rat Kidney" *J. Clin. Invest.*, vol. 99, No. 11:2682-2690 (Jun. 1997).
Ulbrich et al., "Leukocyte and endothelial cell adhesion molecules as targets for therapeutic interventions in inflammatory disease" *Trends in Pharmacology*, 24: 640-47 (2003).
Vachino et al., "P-Selectin Glycoprotein Ligand-1 is the Major Counter-Receptor for P-Selectin on Stimulated T Cells and Is Widely Distributed in Non-functional Form on Many Lymphotic Cells" *J. Biol. Chem.*, vol. 270, No. 37:21966-21974 (Sep. 15, 1995).
Watson et al., "Neutrophil Influx into an Inflammatory Site Inhibited by a Soluble Homing Receptor-IgG Chimera" *Nature*, vol. 349:164-167 (Jan. 10, 1991).
Wein et al., "Comparison of Human Eosinophil and Neutrophil Ligands for P-Selectin: Ligands for P-Selectin Differ from Those for E-Selectin" *Am. J. Respir. Cell. Mol. Biol.*, vol. 12:315-319 (1995).
Wilkins et al., "Tyrosine Sulfation of P-Selectin Glycoprotein Ligand-1 Is Required for High Affinity Binding to P-Selectin" *J. Biological Chem.*, vol. 270, No. 39:22677-22680 (Sep. 29, 1995).
Winn et al., "Anti-P-Selectin Monoclonal Antibody Attenuates Reperfusion Injury to the Rabbit Ear" *J. Clin. Invest.*, vol. 92:2042-2047 (Oct. 1993).
Zhou et al., "The Selectin GMP-140 Binds to Sialylated, Fucosylated Lactosaminoglycans on Both Myeloid and Nonmyeloid Cells", *J. Cell Biol.*, vol. 115, No. 2:557-564 (Oct. 1991).
James Darnell, Molecular Biology, pp. 54-55, 258-260, Scientific American Books (1986).
Copending U.S. Appl. No. 12/167,663.
Office Action mailed on Feb. 4, 2010, in related U.S. Appl. No. 12/167,663.
Final Office Action mailed on Jul. 21, 2010, in related U.S. Appl. No. 12/167,663.
Copending U.S. Appl. No. 12/167,705.
Office Action mailed on Feb. 4, 2010, in related U.S. Appl. No. 12/167,705.
Office Action dated Mar. 29, 2010, in Australian Patent Application No. 2007203133.
Office Action dated Apr. 22, 2010, in Mexican Patent Application No. PA/a/2004/012097.
Office Action dated Oct. 5, 2005, in Australian Patent Application No. 2001247929.
Office Action dated Oct. 27, 2006, in Australian Patent Application No. 2001247929.
International Search Report, mailed Aug. 2, 2002 for PCT/US01/10622.
Amersi, F., et al., "P-Selectin Glycoprotein Ligand-1 (rPSGL-Ig)-Mediated Blockade of CD62 Selectin Molecules Protects Rat Steatotic Liver Grafts from Ischemia/Reperfusion Injury," *Amer. Journal of Transplantation*, 2: 600-08 (2002).
Bevilacqua, et al., "Endothelial Leukocyte Adhesion Molecule 1: An Inducible Receptor for Neutrophils Related to Complement Regulatory Proteins and Lectins," *Science*, vol. 243: 1160-1165 (1989).
Collins, et al., "Continuous growth and differentiation of human myeloid leukaemic cells in suspension culture," *Nature*, vol. 270: 347-349 (1977).
Domchek, et al., "Inhibition of SH2 Domain/Phosphoprotein Association by a Nonhydrolyzable Phosphonopeptide," *Biochemistry*, vol. 31: 9865-9870 (1992).
Drickamer, K., "Two Distinct Classes of Carbohydrate-recognition Domains in Animal Lectins," *J. Biol. Chem.*, vol. 263(20): 9557-9560 (1988).
Dulkanchainun, T., et al., "Reduction of Hepatic Ischemia/Reperfusion Injury by a Soluble P-Selectin Glycoprotein Ligand-1," *Annals of Surgery*, vol. 227(6): 832-40 (1998).
Eppihimer, M. and Schaub, R., "Role of Selectin Inhibitors in the Pathogenesis of Deep Vein Thrombosis," *Journal of Leukocyte Biology*, 27 (1999).

Goding, J. W., "The Chromic Chloride Method of Coupling Antigens to Erythrocytes: Definition of Some Important Parameters," *J. Immunol. Methods*, vol. 10: 61-66 (1976).

Higgins, et al., "Aberrant O-Linked Oligosaccharide Biosynthesis in Lymphocytes and Platelets from Patients with the Wiskott-Aldrich Syndrome," *J. Biol. Chem.*, vol. 266(10): 6280-6290 (1991).

Horowitz, et al., "Expression of Chimeric Genes in the Early Region of SV40," *Journal of Molecular and Applied Genetics*, vol. 2(2): 147-159 (1983).

Kaufman, R. J., "Selection and Coamplification of Heterologous Genes in Mammalian Cells," *Methods in Enzymology*, vol. 185: 537-566 (1990).

Kaufman et al., "Selection and amplification of heterologous genes encoding adenosine deaminase in mammalian cells," *Proc. Natl. Acad. Sci.*, vol. 83: 3136-3140 (1986).

Kaufman et al., "Improved vectors for stable expression of foreign genes in mammalian cells by use of the untranslated leader sequence from EMC virus," *Nucleic Acids Research*, vol. 19(16): 4485-4490 (1991).

Kaufman, et al., "The Phosphorylation State of Eucaryotic Initiation Factor 2 Alters Translational Efficiency of Specific mRNAs," *Mol. Cell Biol.*, vol. 9(3): 946-958 (1989).

Khor, et al., "Pharmacokinetids, Pharmacodynamics, Allometry, and Dose Selection of rPSGL-Ig for Phase I Trial," *Journal of Pharmacology and Experimental Therapeutics*, vol. 293(2):618-624 (2000).

Krstenansky, J. L. and Mao, S. J. T., "Antithrombin properties of C-terminus of hirudin using synthetic unsulfated $N°$-acetyl-hirudin$_{45-65}$," *FEBS Letters*, vol. 211(1):10-16 (1987).

Kumar, et al., "Recombinant Soluble Form of PSGL-1 Accelerates Thrombolysis and Prevents Reocclusion in a Porcine Model," *Circulation*, vol. 99(10):1363-1369 (1999).

Laemmli, U. K., "Cleavage of Structural Proteins during the Assembly of the Head of Bacteriophage T4," *Nature*, vol. 227: 680-685 (1970).

Lasky, L. A., "Selectins: Interpreters of Cell-Specific Carbohydrate Information During Inflammation," *Science*, vol. 258: 964-969 (1992).

Lopata et al., "High level transient expression of a chloramphenicol acetyl transferase gene by DEAE-dextran mediated DNA transfection coupled with a dimethyl sulfoxide or glycerol shock treatment," *Nucleic Acids Research*, vol. 12(14): 5707-5717 (1984).

Lund, et al., "Human FcγRI and FcγRII Interact With Distinct But Overlapping Sites on Human IgG$^1$," *Journal of Immunology*, vol. 147(8): 2657-2662 (1991).

Luthman, H. and Magnusson, G., "High efficiency polyoma DNA transfection of chloroquine treated cells," *Nucleic Acids Research*, vol. 11(5): 1295-1308 (1983).

Maina et al., "An *Escherichia coli* vector to express and purify foreign proteins by fusion to and separation from maltose-binding protein," *Gene*, vol. 74: 365-373 (1988).

Merrifield, R. B., "Solid Phase Peptide Synthesis. I. The Synthesis of a Tetrapeptide," *J. Amer. Chem. Soc.*, vol. 85: 2149-2154 (1963).

McDowell, R. S. and Gadek, T. R., "Structural Studies of Potent Constrained RGD Peptides," *J. Amer. Chem. Soc.*, vol. 114(24): 9245-9253 (1992).

Morgan, et al., "The N-terminal end of the $C_H2$ domain of chimeric human IgG1 anti-HLA-DR is necessary for C1q, FcγRI and FcγRIII binding," *Immunology*, vol. 86: 319-324 (1995).

Natsuka, et al., "Molecular Cloning of a cDNA Encoding a Novel Human Leukocyte α-1,3-Fucosyltransferase Capable of Synthesizing the Sialyl Lewis x Determinant," *J. Biol. Chem.*, vol. 269(24): 16789-16794 (1994).

Rehemtulla, A. and Kaufman, R. J., "Protein processing within the secretory pathway," *Current Opinion in Biotechnology*, vol. 3: 560-565 (1992).

Riggs, P., "Expression and Purification of Maltose-Binding Protein Fusions," *Current Protocols in Molecular Biology*, 16.6.1-16.6.14 (1994).

Riggs, P., "Expression and Purification of Maltose-Binding Protein Fusions," *Current Protocols in Molecular Biology*, 16.6.1-16.6.12 (1990).

Saragovi, et al., "Loops and Secondary Structure Mimetics: Development and Applications in Basic Science and Rational Drug Design," *Bio/Technology*, vol. 10: 773-778 (1992).

Sasaki, et al., "Expression Cloning of a Novel α1,3-Fucosyltransferase That Is Involved in Biosynthesis of the Sialyl Lewis x Carbohydrate Determinants in Leukocytes," *J. Biol. Chem.*, vol. 269(20): 14730-14737 (1994).

Snapp, K. R., et al., "Dimerization of P-Selectin Glycoprotein Ligand-1 (PSGL-1) Required for Optimal Recognition of P-Selection," *Journal of Cell Biology*, vol. 142(1):263-70 (1998).

Sompayrac, L. M. and Danna, K. J., "Efficient infection of monkey cells with DNA of simian virus 40," *Proc. Natl. Acad. Sci.*, vol. 78(12): 7575-7578 (1981).

Urlaub, G. and Chasin, L., "Isolation of Chinese hamster cell mutants deficient in dihydrofolate reductase activity," *Proc. Natl. Acad. Sci.*, vol. 77(7): 4216-4220 (1980).

Ushiyama, et al., "Structural and Functional characterization of Monomeric soluble P-selectin and Comparison with Membrane P-selectin," *J. Biol. Chem.*, vol. 268(20): 15229-15237 (1993).

Van Den Ouweland, et al., "Structural homology between the human *fur* gene product and the subtilisin-like protease encoded by yeast KEX2," *Nucleic Acids Research*, vol. 18(3): 664; 1332 (1990).

Varki, A., "Radioactive tracer techniques in the sequencing of glycoprotein oligosaccharides," *The FASEB Journal*, vol. 5: 226-235 (1991).

Wakefield, et al., "Venous thrombosis prophylaxis by inflammatory inhibition without anticoagulation therapy," *Journal of Vascular Surgery*, vol. 31(2): 309-324 (2000).

Wasley, et al., "PACE/Furin Can Process the Vitamin K-dependent Pro-factor IX Precursor within the Secretory Pathway," *J. Biol. Chem.*, vol. 268(12): 8458-8465 (1993).

Zhang, et al., "Anti-Thrombotic Effect of a Recombinant Soluble P-Selectin Glycoprotein Ligand-1 Chimera in a Rat Model of Thrombosis," *Circulation*, vol. 100(18): I.471 (1999).

Zhang, et al., "A Recombinant Soluble P-Selectin Glycoprotein Ligand-1 Chimera has a Thrombolytic Effect In a Rat Model of Thrombosis," *Journal of the American College of Cardiology*, vol. 35(2): 280A (2000).

"Transmembrane protein," *Wikipedia*, http://en.wikipedia.org/wiki/Transmembrane_protein.

Complete file history of U.S. Appl. No. 09/935,144, issued as U.S. Patent No. 7,563,760.

Complete file history of U.S. Appl. No. 08/713,556, issued as U.S. Patent No. 6,277,975.

Complete file history of U.S. Appl. No. 08/428,734, issued as U.S. Patent No. 5,843,707.

Complete file history of U.S. Appl. No. 08/316,305, now abandoned.
Complete file history of U.S. Appl. No. 08/235,398, now abandoned.
Complete file history of U.S. Appl. No. 08/112,608, now abandoned.
Complete file history of U.S. Appl. No. 07/965,662, now abandoned.

Fifth Official Action in Mexican Patent Application No. PA/a/2004/012097.

Epperson, et al., "Noncovalent Association of P-selectin Glycoprotein Ligand-1 and Minimal Determinants for Binding to P-selectin," *J. Biol. Chem.*, vol. 275(11): 7839-7853 (2000).

Hicks, et al., "Glycosulfopeptides modeled on P-selectin glycoprotein ligand-1 inhibit P-selectin-dependent leukocyte rolling in vivo," *The FASEB Journal* express article 10.1096/fj.02-0075fje. (published online Jul. 1, 2002).

Leppänen, et al., "A novel Glycosulfopeptide Binds to P-selectin and Inhibits Leukocyte Adhesion to P-selectin," *J. Biol. Chem.*, vol. 274(35): 24838-24848 (1999).

Ramachandran et al., "Dimerization of a selectin and its ligand stabilizes cell rolling and enhances tether strength in shear flow," *PNAS*, vol. 98(18): 10166-10171 (2001).

Yang, et al., "Mouse P-selectin glycoprotein ligand-1: molecular cloning, chromosomal localization, and expression of a functional P-selectin receptor," *Blood*, vol. 87(10): 4176-4186 (1996).

Final Office Action mailed on Oct. 20, 2010, in related U.S. Appl. No. 12/167,705, (7 pages).

Office Action dated Oct. 27, 2010, in Canadian Patent Application No. 2,599,944 (2 pages).

Moore et al., "The P-selectin Glycoprotein Ligand from Human Neutrophils Displays Sialylated, Fucosylated, O-Linked Poly-*N*-acetyllactosamine," *J. Biol. Chem.*, vol. 269(37): 23318-23327 (1994).

\* cited by examiner mAb 275

Lecγ1

Soluble "T7" Trucated Form:

35S-Met Labeled

*Captured with Protein A*
1. 148.Fc
2. 148.Q70.Fc
3. 148.H24.Q70.Fc

*Captured with P-Sel.Fc*
4. 148.Fc
5. 18.Q70.Fc
6. 148.H24.Q70.Fc

| | Sample | Chlorate |
|---|---|---|
| M. | mw marker | |
| 1. | YYY.19Fc | − |
| 2. | YYY.19Fc | + |
| 3. | FYY.19Fc | − |
| 4. | FYY.19Fc | + |
| 5. | FFY.19Fc | − |
| 6. | FFY.19Fc | + |
| 7. | FFF.19Fc | − |
| 8. | FFF.19Fc | + |

35S-Met-Labeled

1. FYY.19.Fc
2. FFF.19.Fc

35SO₄ Labeled

3. Mock
4. P-Sel.LE.Fc
5. FYY.19.Fc
6. FFF.19.Fc

Fig. 12

| | Selectin Binding | | |
|---|---|---|---|
| | P | E | L |
| 253.Fc | +++ | +++ | ++ |
| 148.Fc | +++ | +++ | ++ |
| 47.Fc | +++ | +++ | ++ |
| 19.Fc | ++ | + | − |

Fig. 16

| | Selectin Binding | | |
|---|---|---|---|
| | P | E | L |
| 148.Fc (YYYD ... N24 ... N70 ... IgG1.Fc) | +++ | +++ | ++ |
| ΔY.148.Fc (N24 ... N70 ... IgG1.Fc) | − | +++ | − |
| FFFE.148.Fc (FFFE ... N24 ... N70 ... IgG1.Fc) | + | +++ | − |

- O-linked carbohydrate at Thr16

Fig. 21

| | | Selectin Binding | | |
|---|---|---|---|---|
| | | P | E | L |
| YYYD 19.Fc | YYY − sLe$^X$ / IgG1 | +++ | + | − |
| FYYD 19.Fc | FYY − sLe$^X$ / IgG1 | ++ | + | − |
| FFYD 19.Fc | FFY − sLe$^X$ / IgG1 | + | + | − |
| FFFD 19.Fc | FFF − sLe$^X$ / IgG1 | + | + | − |
| FFYDN1619.Fc | YYY  N16 / IgG1 | − | − | − |

Key:

A - "T7" sPSGL-1

B - "ΔTM" sPSGL-1

C - "I316" sPSGL-1

D - "Qc" sPSGL-1

Fig. 30

| | E-selectin Inhibition | P-selectin Inhibition |
|---|---|---|
| Q A T E Y E Y L D Y D F L P E C | − | ++(~60μM) |
| T E Y E Y L D Y D F | | ++ |
| S Y(PO3) L D Y(PO3) S | + | +++(~10μM) |
| S Y(PO3) L D Y S | | + |
| S Y L D Y S | | − |
| S F L D Y(PO3) S | | − |
| Ac Y(PO3) L D Y(PO3) NH2 | | + |
| Ac L D Y(PO3) NH2 | | − |
| S Y L D Y(SO3) S | | − |

NUCLEIC ACIDS ENCODING P-SELECTIN LIGAND FUSION PROTEINS

This application is a division of application Ser. No. 09/935,144, filed Aug. 21, 2001, now U.S. Pat. No. 7,563,760, which is a continuation of application No. 08/713,556, filed Aug. 30, 1996, issued as U.S. Pat. No. 6,277,975, which is a continuation-in-part of application No. 08/428,734, filed Apr. 25, 1995, issued as U.S. Pat. No. 5,843,707, which is a continuation-in-part of application No. 08/316,305, filed Sep. 30, 1994, now abandoned, which is a continuation-in-part of application No. 08/235,398, filed Apr. 28, 1994, now abandoned, which is a continuation-in-part of application No. 08/112,608, filed Aug. 26, 1993, now abandoned, which is a continuation-in-part of application No. 07/965,662, filed Oct. 23, 1992, now abandoned, which are incorporated by reference in their entireties. This application also claims priority from International application No. PCT/US93/10168, filed Oct. 22, 1993, which is incorporated by reference in its entirety.

BACKGROUND OF THE INVENTION

The present invention relates to the field of anti-inflammatory substances which act by inhibiting leukocyte adhesion to endothelial cells. More particularly, the present invention is directed to novel ligands for the mammalian adhesion proteins known as selectins.

During inflammation leukocytes adhere to the vascular endothelium and enter subendothelial tissue, an interaction which is mediated by specific binding of the selectin or LEC-CAM class of proteins to ligands on target cells. Such selectin-mediated cellular adhesion also occurs in thrombotic disorders and parasitic diseases and may be implicated in metastatic spread of tumor cells.

The selectin proteins are characterized by a N-terminal lectin-like domain, an epidermal growth factor-like domain, and regions of homology to complement binding proteins. Thus far three human selectin proteins have been identified, E-selectin (formerly ELAM-1), L-selectin (formerly LAM-1) and P-selectin (formerly PADGEM or GMP-140). E-selectin is induced on endothelial cells several hours after activation by cytokines, mediating the calcium-dependent interaction between neutrophils and the endothelium. L-selectin is the lymphocyte homing receptor, and P-selectin rapidly appears on the cell surface of platelets when they are activated, mediating calcium-dependent adhesion of neutrophils or monocytes to platelets. P-selectin is also found in the Weibel-Palade bodies of endothelial cells; upon its release from these vesicles P-selectin mediates early binding of neutrophils to histamine- or thrombin-stimulated endothelium.

Selectins are believed to mediate adhesion through specific interactions with ligands present on the surface of target cells. Generally the ligands of selectins are comprised at least in part of a carbohydrate moiety. For example, E-selectin binds to carbohydrates having the terminal structure

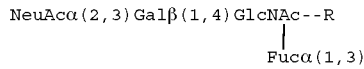

and also to carbohydrates having the terminal structure

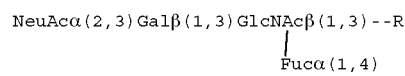

where R=the remainder of the carbohydrate chain. These carbohydrates are known blood group antigens and are commonly referred to as sialyl Lewis$^x$ and sialyl Lewis$^a$, respectively. The presence of the sialyl Lewis$^x$ antigen alone on the surface of an endothelial cell may be sufficient to promote binding to an E-selectin expressing cell. E-selectin also binds to carbohydrates having the terminal structures

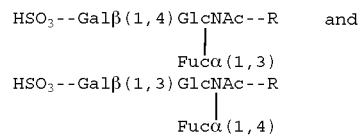

As with E-selectin, each selectin appears to bind to a range of carbohydrates with varying affinities. The strength of the selectin mediated adhesive event (binding affinity) may also depend on the density of the carbohydrate and on the density of the selectin on the cell surface.

P-selectin binds to carbohydrates containing the non-sialated form of the Lewis$^x$ blood group antigen and with higher affinity to sialyl Lewis$^x$. P-selectin may also recognize sulfatides, which are heterogeneous 3-sulfated galactosyl ceramides, isolated from myeloid and tumor cells by lipid extraction. However, the binding of cells bearing P-selectin to cells bearing P-selectin ligands is abolished when the ligand-bearing cells are treated with proteases, indicating that the P-selectin ligand may be a glycoprotein.

Two putative glycoprotein ligands for P-selectin have recently been identified, one of which has been partially purified, (Moore et al., J. Cell Biol. 118, 445-456 (1992)). However, neither amino acid composition nor the amino acid sequence of these glycoproteins are disclosed.

SUMMARY OF THE INVENTION

In one embodiment, the present invention provides a composition comprising an isolated DNA encoding a P-selectin ligand protein, said protein comprising the amino acid sequence set forth in SEQ ID NO:2 from amino acid 1 to amino acid 402. Also provided is a composition comprising an isolated DNA encoding a soluble P-selectin ligand protein, said protein comprising the amino acid sequence set forth in SEQ ID NO:2 from amino acid 1 to amino acid 310. The invention further provides a composition comprising an isolated DNA encoding a mature P-selectin ligand protein, said protein comprising the amino acid sequence set forth in SEQ ID NO:2 from amino acid 42 to amino acid 402. In another embodiment, the invention provides a composition comprising an isolated DNA encoding a soluble mature P-selectin ligand protein, said protein comprising the amino acid sequence set forth in SEQ ID NO:2 from amino acid 42 to amino acid 310. In another embodiment, the invention provides a composition comprising an isolated DNA encoding a P-selectin ligand protein, said protein comprising the amino acid sequence set forth in SEQ ID NO:4. The invention further provides a composition comprising an expression vector comprising any one of the isolated DNAs of the invention, said DNA being operably linked to an expression control sequence; a host cell transformed with the expression vector containing any one of the DNAs described above; and a process for producing the P-selectin ligand protein, which comprises:

(a) culturing a host cell transformed with an expression vector containing any one of the DNAs of the invention in a suitable culture medium; and (b) purifying the P-selectin ligand protein from the culture medium.

In another embodiment, the invention provides a composition comprising a protein comprising the amino acid sequence set forth in SEQ ID NO:2 from amino acid 21 to amino acid 402, said protein being substantially free from other mammalian proteins. The invention further comprises a soluble P-selectin ligand protein comprising the amino acid sequence set forth in SEQ ID NO:2 from amino acid 21 to amino acid 310, said protein being substantially free from other mammalian proteins. In another embodiment, the invention comprises a P-selectin ligand protein comprising the amino acid sequence set forth in SEQ ID NO:2 from amino acid 1 to amino acid 402, said protein being substantially free from other mammalian proteins. The invention also provides a composition comprising a mature P-selectin ligand protein comprising the amino acid sequence set forth in SEQ ID NO:2 from amino acid 42 to amino acid 402, said protein being substantially free from other mammalian proteins. Further provided is a composition comprising a soluble mature P-selectin ligand protein comprising the amino acid sequence set forth in SEQ ID NO:2 from amino acid 42 to amino acid 310, said protein being substantially free from other mammalian proteins. In another embodiment, the invention provides a composition comprising a protein comprising the amino acid sequence set forth in SEQ ID NO:4.

In yet another embodiment, the invention provides compositions comprising antibodies specific for P-selectin ligand proteins.

In another embodiment, the invention provides a method of identifying an inhibitor of P-selectin-mediated intercellular adhesion which comprises:

(a) combining a P-selectin protein with a P-selectin ligand protein comprising an amino acid sequence selected from the group consisting of the amino acid sequence set forth in SEQ ID NO:2 from amino acid 1 to amino acid 402, the amino acid sequence set forth in SEQ ID NO:2 from amino acid 42 to amino acid 402, the amino acid sequence set forth in SEQ ID NO:2 from amino acid 42 to amino acid 310, and the amino acid sequence set forth in SEQ ID NO:4, said combination forming a first binding mixture;

(b) measuring the amount of binding between the P-selectin protein and the P-selectin ligand protein in the first binding mixture;

(c) combining a compound with the P-selectin protein and the P-selectin ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting P-selectin-mediated intercellular adhesion when a decrease in the amount of binding of the second binding mixture occurs.

In another embodiment, the invention provides a method of identifying an inhibitor of E-selectin-mediated intercellular adhesion which comprises:

(a) combining a E-selectin protein with a P-selectin ligand protein comprising an amino acid sequence selected from the group consisting of the amino acid sequence set forth in SEQ ID NO:2 from amino acid 1 to amino acid 402, the amino acid sequence set forth in SEQ ID NO:2 from amino acid 42 to amino acid 402, the amino acid sequence set forth in SEQ ID NO:2 from amino acid 42 to amino acid 310, and the amino acid sequence set forth in SEQ ID NO:4, said combination forming a first binding mixture;

(b) measuring the amount of binding between the E-selectin protein and the P-selectin ligand protein in the first binding mixture;

(c) combining a compound with the E-selectin protein and the P-selectin ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting E-selectin-mediated intercellular adhesion when a decrease in the amount of binding of the second binding mixture occurs. These methods may also be used to look for L-selectin inhibitors by substituting L-selectin for E-selectin.

The invention also encompasses processes for producing P-selectin ligand proteins which comprise (a) co-transforming a host cell with a DNA encoding a P-selectin ligand protein and a DNA encoding a fucosyltransferase capable of synthesizing sialyl Lewis X (sLe$^x$) or sialyl Lewis A (sLe$^a$) (such as an ($\alpha$1,3/$\alpha$1,4) fucosyltransferase or an ($\alpha$1,3) fucosyltransferase), each of said DNAs being operably linked to an expression control sequence; (b) culturing the host cell in suitable culture medium; and (c) purifying the P-selectin ligand protein from the culture medium. In certain other embodiments, the host cell is also co-transformed with a DNA encoding a paired basic amino acid converting enzyme and/or a DNA encoding a GlcNAc transferase (preferably a "core2 transferase"). In preferred embodiments, the P-selectin ligand protein is a full-length or soluble form.

In other embodiments, the present invention includes a P-selectin ligand protein having P-selectin ligand protein activity. In preferred embodiments, the ligand protein is a protein comprising the sequence from amino acid 42 to amino acid 60 of SEQ ID NO: 2, consisting essentially of the sequence from amino acid 42 to amino acid 60 of SEQ ID NO: 2, comprising the sequence from amino acid 42 to amino acid 88 of SEQ ID NO: 2, consisting essentially of the sequence from amino acid 42 to amino acid 88 of SEQ ID NO: 2, consisting essentially of the sequence from amino acid 42 to amino acid 118 of SEQ ID NO: 2, or consisting essentially of the sequence from amino acid 42 to amino acid 189 of SEQ ID NO: 2. In other preferred embodiments, at least one of the asparagine residues at positions 65, 11 and 292 of SEQ ID NO: 2 have been deleted or replaced. Certain preferred embodiments of the ligand protein comprises at least one of the tyrosine residues at positions 46, 48 and 51 of SEQ ID NO: 2. DNAs encoding these P-selectin ligand proteins, host cells transformed with such DNAs, process for producing protein by culturing such host cells, pharmaceutical compositions comprising the proteins, methods of identifying selectin binding inhibitors using the proteins, antibodies to the proteins and methods of inhibiting selectin mediated binding using the proteins are also encompassed by the invention.

In yet other embodiments the invention provides an isolated DNA encoding a fusion protein comprising (a) a first amino acid sequence comprising amino acid 42 to amino acid 60 of SEQ ID NO:2, and (b) a second amino acid sequence derived from the sequence of a protein other than P-selectin ligand. Preferably, an expression control sequence is operably linked to the nucleotide sequence. Host cells transformed with such DNAs are also provided. The invention also provides a process for producing a fusion protein, which comprises: (a) culturing the host cell under condition suitable for expression of the fusion protein; and (b) purifying the fusion protein from the culture medium. Fusion proteins produced according to such process are also provide.

In certain preferred embodiments, the first amino acid sequence of such fusion protein comprises amino acid 42 to amino acid 402 of SEQ ID NO:2, amino acid 42 to amino acid 310 of SEQ ID NO:2, amino acid 42 to amino acid 88 of SEQ ID NO:2, amino acid 42 to amino acid 118 of SEQ ID NO:2, or amino acid 42 to amino acid 189 of SEQ ID NO:2.

In other preferred embodiments, the DNA comprises the nucleotide sequence of SEQ ID NO:35 from nucleotide 123 to nucleotide 939, the nucleotide sequence of SEQ ID NO:35, the nucleotide sequence of SEQ ID NO:37 from nucleotide 123 to nucleotide 807, the nucleotide sequence of SEQ ID NO:37, the nucleotide sequence of SEQ ID NO:39 from nucleotide 123 to nucleotide 1311, the nucleotide sequence of SEQ ID NO:39, the nucleotide sequence of SEQ ID NO:41 from nucleotide 123 to nucleotide 792, or the nucleotide sequence of SEQ ID NO:41.

The present invention also provides a fusion protein comprising (a) a first amino acid sequence comprising amino acid 42 to amino acid 60 of SEQ ID NO:2, and (b) a second amino acid sequence derived from the sequence of a protein other than P-selectin ligand. Preferably, the first amino acid sequence comprises amino acid 42 to amino acid 402 of SEQ ID NO:2, amino acid sequence comprises amino acid 42 to amino acid 310 of SEQ ID NO:2, amino acid 42 to amino acid 88 of SEQ ID NO:2, amino acid 42 to amino acid 118 of SEQ ID NO:2, or amino acid 42 to amino acid 189 of SEQ ID NO:2.

In certain particularly preferred embodiments, the fusion protein comprises the amino acid sequence of SEQ ID NO:36 from amino acid 42 to amino acid 313, the amino acid sequence of SEQ ID NO:36, the amino acid sequence of SEQ ID NO:38 from amino acid 42 to amino acid 269, the amino acid sequence of SEQ ID NO:38, the amino acid sequence of SEQ ID NO:40 from amino acid 42 to amino acid 437, the amino acid sequence of SEQ ID NO:40, the amino acid sequence of SEQ ID NO:42 from amino acid 42 to amino acid 264, or the amino acid sequence of SEQ ID NO:42.

In other preferred embodiments, the second amino acid sequence is linked to the C-terminus or the N-terminus of the first amino acid sequence, with or without being linked by a linking sequence.

In yet other embodiments, the second amino acid sequence is derived from a protein selected from the group consisting of an antibody, a cytokine, a growth factor, a differentiation factor, a hormone, an enzyme, a receptor or fragment thereof and a ligand. Preferably, the second amino acid sequence is derived from the sequence of an antibody, from the Fc portion of an antibody, or is a mutation of a sequence derived from an antibody.

In yet further embodiments, the present invention provides for a composition comprising (a) a first peptide comprising amino acid 42 to amino acid 60 of SEQ ID NO:2, and (b) a second peptide derived from the sequence of a protein other than P-selectin ligand, wherein the first peptide and the second peptide are chemically linked by a moiety other than a peptide bond. Any P-selectin ligand protein of the invention can be used in such a composition.

BRIEF DESCRIPTION OF THE FIGURES

FIG. 12 is a schematic representation of several P-selectin ligand protein fragments constructed for the purpose of examining the effects of various deletions on the binding of the P-selectin ligand proteins to selecting.

FIGS. 14-17 depict the results of experiments comparing the binding of various deleted and altered P-selectin ligand proteins to selectins.

FIGS. 19-21 depict the results of experiments comparing the binding of various deleted and altered P-selectin ligand proteins to selecting.

Some of the foregoing figures employ a convention for numbering amino acids within the depicted constructs which is different that the residue numbering employed in SEQ ID NO:2. In the figures, residues are numbered using the first amino acid of soluble mature P-selectin ligand as a starting point. Hence, the residue numbers used in the figures are 41 less than those of SEQ ID NO:2. For example, residue 19 in the figures corresponds to residue 60 in SEQ ID NO:2.

Figure 25:
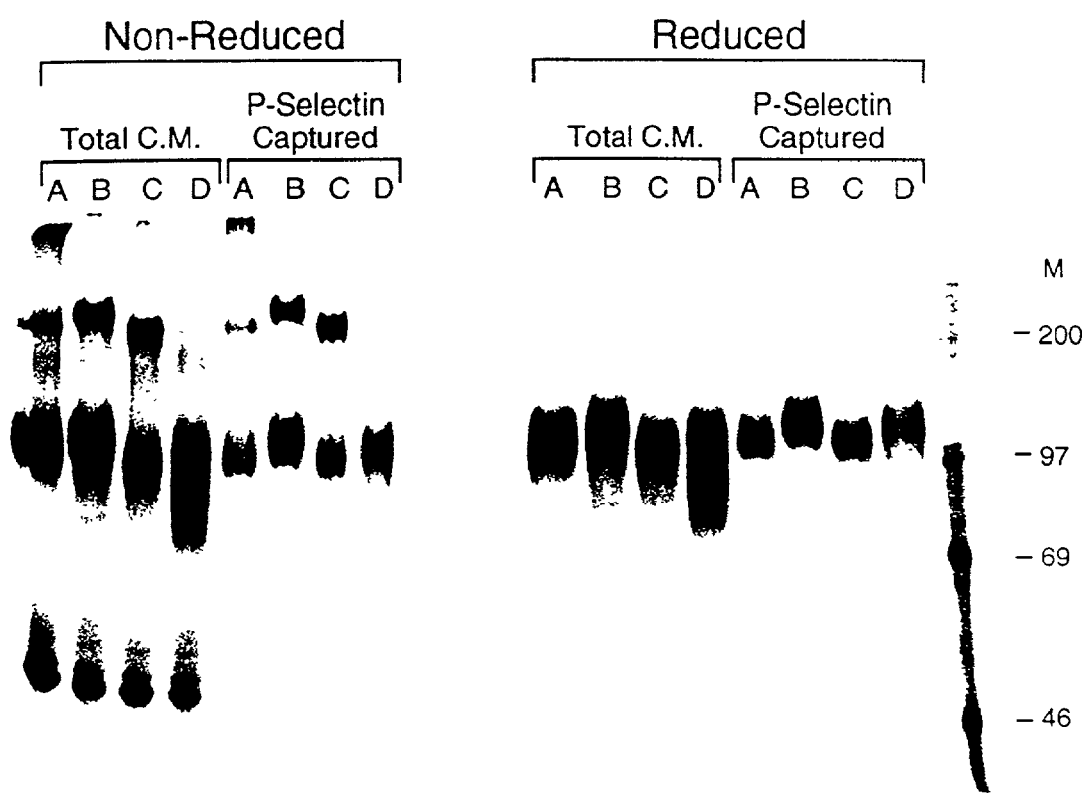

FIG. 25 is an analysis of the expression products of CHO cells, already expressing ¾ fucosyltransferase and Core2 transferase, which were transfected with psPSL.T7, ΔTM, 1316 or psPSL.QC and amplified using methotrexate. Conditioned media was either analyzed directly or first precipitated with LEC-γ1 and then analyzed by SDS-PAGE under non-reducing and reducing conditions.

Figure 26:
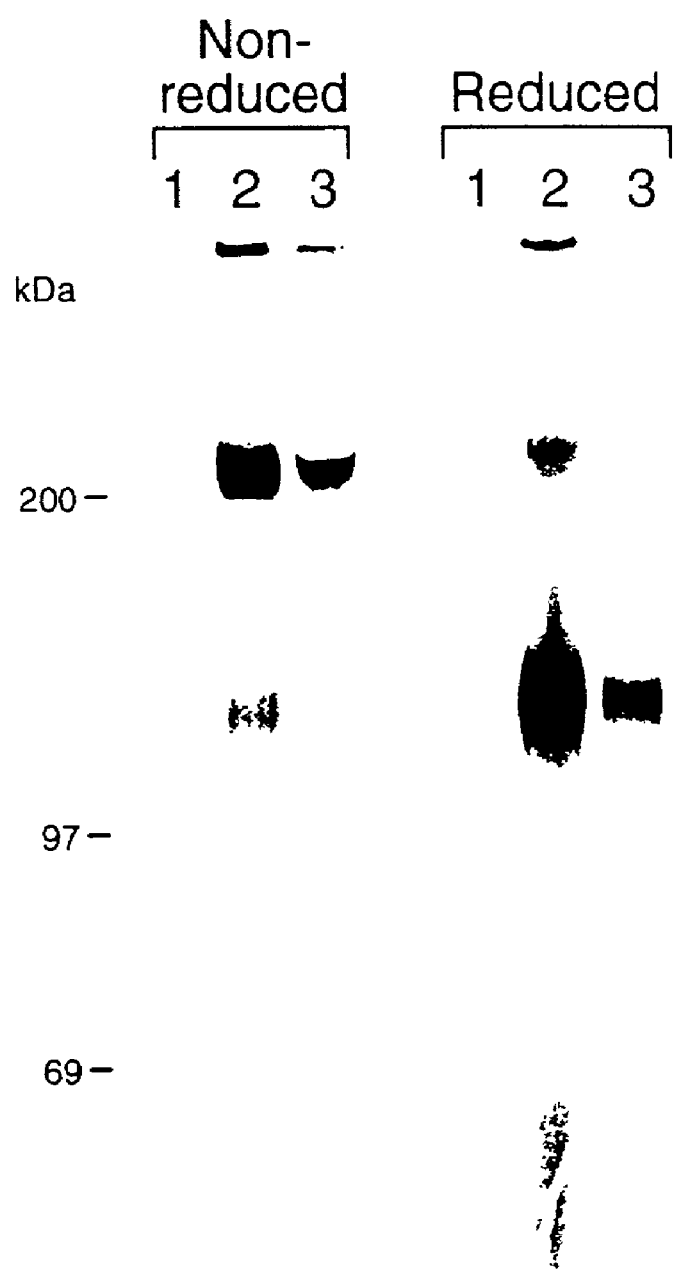

FIG. 26. SDS-PAGE separation of myeloid cell membrane proteins affinity captured by P- and E-selectin. Membrane lysates were prepared from U937 cells metabolically labeled with ³H-glucosamine and subjected to affinity precipitation with immobilized P- and E-selectin and control human IgG₁. Eluted proteins were treated with ("reduced") or without ("non-reduced") DTT prior to gel electrophoresis. Lanes: 1, affinity capture by human IgG₁; 2, affinity capture by P-selectin; 3, affinity capture by E-selectin.

Figure 27:
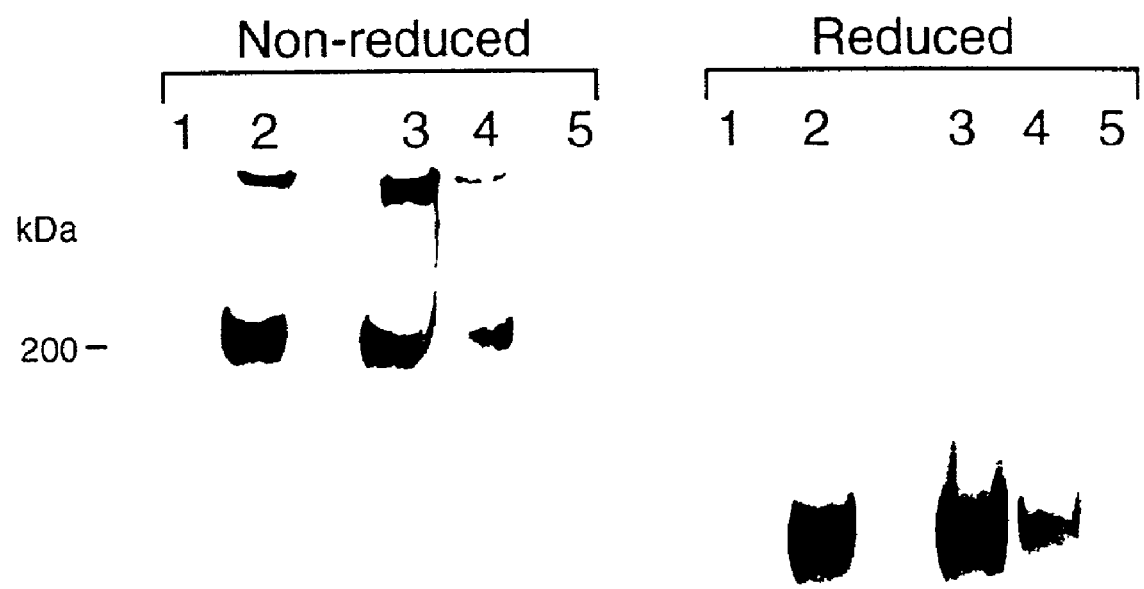

FIG. 27. Sequential affinity capture experiments. ³H-labeled U937 lysate species were affinity captured by P- or E-selectin, eluted, and then subjected to immunoprecipitation with anti-PSGL-1 antiserum Rb3443. Lanes: 1 and 2, control immunoprecipitations of fresh myeloid cell membrane lysates using pre-immune rabbit serum (lane 1) and Rb3443 (lane 2); 3-5, immunoprecipitation with Rb3443 of myeloid cell membrane lysates previously affinity captured and eluted from P-selectin (lane 3), E-selectin (lane 4), and human IgG₁ (lane 5).

Figure 28:
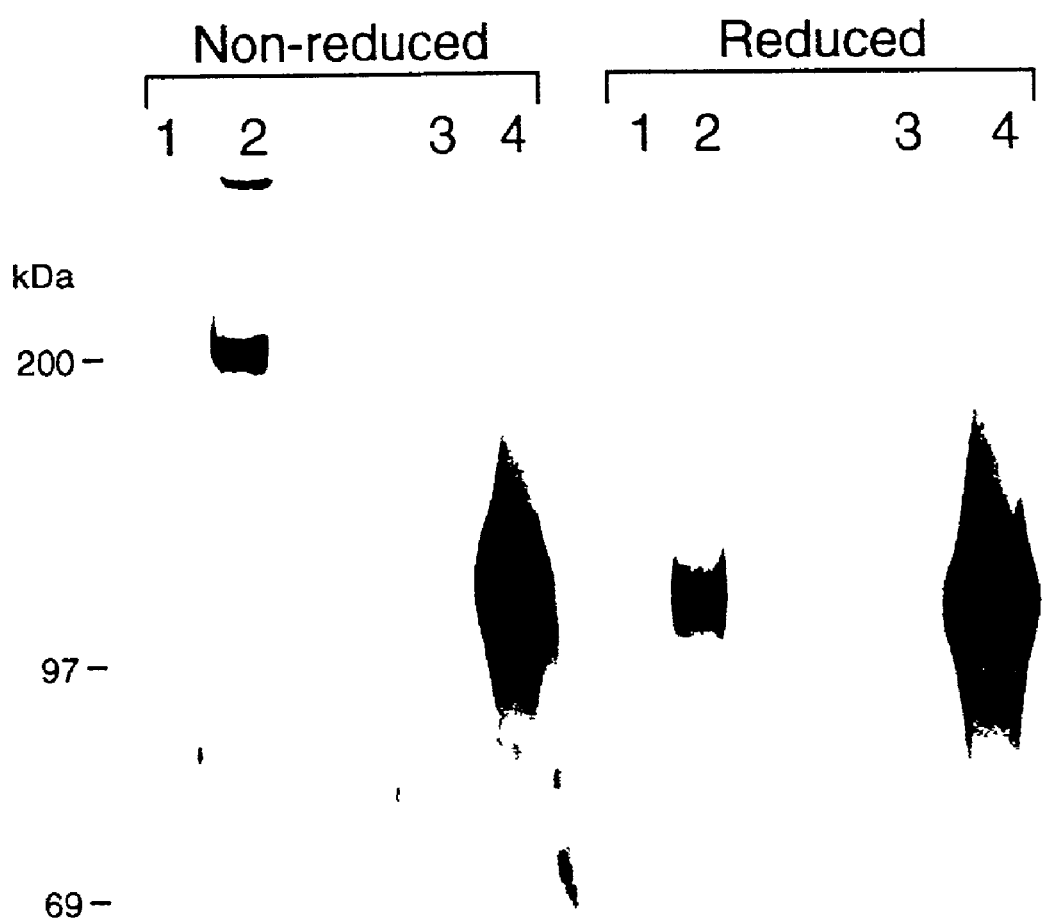

FIG. 28. Comparison of CD43 and PSGL-1 content of myeloid cell membrane extracts. Labeled U937 cell extracts were immunoprecipitated with anti-PSGL-1 rabbit polyclonal antibody Rb3443 or an anti-CD43 mouse MAb and then subjected to SDS-PAGE/autoradiography. Lanes: 1, immunoprecipitation with control pre-immune rabbit serum; 2, immunoprecipitation with Rb3443; 3, immunoprecipitation with control isotype-matched mouse antibody; 4, immunoprecipitation with anti-CD43 antibody.

Figure 29:
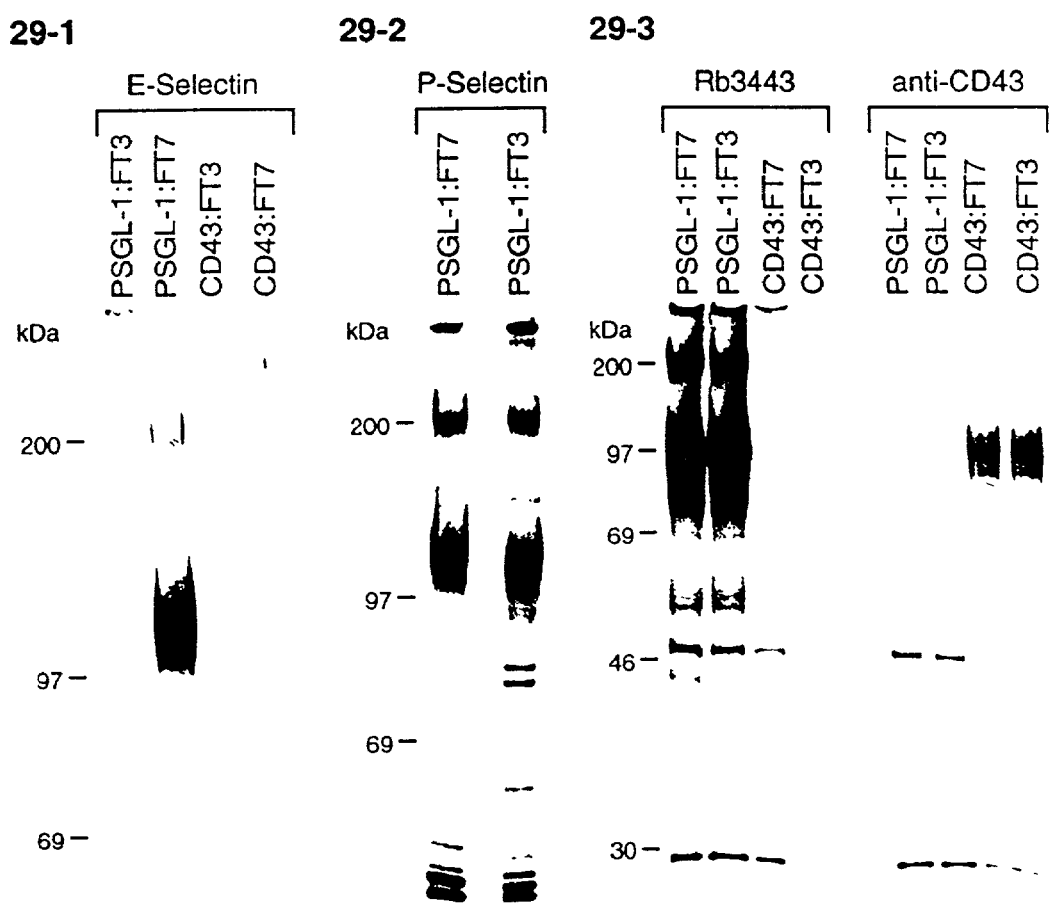

FIG. 29. COS transfection experiments. COS M6 cells transfected with plasmids encoding PSGL-1 or CD43 as well as Fuc-TIII or Fuc-TVII were metabolically labeled with ³⁵S-methionine, and membranes were prepared for affinity capture experiments as described in Materials and Methods. The cDNAs employed in the transfections are indicated above the lanes. Precipitations were performed using (A) E-selectin, (B) P-selectin, and (C) anti-PSGL-1 antiserum Rb3443 and anti-CD43 MAb.

FIG. 30 summarizes the results of screening of various P-selecint ligand proteins for inhibition of P- and E-selectin binding (see Example 13).

DETAILED DESCRIPTION OF THE INVENTION

The present inventors have for the first time identified and isolated a novel DNA which encodes a protein which acts as a ligand for P-selectin on human endothelial cells and platelets. The sequence of the DNA is set forth in SEQ ID NO:1. The complete amino acid sequence of the P-selectin ligand protein (i.e., the mature peptide plus the leader sequence) is characterized by the amino acid sequence set forth in SEQ ID NO:2 from amino acid 1 to amino acid 402. Hydrophobicity analysis and comparison with known cleavage patterns predict a signal sequence of 20 to 22 amino acids, i.e., amino acids 1 to 20 or amino acids 1 to 22 of SEQ ID NO:2. The P-selectin ligand protein contains a PACE (paired basic amino acid converting enzyme) cleavage site (-Arg-Asp-Arg-Arg-) at amino acids 3841 of SEQ ID NO:2. The mature P-selectin ligand protein of the present invention is characterized by the amino acid sequence set forth in SEQ ID NO:2 from amino acid 42 to amino acid 402. A soluble form of the P-selectin ligand protein is characterized by containing amino acids 21 to 310 of SEQ ID NO:2. Another soluble form of the mature P-selectin ligand protein is characterized by the amino acid sequence set forth in SEQ ID NO:2 from amino acid 42 to amino acid 310. The soluble form of the P-selectin ligand protein is further characterized by being soluble in aqueous solution at room temperature. Of course, the corresponding DNA sequences as set forth in SEQ ID NO:1 encoding these proteins are also included in the subject invention.

The P-selectin ligand of the invention is a glycoprotein which may contain one or more of the following terminal carbohydrates:

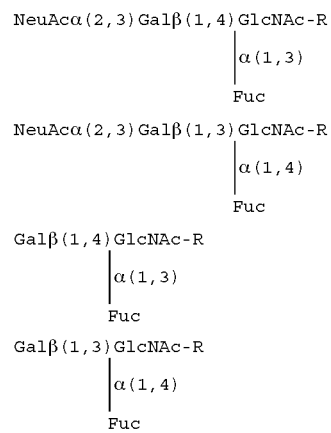

where R=the remainder of the carbohydrate chain, which is covalently attached either directly to the P-selectin ligand protein or to a lipid moiety which is covalently attached to the P-selectin ligand protein. The P-selectin ligand glycoprotein of the invention may additionally be sulfated or otherwise post-translationally modified. As expressed in COS and CHO cells, full length P-selectin ligand protein (amino acids 1 to 402 of SEQ ID NO:2 or amino acids 42 to 402 of SEQ ID NO:2) is a homodimeric protein having an apparent molecular of 220 kD as shown by non-reducing SDS-polyacrylamide gel electrophoresis.

Figure 5:
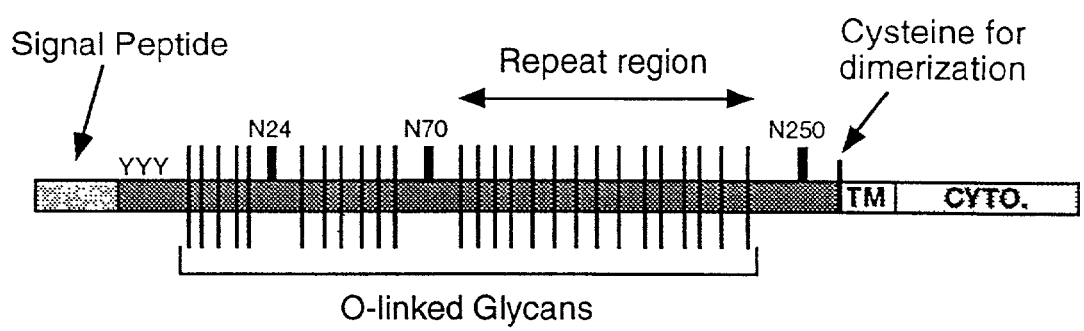
FIG. 5 is a schematic representation of structural features of the full length P-selectin ligand protein of SEQ ID NO: 2.
Figure 5:
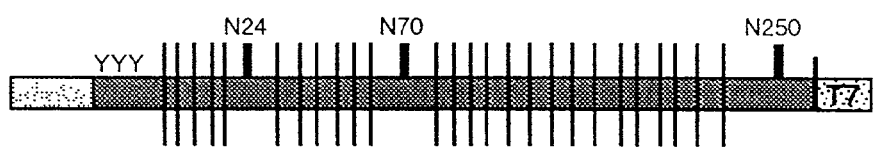

The structure of the full-length P-selectin ligand protein is schematically represented in FIG. 5. Three regions of the P-selectin ligand protein of SEQ ID NO:2 are: an extracellular domain (from about amino acid 21 to 310 of SEQ ID NO:2), a transmembrane domain (from about amino acid 311 to 332 of SEQ ID NO:2), and an intracellular, cytoplasmic domain (from about amino acid 333 to 402 of SEQ ID NO:2). The extracellular domain contains three consensus tripeptide sites (Asn-X-Ser/Thr) of potential N-linked glycosylation beginning at Asn residues 65, 111, and 292. The extracellular domain further contains three potential sites of tyrosine sulfation at residues 46, 48, and 51. The region comprised of residues 55-267 contains a high percentage of proline, serine, and threonine including a subdomain of fifteen decameric repeats of the ten amino acid consensus sequence Ala-Thr/Met-Glu-Ala-Gln-Thr-Thr-X-Pro/Leu-Ala/Thr, wherein X can be either Pro, Ala, Gln, Glu, or Arg. Regions such as these are characteristic of highly O-glycosylated proteins.

COS or CHO cells co-transfected with a gene encoding the P-selectin ligand protein and a gene encoding fucosyltransferase (hereinafter FT), preferably an (α1,3/α1,4) fucosyltransferase ("3/4FT"), are capable of binding to CHO cells expressing P-selectin on their surface, but are not capable of binding to CHO cells which do not express P-selectin on their surface. In order to bind to P-selectin, either in purified form or expressed on the surface of CHO cells, the gene encoding the P-selectin ligand protein must be co-transfected with the gene encoding an FT, since transfection of either gene in the absence of the other either abolishes or substantially reduces the P-selectin binding activity. The binding of the P-selectin ligand protein of the invention to P-selectin can be inhibited by EDTA or by a neutralizing monoclonal antibody specific for P-selectin. The binding of the P-selectin ligand protein of the invention to P-selectin is not inhibited by a non-neutralizing monoclonal antibody specific for P-selectin or by an isotype control. These results characterize the binding specificity of the P-selectin ligand protein of the invention.

For the purposes of the present invention, a protein is defined as having "P-selectin ligand protein activity", i.e., variably referred to herein as a "P-selectin ligand protein", or as a "P-selectin ligand glycoprotein" or simply as a "P-selectin ligand", when it binds in a calcium-dependent manner to P-selectin which is present on the surface of cells as in the CHO-P-selectin binding assay of Example 4, or to P-selectin which is affixed to another surface, for example, as the chimeric P-selectin-IgGγ1 protein of Example 4 is affixed to Petri dishes.

The glycosylation state of the P-selectin ligand protein of the invention was studied using a chimeric, soluble form of the P-selectin ligand protein, described in detail in Example 5(C) and designated sPSL.T7. The sPSL.T7 protein produced from COS cells co-transfected with 3/4FT is extensively modified by post-translational glycosylation, as described in detail in Example 6(C). Thus, it is believed that both N- and O-linked oligosaccharide chains, at least some of which are sialated, are present on the P-selectin ligand protein of the invention.

The P-selectin ligand protein of the invention may also bind to E-selectin and L-selectin. Conditioned medium from COS cells which have been co-transfected with the DNA encoding sPSL.T7 or P-selectin ligand-Ig fusions and with the DNA encoding 314FT, when coated on wells of plastic microtiter plates, causes CHO cells which express E-selectin to bind to the plates; however CHO cells which do not express E-selectin do not bind to such plates. The binding of CHO cells which express E-selectin to microtiter plates coated with conditioned medium from COS cells which have been co-transfected with the DNA encoding sPSL.T7 and with the DNA encoding 3/4FT is abolished in the presence of EDTA or of a neutralizing antibody specific for E-selectin. Conditioned medium from COS cells transfected only with the sPSL.T7 DNA does not cause binding of CHO cells which express E-selectin when coated on wells of microtiter plates. For these reasons, the P-selectin ligand protein of the invention is believed to be useful as an inhibitor of E-selectin-mediated intercellular adhesion in addition to P-selectin-mediated intercellular adhesion.

Antibodies raised against COS-produced soluble P-selectin ligand protein are immunoreactive with the major HL-60 glycoprotein that specifically binds P-selectin as determined by affinity capture using an immobilized Fc chimera of P-selectin. U937 cells bear a similar immunoreactive glycoprotein ligand. Thus, a single glycoprotein species is observed upon EDTA elution of immobilized P-selectin previously incubated with detergent extracts of $^3$H-glucosamine labeled U937 cells. This major species exhibits an apparent molecular weight by SDS-PAGE of 220 kD under non-reducing conditions and 100 kD under reducing conditions. As with the comparable species isolated from HL-60 cells, this U937 ligand is immunoreactive with a polyclonal antibody raised against COS recombinant P-selectin ligand protein. In addition, affinity capture of E-selectin ligands from U937 cell and cell membrane preparations, using an immobilized Fc chimera of E-selectin, yield a single major species with identical mass and electrophoretic behavior as the major U937 P-selectin ligand. Thus, E- and P-selectin recognize the same major glycoprotein ligand in U937 cells, a glycoprotein ligand immunoreactive with an anti-P-selectin ligand protein antibody and possessing the same apparent mass and electrophoretic behavior as full length, recombinant P-selectin ligand protein.

Fragments of the P-selectin ligand protein which are capable of interacting with P-selectin or which are capable of inhibiting P-selectin-mediated intercellular adhesion are also encompassed by the present invention. Such fragments comprise amino acids 21 to 54 of SEQ ID NO:2, a region of the P-selectin ligand protein having a low frequency of serine and threonine residues; amino acids 55 to 127 of SEQ ID NO:2, having a high frequency of proline, serine, and threonine in addition to two consensus sequences for asparagine-linked glycosylation (Asn-X-Ser/Thr); another larger fragment, amino acids 128 to 267 of SEQ ID NO:2, having both a high frequency of proline, serine, and threonine and containing fifteen repeats of the following ten amino acid consensus sequence: Ala-(Thr/Met)-Glu-Ala-Gln-Thr-Thr-(Pro/Arg/Gln/Ala/Glu)-(Leu/Pro)-(Ala/Thr) (smaller fragments within this large fragment may also retain the capacity to interact with P-selectin or act as inhibitors of P-selectin-mediated intercellular adhesion); the region containing a consensus sequence for asparagine-linked glycosylation and comprising amino acids 268 to 308 of SEQ ID NO:2; the hydrophobic region of the protein represented by amino acids 309 to 333 of SEQ ID NO:2; and the amphophilic region of the P-selectin ligand protein from amino acids 334 to 402 of SEQ ID NO:2. Additional fragments may comprise amino acid 43 to amino acid 56 of SEQ ID NO:2 or amino acid 42 to amino acid 60 of SEQ ID NO:2, with one or more sulfated or phosphorylated (Domcheck et al., Biochemistry 31:9865-9870 (1992)) tyrosines at amino acid 46, amino acid 48, and/or amino acid 51. Fragments of the P-selectin ligand protein may be in linear form or they may be cyclized using known methods, for example, as described in H. U. Saragovi, et al., BioTechnology 10, 773-778 (1992) and in R. S. McDowell, et al., J. Amer. Chem. Soc. 114, 9245-9253 (1992), both of which are incorporated herein by reference. For the purposes of the present invention, all references to "P-selectin ligand protein" herein include fragments capable of binding to P-selectin.

Such fragments may be fused to carrier molecules such as immunoglobulins, to increase the valency of P-selectin ligand binding sites. For example, soluble forms of the P-selectin ligand protein such as the fragments from amino acid 42 to amino acid 295 or from amino acid 42 to amino acid 88 of SEQ ID NO:2 may be fused through "linker" sequences to the Fc portion of an immunoglobulin (native sequence or mutated sequences for conferring desirable qualities (such as longer half-life or reduced immunogenicity) to the resulting chimera). For a bivalent form of the P-selectin ligand protein, such a fusion could be to the Fc portion of an IgG molecule as in Example 5(D) and in SEQ ID NO:6. Other immunoglobulin isotypes may also be used to generate such fusions. For example, a P-selectin ligand protein—IgM fusion would generate a decavalent form of the P-selectin ligand protein of the invention.

Fusions of any of the P-selectin ligand proteins of the present invention to amino acid sequences derived from other proteins may also be constructed. Preferred P-selectin ligand proteins for such purpose include the fragments from amino acid 42 to amino acid 295 or from amino acid 42 to amino acid 88 of SEQ ID NO:2. Desirable fusion proteins may incorporate amino acid sequence from proteins having a biological activity different from that of P-selectin ligand, such as, for example, cytokines, growth and differentiation factors (such as bone morphogenetic proteins (e.g., BMPs), hormones, enzymes, receptor components or fragments and other ligands. Also, P-selectin ligand protein can be chemically coupled to other proteins or pharmaceutical agents. In such usage, the P-selectin ligand protein, by virtue of the ability to interact with selectin molecules, alters the pharmacokinetics and/or biodistribution of the fused or coupled agent thereby enhancing its therapeutic efficacy. For example, fusion of a P-selectin ligand protein sequence to a cytokine sequence can direct the cytokine's activity to an area of inflammation. In such instance, the P-selectin ligand protein portion of the fusion protein will bind to selectins expressed at the site of inflammation. This binding will cause the cytokine portion of the fusion protein to become localized and available to bind its cognate receptor or any proximal cell surface. Other ligands could similarly be used in such fusions proteins to attract cells expressing their corresponding receptors to a site of P-selectin expression. Preferred examples of such fusions are described in Example 15.

In any fusion protein incorporating a P-selectin ligand protein, the amino acid sequence derived from a protein or proteins other than P-selectin ligand can be linked to either the C-terminus or N-terminus of the P-selectin ligand-derived sequence. The linkage may be direct (i.e., without an intervening linking sequence not derived from either protein) or through a linking sequence.

Methods of treating a mammalian subject using such fusion proteins are also contemplated by the present invention. In such instances, the fusion protein is used to treat a condition which is affected by the protein to which the P-selectin ligand protein is fused. For example, a fusion of a P-selectin ligand protein to IL-11 could be used to localize the activity of IL-11 to bone marrow endothelial cells which express selectins on their surface. Once localized, the IL-11 portion of the fusion protein will stimulate megakaryocyte progenitors. Similarly, a fusion of a P-selectin ligand protein to a BMP could be used to stimulate bone or cartilage formation in an area of injury. Injured tissues express P-selectin, which will bind the fusion protein. Once localized, the BMP portion of the fusion protein will stimulate bone or cartilage production in the area of injury.

As detailed in the Examples below, the P-selectin ligand protein of the invention was initially obtained using an expression cloning approach (Clark et al., U.S. Pat. No. 4,675,285). A cDNA library was constructed from the human promyelocytic cell line HL-60 (S. J. Collins, et al., Nature 270, 347-349 (1977), ATCC No. CCL 240). This library was cotransfected into COS cells with a DNA encoding a 3/4FT, and the cotransfectants were screened for binding to a chimeric molecule consisting of the extracellular portion of P-selectin and the Fc portion of a human IgGγ1 monoclonal antibody. Cotransfectants which bound to the chimeric P-selectin were enriched for cDNAs encoding the P-selectin ligand protein. This screening process was repeated several times to enrich the plasmid population further for cDNAs encoding the P-selectin ligand protein. In a second cloning stage, the enriched plasmid population was again cotransfected into COS cells with the 3/4FT gene and screened for binding to a fluorescently labeled CHO cell line which expressed P-selectin on the cell surface. A single cDNA clone was obtained from this approach and was designated pMT21: PL85. The pMT21:PL85 plasmid was deposited with the American Type Culture Collection on Oct. 16, 1992 and given the accession number ATCC 69096.

One novel DNA of the present invention is set forth in SEQ ID NO:1. The DNA of the present invention may encode a variety of forms of the P-selectin ligand protein. For example, in one embodiment, the DNA of the invention encodes the entire P-selectin ligand protein having the amino acid sequence set forth in SEQ ID NO:2 from amino acid 1 to amino acid 402. In another embodiment, the DNA of the invention encodes a form of the P-selectin ligand protein which lacks the signal sequence and which is characterized by the amino acid sequence set forth in SEQ ID NO:2 from amino acid 21 to amino acid 402. In yet another embodiment, the DNA of the invention encodes the mature P-selectin ligand protein characterized by the amino acid sequence set forth in SEQ ID NO:2 from amino acid 42 to amino acid 402. Another embodiment of the DNA of the invention encodes a soluble form of the P-selectin ligand protein characterized by the amino acid sequence set forth in SEQ ID NO:2 from amino acid 1 to amino acid 310. The DNA of the invention is also embodied in a DNA encoding a soluble form of the mature P-selectin ligand protein, said protein being characterized by the amino acid sequence set forth in SEQ ID NO:2 from amino acid 42 to amino acid 310. The DNA of the invention is further embodied in a DNA sequence encoding a soluble form of the P-selectin ligand protein which lacks the signal sequence, said protein being characterized by the amino acid sequence set forth in SEQ ID NO:2 from amino acid 21 to amino acid 310. The DNA of the present invention is free from association with other human DNAs and is thus characterized as an isolated DNA. As detailed above, DNAs which encode P-selectin ligand fragments which interact with P-selectin are also included in the present invention.

The expression of P-selectin ligand protein mRNA transcripts has been observed in a variety of human cell lines (HL-60, THP-1, U937) and in human monocytes and polymorphonuclear leukocytes by Northern analysis using a P-selectin ligand protein cDNA probe. In all of these cell lines, a major transcript of 2.5 kb was observed. A minor species of approximately 4 kb was observed in the HL60 and U937 cell lines and in polymorphonuclear leukocytes. In contrast, no P-selectin ligand mRNA expression was detected in the human hepatoblastoma cell line HepG2.

The P-selectin ligand protein of the invention is encoded by a single copy gene and is not part of a multi-gene family, as determined by Southern blot analysis. The genomic form of the P-selectin ligand protein of the invention contains a large intron of approximately 9 kb located at nucleotide 54 in the 5' untranslated region. In polymorphonuclear leukocytes and monocytes, the P-selectin ligand protein of the invention is encoded by the DNA sequence set forth in SEQ ID NO:3. In this embodiment, the P-selectin ligand protein contains sixteen repeat regions. The isolated DNA of the invention is correspondingly also embodied in the DNA sequence set forth in SEQ ID NO:3 and is contained on plasmid pPL85R16 which was deposited with the American Type Culture Collection on Oct. 22, 1993 and given the Accession Number ATCC 75577.

The invention also encompasses allelic variations of the isolated DNA as set forth in SEQ ID NO:1 or of the isolated DNA as set forth in SEQ ID NO:3, that is, naturally-occurring alternative forms of the isolated DNA of SEQ ID NO:1 or SEQ ID NO:3 which also encode proteins having P-selectin ligand activity. Also included in the invention are isolated DNAs which hybridize to the DNA set forth in SEQ ID NO:1 or to the DNA set forth in SEQ ID NO:3 under stringent (e.g. 4×SSC at 65° C. or 50% formamide and 4×SSC at 42° C.), or relaxed (4×SSC at 50° C. or 30-40% formamide at 42° C.) conditions, and which have P-selectin ligand protein activity. Isolated DNA sequences which encode the P-selectin ligand protein but which differ from the DNA set forth in SEQ ID NO:1 or from the DNA set forth in SEQ ID NO:3 by virtue of the degeneracy of the genetic code and which have P-selectin ligand protein activity are also encompassed by the present invention. Variations in the DNA as set forth in SEQ ID NO:1 or in the DNA as set forth in SEQ ID NO:3 which are caused by point mutations or by induced modifications which enhance the P-selectin ligand activity, half-life or production level are also included in the invention. For the purposes of the present invention all references herein to the "DNA of SEQ ID NO:1" include, in addition to DNAs comprising the specific DNA sequence set forth in SEQ ID NO:1, DNAs encoding the mature P-selectin ligand protein of SEQ ID NO:2; DNAs encoding fragments of the P-selectin ligand protein of SEQ ID NO:2 which are capable of binding to P-selectin; DNAs encoding soluble forms of the P-selectin ligand protein of SEQ ID NO:2; allelic variations of the DNA sequence of SEQ ID NO:1; DNAs which hybridize to the DNA sequence of SEQ ID NO:1 and which encode proteins having P-selectin ligand protein activity; DNAs which differ from the DNA of SEQ ID NO:1 by virtue of degeneracy of the genetic code; and the variations of the DNA sequence of SEQ ID NO:1 set forth above. Similarly, all references to the "DNA of SEQ ID NO:3" include in addition to the specific sequence set forth in SEQ ID NO:3, DNAs encoding the mature P-selectin ligand protein of SEQ ID NO:4; DNAs encoding fragments of the P-selectin ligand protein of SEQ ID NO:4 which are capable of binding to P-selectin; DNAs encoding soluble forms of the P-selectin ligand protein of SEQ ID NO:4; allelic variations of the DNA of SEQ ID NO:3; DNAs which hybridize to the DNA sequence of SEQ ID NO:3 and which encode proteins having P-selectin ligand protein activity; DNAs which differ from the DNA of SEQ ID NO:3 by virtue of degeneracy of the genetic code; and the variations of the DNA of SEQ ID NO:3 set forth above.

A DNA encoding a soluble form of the P-selectin ligand protein may be prepared by expression of a modified DNA in which the regions encoding the transmembrane and cytoplasmic domains of the P-selectin ligand protein are deleted and/or a stop codon is introduced 3' to the codon for the amino acid at the carboxy terminus of the extracellular domain. For example, hydrophobicity analysis predicts that the P-selectin ligand protein set forth in SEQ ID NO:2 has a transmembrane domain comprised of amino acids 311 to 332 of SEQ ID NO:2 and a cytoplasmic domain comprised of amino acids 333 to 402 of SEQ ID NO:2. A modified DNA as described above may be made by standard molecular biology techniques, including site-directed mutagenesis methods which are known in the art or by the polymerase chain reaction using appropriate oligonucleotide primers. Methods for producing several DNAs encoding various soluble P-selectin ligand proteins are set forth in Example 5.

A DNA encoding other fragments and altered forms of P-selectin ligand protein may be prepared by expression of modified DNAs in which portions of the full-length sequence have been deleted or altered. Substantial deletions of the P-selectin ligand protein sequence can be made while retaining P-selectin ligand protein activity. For example, P-selectin ligand proteins comprising the sequence from amino acid 42 to amino acid 189 of SEQ ID NO: 2, the sequence from amino acid 42 to amino acid 118 of SEQ ID NO: 2, or the sequence from amino acid 42 to amino acid 89 of SEQ ID NO: 2 each retain the P-selectin protein binding activity and the ability to bind to E-selectin. P-selectin ligand proteins in which one or more N-linked glycosylation sites (such as those at amino acids 65, 111 and 292 of SEQ ID NO: 2) have been changed to other amino acids or deleted also retain P-selectin protein binding activity and the ability to bind E-selectin. P-selectin ligand proteins comprising from amino acid 42 to amino acid 60 of SEQ ID NO:2 (which includes a highly anionic region of the protein from amino acid 45 to amino acid 58 of SEQ ID NO:2) also retain P-selectin ligand protein activity; however, P-selectin ligand proteins limited to such sequence do not bind to E-selectin. Preferably, a P-selectin ligand protein retains at least one (more preferably at least two and most preferably all three) of the tyrosine residues found at amino acids 46, 48 and 51 of SEQ ID NO: 2, sulfation of which may contribute to P-selectin ligand protein activity. Construction of DNAs encoding these and other active fragments or altered forms of P-selectin ligand protein may be accomplished in accordance with methods known to those skilled in the art.

The isolated DNA of the invention may be operably linked to an expression control sequence such as the pMT2 or pED expression vectors disclosed in Kaufman et al., Nucleic Acids Res. 19, 4485-4490 (1991), in order to produce the P-selectin ligand recombinantly. Many suitable expression control sequences are known in the art. General methods of expressing recombinant proteins are also known and are exemplified in R. Kaufman, Methods in Enzymology 185, 537-566 (1990). As defined herein "operably linked" means enzymatically or chemically ligated to form a covalent bond between the isolated DNA of the invention and the expression control sequence, in such a way that the P-selectin ligand protein is expressed by a host cell which has been transformed (transfected) with the ligated DNA/expression control sequence.

Several endoproteolytic enzymes are known which cleave precursor peptides at the carboxyl side of paired amino acid sequences (e.g., -Lys-Arg- and -Arg-Arg-) to yield mature proteins. Such enzymes are generally known as paired basic amino acid converting enzymes or PACE, and their use in recombinant production of mature peptides is extensively disclosed in WO 92/09698 and U.S. application Ser. No. 07/885,972, both of which are incorporated herein by reference. The PACE family of enzymes are known to increase the efficiency of proteolytic processing of precursor polypeptides in recombinant host cells. As mentioned above, the P-selectin ligand protein of the invention contains such a PACE cleavage site.

The soluble mature P-selectin ligand protein of the present invention may be made by a host cell which contains a DNA sequence encoding any soluble P-selectin ligand protein as described herein and a DNA sequence encoding PACE as described in WO 92/09698 and U.S. application Ser. No. 07/885,972, incorporated herein by reference, or using the DNA sequence of SEQ ID NO:5. Such a host cell may contain the DNAs as the result of co-transformation or sequential transformation of separate expression vectors containing the soluble P-selectin ligand protein DNA and the PACE DNA, respectively. A third DNA which encodes a 3/4FT may also be co-transformed with the DNAs encoding the P-selectin ligand protein and PACE. Alternatively, the host cell may contain the DNAs as the result of transformation of a single expression vector containing both soluble P-selectin ligand protein DNA and PACE DNA. Construction of such expression vectors is within the level of ordinary skill in molecular biology. Methods for co-transformation and transformation are also known.

Many DNA sequences encoding PACE are known. For example, a DNA encoding one form of PACE, known as furin, is disclosed in A. M. W. van den Ouweland et al., Nucl. Acids Res. 18, 664 (1990), incorporated herein by reference. A cDNA encoding a soluble form of PACE, known as PACE-SOL, is set forth in SEQ ID NO:5. DNAs encoding other forms of PACE also exist, and any such PACE-encoding DNA may be used to produce the soluble mature P-selectin ligand protein of the invention, so long as the PACE is capable of cleaving the P-selectin ligand protein at amino acids 38-41.

Preferably, a DNA encoding a soluble form of PACE is used to produce the soluble mature P-selectin ligand protein of the present invention.

The DNAs encoding a soluble form of the P-selectin ligand protein and PACE, separately or together, may be operably linked to an expression control sequence such as those contained in the pMT2 or pED expression vectors discussed above, in order to produce the PACE-cleaved soluble P-selectin ligand recombinantly. Additional suitable expression control sequences are known in the art. Examples 3(C) and 3(D) below set forth methods for producing the soluble mature P-selectin ligand protein of the invention.

A number of types of cells may act as suitable host cells for expression of the P-selectin ligand protein. Suitable host cells are capable of attaching carbohydrate side chains characteristic of functional P-selectin ligand protein. Such capability may arise by virtue of the presence of a suitable glycosylating enzyme within the host cell, whether naturally occurring, induced by chemical mutagenesis, or through transfection of the host cell with a suitable expression plasmid containing a DNA sequence encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The P-selectin ligand protein may also be produced by operably linking the isolated DNA of the invention and one or more DNAs encoding suitable glycosylating enzymes to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. Soluble forms of the P-selectin ligand protein may also be produced in insect cells using appropriate isolated DNAs as described above. A DNA encoding a form of PACE may further be co-expressed in an insect host cell to produce a PACE-cleaved form of the P-selectin ligand protein.

Alternatively, it may be possible to produce the P-selectin ligand protein in lower eukaryotes such as yeast or in prokaryotes such as bacteria. Potentially suitable yeast strains include *Saccharomyces cerevisiae, Schizosaccharomyces pombe, Kluyveromyces* strains, *Candida,* or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the P-selectin ligand protein is made in yeast or bacteria, it is necessary to attach the appropriate carbohydrates to the appropriate sites on the protein moiety covalently, in order to obtain the glycosylated P-selectin ligand protein. Such covalent attachments may be accomplished using known chemical or enzymatic methods.

The P-selectin ligand protein of the invention may also be expressed as a product of transgenic animals, e.g., as a component of the milk of transgenic cows, goats, pigs, or sheep which are characterized by somatic or germ cells containing a DNA sequence encoding the P-selectin ligand protein.

The P-selectin binding activity of a P-selectin protein may be enhanced by co-transformation of a host cell with a GlcNAc transferase, preferably UDP-GlcNAc:Gal β1-3Gal-NAc-R(GlcNAc to GalNAc)β1-6 GlcNAc transferase (EC 2.4.1.102), also known as "core2 transferase."

O-linked glycans present on P-selectin ligand protein have been shown to be important for binding to P-selectin (D. Sako et al., Cell 75, 1179-1186 (1993)). It has been reported that sialyl Le$^x$ on O-linked glycans of myeloid cells are presented on complex, branched structures (Maemura, K. and Fukuda, M., J. Biol. Chem. 267, 24379-24386 (1992)). The enzyme responsible for generating such oligosaccharide structures is "core2". The core2 enzyme activity is found at very low levels in COS cells and at trace levels in CHO cells. Host cells co-transformed with DNAs encoding a P-selectin ligand protein, an (α1,3/α1,4) fucosyltransferase and core2 can produce P-selectin ligand protein exhibiting 20-30 fold enhanced binding to P-selectin.

In certain preferred embodiments, P-selectin ligand protein is produced by co-transfecting a host cell with DNAs encoding soluble P-selectin ligand protein, 3/4FT, core2 and PACE.

The P-selectin ligand protein of the invention may be prepared by culturing transformed host cells under culture conditions necessary to express a P-selectin binding glycoprotein. The resulting expressed glycoprotein may then be purified from culture medium or cell extracts. Soluble forms of the P-selectin ligand protein of the invention can be purified by affinity chromatography over Lentil lectin-Sepharose® and subsequent elution with 0.5M α-methyl-mannoside. The eluted soluble P-selectin ligand protein can then be further purified and concentrated by a 0-70% ammonium sulfate precipitation step. The protein is then recovered, resuspended, and further purified by size exclusion chromatography over a TSK G4000SW$_{XL}$. Alternatively, full length forms of the P-selectin ligand protein of the invention can be purified by preparing a total membrane fraction from the expressing cell and extracting the membranes with a non-ionic detergent such as Triton X-100. The detergent extract can then be passed over an affinity column comprised of immobilized P-selectin, and the P-selectin ligand protein can be eluted from the column with 10 mM EDTA in a buffer containing 0.1% detergent. The material eluted from the affinity column can then be dialyzed to remove EDTA and further purified over a Lentil lectin-Sepharose® affinity column again eluting with 0.5M α-methyl-mannoside.

Alternatively, the P-selectin ligand protein of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the P-selectin ligand protein from culture supernatant may also include one or more column steps over such affinity resins as concanavalin A-agarose, Heparin-Toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the P-selectin ligand protein. Some or all of the foregoing purification steps, in various combinations, can also be employed to provide a substantially homogeneous isolated recombinant protein. The P-selectin ligand protein thus purified is substantially free of other mammalian proteins and is defined in accordance with the present invention as "isolated P-selectin ligand protein".

Isolated P-selectin ligand protein may be useful in treating conditions characterized by P-, E- or L-selectin mediated intercellular adhesion. Such conditions include, without limitation, myocardial infarction, bacterial or viral infection, metastatic conditions, inflammatory disorders such as arthritis, gout, uveitis, acute respiratory distress syndrome, asthma, emphysema, delayed type hypersensitivity reaction, systemic lupus erythematosus, thermal injury such as burns or frostbite, autoimmune thyroiditis, experimental allergic encephalomyelitis, multiple sclerosis, multiple organ injury syndrome secondary to trauma, diabetes, Reynaud's syndrome, neutrophilic dermatosis (Sweet's syndrome), inflammatory bowel disease, Grave's disease, glomerulonephritis, gingivitis, periodontitis, hemolytic uremic syndrome, ulcerative colitis, Crohn's disease, necrotizing enterocolitis, granulocyte transfusion associated syndrome, cytokine-induced toxicity, and the like Isolated P-selectin ligand protein may also be useful in organ transplantation, both to prepare organs for transplantation and to quell organ transplant rejection. Accordingly, P-selectin ligand protein may be administered to a living or non-living organ donor, prior to organ removal. In addition, P-selectin ligand protein may be administered "ex-vivo" to the donor organ concomitantly with organ preservation solution, prior to, and/or subsequent to surgical anastomosis with the recipient. Isolated P-selectin ligand protein may be used to treat hemodialysis and leukophoresis patients. Additionally, isolated P-selectin ligand protein may be used as an antimetastatic agent. Isolated P-selectin ligand protein may be used itself as an inhibitor of P-, E- or L-selectin-mediated intercellular adhesion or to design inhibitors of P-, E- or L-selectin-mediated intercellular adhesion. The present invention encompasses both pharmaceutical compositions containing isolated P-selectin ligand protein and therapeutic methods of treatment or use which employ isolated P-selectin ligand protein.

Isolated P-selectin ligand protein, purified from cells or recombinantly produced, may be used as a pharmaceutical composition when combined with a pharmaceutically acceptable carrier. Such a composition may contain, in addition to P-selectin ligand protein and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, G-CSF, Meg-CSF, stem cell factor, and erythropoietin. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated P-selectin ligand protein, or to minimize side effects caused by the isolated P-selectin ligand protein. Conversely, isolated P-selectin ligand protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated P-selectin ligand protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., healing of chronic conditions characterized by P-selectin- or E-selectin-mediated cellular adhesion or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated P-selectin ligand protein is administered to a mammal having a P-selectin-mediated disease state. Isolated P-selectin ligand protein may be administered in accordance with the method of the invention either alone or in combination with other therapies such as treatments employing receptor antagonists, ligand antagonists, cytokines, lymphokines or other hematopoietic factors. When co-administered with one or more cytokines, lymphokines or other hematopoietic factors, isolated P-selectin ligand protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated P-selectin ligand protein in combination with cytokine(s), lymphokine(s), other hematopoietic factor(s), thrombolytic or anti-thrombotic factors.

Administration of isolated P-selectin ligand protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated P-selectin ligand protein is administered orally, isolated P-selectin ligand protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated P-selectin ligand protein, and preferably from about 25 to 90% isolated P-selectin ligand protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated P-selectin ligand protein and preferably from about 1 to 50% isolated P-selectin ligand protein.

When a therapeutically effective amount of isolated P-selectin ligand protein is administered by intravenous, cutaneous or subcutaneous injection, isolated P-selectin ligand protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated P-selectin ligand protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of isolated P-selectin ligand protein in the pharmaceutical composition of the present invention will depend upon the nature and severity of the condition being treated, and on the nature of prior treatments which the patient has undergone. Ultimately, the attending physician will decide the amount of isolated P-selectin ligand protein with which to treat each individual patient. Initially, the attending physician will administer low doses of isolated P-selectin ligand protein and observe the patient's response. Larger doses of isolated P-selectin ligand protein may be administered until the optimal therapeutic effect is obtained for the patient, and at that point the dosage is not increased further. It is contemplated that the various pharmaceutical compositions used to practice the method of the present invention should contain about 0.1 µg to about 100 mg of isolated P-selectin ligand protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated P-selectin ligand protein will be in the range of 12 to 24 hours of continuous intravenous administration. Ultimately the attending physician will decide on the appropriate duration of intravenous therapy using the pharmaceutical composition of the present invention.

Isolated P-selectin ligand protein of the invention may also be used to immunize animals to obtain polyclonal and monoclonal antibodies which specifically react with the P-selectin ligand protein and which may inhibit P-selectin-mediated cellular adhesion. Such antibodies may be obtained using the entire P-selectin ligand protein as an immunogen, or by using fragments of P-selectin ligand protein such as the soluble mature P-selectin ligand protein. Smaller fragments of the P-selectin ligand protein may also be used to immunize animals, such as the fragments set forth below: amino acid 42 to amino acid 56 of SEQ ID NO:2 and amino acid 127 to amino acid 138 of SEQ ID NO:2. An additional peptide immunogen comprises amino acid 238 to amino acid 248 of SEQ ID NO:2, with an alanine residue added to the amino terminus of the peptide. Another peptide immunogen comprises amino acid 43 to amino acid 56 of SEQ ID NO:2 having a sulfated tyrosine in any or all of positions 46, 48 or 51. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149-2154 (1963); J. L. Krstenansky, et al., FEBS Lett. 211, 10 (1987).

Monoclonal antibodies binding to P-selectin ligand glycoprotein or to complex carbohydrate moieties characteristic of the P-selectin ligand glycoprotein may be useful diagnostic agents for the immunodetection of inflammatory diseases and some forms of cancer. Some cancerous cells, such as small cell lung carcinomas, may express detectable levels of the P-selectin ligand protein. This abnormal expression of the P-selectin ligand protein by cancer cells may play a role in the metastasis of these cells.

Neutralizing monoclonal antibodies binding to P-selectin ligand glycoprotein or to complex carbohydrates characteristic of P-selectin ligand glycoprotein may also be useful therapeutics for both inflammatory diseases and also in the treatment of some forms of cancer where abnormal expression of P-selectin ligand protein is involved. These neutralizing monoclonal antibodies are capable of blocking the selectin mediated intercellular adherence function of the P-selectin ligand protein. By blocking the binding of P-selectin ligand protein, the adherence of leukocytes to sites of inappropriate inflammation is either abolished or markedly reduced. In the case of cancerous cells or leukemic cells, neutralizing monoclonal antibodies against P-selectin ligand protein may be useful in detecting and preventing the metastatic spread of the cancerous cells which may be mediated by the P-selectin ligand protein. In addition, the monoclonal antibodies bound to these cells may target the cancerous cells for antibody-dependent cell medicated cytoxicity (ADCC), thus helping to eliminate the cancerous cells. Human antibodies which react with the P-selectin ligand protein may be produced in transgenic animals which contain human immunoglobulin encoding genes in their germ lines. Example 7 below sets forth production of a rabbit polyclonal antibody specific P-selectin ligand protein fragments.

P-selectin ligand protein of the invention may also be used to screen for agents which are capable of binding to P-selectin ligand protein and thus may act as inhibitors of P-selectin- or E-selectin-mediated intercellular adhesion. Binding assays using a desired binding protein, immobilized or not, are well known in the art and may be used for this purpose using the P-selectin ligand protein of the invention. Appropriate screening assays may be cell-based, as in Examples 3 and 9 below. Alternatively, purified protein based screening assays may be used to identify such agents. For example, P-selectin ligand protein may be immobilized in purified form on a carrier and binding to purified P-selectin may be measured in the presence and in the absence of potential inhibiting agents. A suitable binding assay may alternatively employ purified P-selectin immobilized on a carrier, with a soluble form of P-selectin ligand protein of the invention.

Any P-selectin ligand protein may be used in the screening assays described above. For example, the full-length P-selectin ligand protein set forth in SEQ ID NO:2 from amino acid 1 to amino acid 402 may be used to screen for inhibitors; or the mature P-selectin ligand protein set forth in SEQ ID NO:2 from amino acid 42 to amino acid 402 may be used to screen for inhibitors, or the soluble mature P-selectin ligand protein set forth in SEQ ID NO:2 from amino acid 42 to amino acid 310 may be used to screen for inhibitors. Alternatively, the P-selectin ligand protein of SEQ ID NO:4 from amino acid 1 to amino acid 412, or a mature form of the P-selectin ligand protein as set forth in SEQ ID NO:4 from amino acid 42 to amino acid 412, or a soluble mature form of the P-selectin ligand protein set forth in SEQ ID NO:4 from amino acid 42 to amino acid 320 may be used to screen for inhibitors of intercellular adhesion in accordance with the present invention.

In such a screening assay, a first binding mixture is formed by combining P-selectin or E-selectin and P-selectin ligand protein, and the amount of binding in the first binding mixture ($B_o$) is measured. A second binding mixture is also formed by combining P-, E- or L-selectin, P-selectin ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting P-, E- or L-selectin mediated intercellular adhesion if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention.

Compounds found to reduce by at least about 10%, preferably greater than about 50% or more of the binding activity of P-selectin ligand protein to P-, E- or L-selectin may thus be identified and then secondarily screened in other selectin binding assays, including assays binding to L-selectin and in vivo assays. By these means compounds having inhibitory activity for selectin-mediated intercellular adhesion which may be suitable as anti-inflammatory agents may be identified.

EXAMPLE 1

Cloning of the P-Selectin Ligand Protein Gene

A. Construction of the HL60 cDNA library

An HL60 cDNA library was constructed for expression cloning the P-selectin ligand. PolyA$^+$ RNA was isolated from total RNA from the human promyelocytic cell line HL60 (S. J. Collins, et al., supra) using a Fast Track mRNA Isolation Kit (Invitrogen; San Diego, Calif.). Double stranded cDNA was synthesized from the polyA$^+$ RNA fraction and blunt-end ligated with EcoRI adaptors (5'-AATTCCGTCGACTCTA-GAG-3', SEQ ID NO:7; 5'-CTCTAGAGTCGACGG-3', SEQ ID NO:8). The cDNA was ligated into the expression vector pMT21 (R. Kaufman et al., J. Mol. Cell. Biol. 9, 946-958 (1989) that had been incubated sequentially with EcoRI endonuclease and calf intestinal alkaline phosphatase and gel purified. The ligation product was electroporated in 2 µl aliquots into competent E. coli DH5α cells and grown in 1 ml of SOB medium (J. Sambrook et al., *Molecular Cloning: A Laboratory Manual,* New York, Cold Spring Harbor Laboratory Press, p 1.90 (1989)) which has been supplemented with 10 mM MgCl$_2$, 10 mM MgSO$_4$, and 2% glycerol for one hour at 37° C. In order to divide the library into smaller subsets, an aliquot from each ml of bacterial suspension was plated onto agar plates in the presence of ampicillin, and the number of colonies per ml was calculated. Assuming that each colony represented one cDNA clone, 600,000 clones were generated and divided into subsets of approximately 16,000 clones per pool. Each of the 38 pools were grown overnight in L-broth in the presence of ampicillin and the plasmids were purified over a CsCl gradient.

B. Screening for the P-Selectin Ligand Protein Gene

In the first stage, the LEC-γ1 binding assay of Example 4(A) was utilized to pan the HL60 cDNA library and thereby to enrich for the plasmid of interest. Six µg of each HL60 cDNA library pool was co-transfected with 2 µg of α3/4FT gene (Example 2) into COS cells. Approximately 45 hours post-transfection, the COS cells were lifted from the plates by incubating the cells in 1 mM EGTA for 15 min. at 37° C., followed by scraping with cell lifters. The cells were washed twice in Hanks buffered saline solution containing 1 mM calcium (HBSS). The cells were resuspended in 4 ml of HBSS. The resuspended transfected COS cells were screened using the LEC-γ1 binding assay described in Example 4(A).

The plasmids from adherent COS cells were recovered from a Hirts extract [B. Hirts, J. Mol. Biol., 26, 365-369 (1967)] and then electroporated into E. coli DH5α cells for amplification. The enriched population of plasmids was purified over a CsCl gradient and re-transfected along with the 3/4FT gene (Example 2) into COS cells. The transfection, screening, and plasmid amplification process was repeated for a total of three times before a pool that bound to the LEC-γ1-coated plates was visually detected. The positive plasmid pool was subsequently broken down into subsets. This involved electroporating the Hirts extract from the positive pool into E. coli DH5α cells and quantitating colonies per ml as described above. Various pool sizes were produced by plating out a predetermined number of colonies on agar plates in the presence of ampicillin. Duplicate plates were prepared by performing nitrocellulose lifts and storing the filters on new agar plates. The duplicate plates served as reference plates for selecting individual or groups of colonies from any pool identified as being positive.

In the second stage of cloning, COS cells were co-transfected with the sublibrary pools and the 3/4FT gene by the same procedure used in the initial steps of screening. Forty-eight hours post-transfection, the transfected cells were screened using the fluorescent CHO:P-selectin assay of Example 4(B). Positive pools were further subdivided, as described above, until finally individual colonies were screened and positive clones identified. Using this method, a single positive clone, pMT21:PL85, was found to encode the P-selectin ligand protein. The DNA sequence of the P-selectin ligand contained in pMT21:PL85 is set forth in SEQ ID NO:1, and the binding characteristics of the P-selectin ligand protein encoded by pMT21:PL85 are set forth in Example 4(C) below.

EXAMPLE 2

Cloning the α1,3/1,4 Fucosyltransferase Gene

The α1,3/1,4 fucosyltransferase gene (3/4FT) was cloned from total human genomic DNA (Clontech Laboratories) by means of PCR. The sense oligonucleotide primer contained an XbaI site and the 5' terminus of the gene (5'-TAGCAT-ACGCTCTAGAGCATGGATCCCCTGGGTG-CAGCCAAGC-3', SEQ ID NO:9), and the antisense oligonucleotide primer contained an EcoRI site and the 3' terminus of the gene (5'-CCGGAATTCTCAGGTGAACCAAGC-CGC-3', SEQ ID NO:10). The PCR product was sequentially digested with XbaI and EcoRI and purified by standard gel purification methods. This gene was then ligated with vector pMT3 Sv2ADA (R. Kaufman, Methods in Enzymology, supra) that had also been sequentially digested with XbaI and EcoRI and purified by standard gel purification methods. Competent HB11 cells (Biorad) were transformed with this ligation product and then plated on agar plates in the presence of ampicillin. Nitrocellulose filter lifts of ampicillin-resistant transformants were probed with a radiolabelled oligonucleotide (5'-AAGTATCTGTCCAGGGCTTCCAGGT-3', SEQ ID NO:11) complementary to the nucleotide region 506-530 in the middle of the gene (J. Sambrook et al., supra).

Plasmid DNA minipreps were prepared from twelve positive clones. The purified DNA was then digested with EcoRI and XbaI to identify the correct clone with the proper size insert. This clone (pEA.3/4FT) was then grown up large scale and the DNA isolated by CsCl density gradient banding (J. Sambrook et al., supra). DNA sequencing confirmed the identity of the 3/4FT gene. The functionality of the gene was assessed in a cell-cell binding assay as follows. COS-1 monkey cells [(clone M6; M. Horwitz et al., Mol. Appl. Genet., 2:147-149, (1983)] were transfected with 3/4FT using DEAE dextran followed by DMSO shock treatment and chloroquine incubation [L. Sompeyrac and K Dana, Proc. Natl. Acad. Sci., 78:7575-7578 (1981); M. Lopata et al., Nucleic Acids Res., 12:5707-5717, (1984); H. Luthman and G. Magnuson, Nucleic Acids Res., 11:1295-1308, (1983)]. The transfected COS cells were suspended and quantitated for binding to a CHO line expressing E-selectin [G. Larsen et al., J. Biol. Chem. 267:11104-11110, (1992)]. This assay confirmed that the COS cells transfected with 3/4FT can express the sialylated Lewis$^x$ epitope on the cell surface.

EXAMPLE 3

Expression of the P-Selectin Ligand Protein

A. Expression of the P-Selectin Ligand in LEC11 Cells

Functional P-selectin ligand was expressed in the SLe$^x$-positive Chinese hamster ovary (CHO) cell line LEC11 (Campbell, C. and Stanley, P. Cell 35:303-309 (1983) as follows: approximately 8 µg of plasmid containing the P-selectin ligand gene (pMT21:PL85, Example 1) was transfected into LEC11 cells. At 68 hours post-transfection, the cells were treated with 2.5 mM sodium butyrate for 4 hours. The cells were observed to induce P-selectin adhesion, as determined using the 6-CFD labeled CHO:P-selectin cell binding assay (described in Example 4, section B). In contrast, neither LEC11 cells alone nor LEC11 cells transfected with a control plasmid induced P-selectin adhesion.

B. Expression of Soluble P-Selectin Ligand in COS Cells

COS cells were transfected with 8 µg pED.sPSL.T7 (see Example 5C) and 4 µg pEA.3/4 FT plasmid of Example 2, 8 µg pED.sPSL.T7 alone, or 8 µg plasmid vector (pMT21) and 4 µg pEA.3/4 FT gene. Forty-five hr post-transfection, the cells were rinsed twice in PBS and incubated overnight at 37° C. in serum-free DMEM minus phenol red (JRH Biosciences) supplemented with 2 mM L-glutamine, 100 U/ml penicillin and 100 µg/ml streptomycin. Phenylmethylsulfonyl fluoride, aprotinin and NaN$_3$ were added to final concentrations of 1 mM, 2 µg/ml and 0.02%, respectively, and the conditioned medium was centrifuged to remove all debris.

For immunoprecipitation experiments, the labeled soluble P-selectin ligand protein was produced by co-transfecting COS cells with pED.sPSL.T7 and pEA.3/4 FT. At forty-five hr post-transfection, the COS cells were labeled with 250 µCi/ml $^{35}$S methionine (NEN) for 5 hours and the medium was collected. Expression of sPSL.T7 protein was confirmed by immunoprecipitation with anti-T7 antibodies.

C. Expression of PACE-Cleaved P-Selectin Ligand in COS Cells

COS cells were co-transfected with the pED.sPSL.T7 plasmid of Example 5(C), the pEA.3/4FT cDNA of Example 2, and a plasmid containing the PACE cDNA as set forth in SEQ ID NO:5. A parallel control co-transfection was done using only the pED.sPSL.T7 plasmid and the pEA.3/4FT plasmid. After 45 hours, conditioned medium from these transfected COS cells was coated onto plastic dishes and binding to CHO:P-selectin cells (Example 4) was determined. An approximately two-fold increase in bound CHO:P-selectin cells was observed for dishes coated with medium containing the P-selectin ligand co-expressed with PACE, as compared with medium containing P-selectin ligand which had not been co-expressed with PACE. Amino acid sequencing of the N-terminus of purified sPSL.T7 protein from the PACE co-transfection showed that all of the ligand had been cleaved at the PACE consensus site (amino acids 38-41 of SEQ ID NO:1). Radiolabelling of co-transfected COS cells with $^{35}$S-methionine and subsequent SDS-polyacrylamide gel electrophoresis and autoradiography showed that comparable quantities of the P-selectin ligand had been secreted in both co-transfections.

D. Expression of the P-Selectin Ligand Protein in CHO Cells

A full-length form (amino acids 1-402) of the P-selectin ligand protein was expressed in the CHO(DUKX) cell line (Urlaub & Chasin, Proc. Natl. Acad. Sci. USA 77, 4216-4220 (1980)) as follows: approximately 25 µg of the pMT21:PL85 plasmid and approximately 8 µg of the pED.3/4FT (produced by restriction of pEA.3/4FT with EcoRI and XbaI and insertion of the resulting fragment into the pED plasmid) were co-transfected into CHO(DUKX) cells using the calcium phosphate method. Transfectants were selected for resistance to methotrexate. After two weeks, individual colonies were screened for SLe$^x$ expression by using a conjugate of an anti SLe$^x$ antibody (CSLEX-1, U.S. Pat. No. 4,752,569) and sheep red blood cells (sRBC) prepared by the chromic chloride method (Goding, J. W., J. Immunol. Methods 10:61-66 (1976) as follows: sRBC were washed with 0.15M NaCl until the wash became clear and then a 50% suspension of sRBC was prepared in 0.15M Nacl. One ml of 0.01% chromic chloride solution was added dropwise while vortexing to 0.2 ml of a sRBC suspension containing 50 µg of CSLEX-1. After incubating at 37° C. for 30 minutes, 10 ml of phosphate buffered saline (PBS) solution was added to the reaction. The conjugate was washed once before resuspending into 10 ml of PBS. The plates containing transfectants were washed with PBS and then 3 ml of PBS and one ml of the sRBC/CSLEX-1 conjugate was added to each plate. Positive colonies were red on a transilluminator and were picked into alpha medium with 10% fetal bovine serum. After two weeks, colonies were subjected to stepwise amplification using methotrexate at concentrations of 2, 10, 25, 100, 250 nM. The stable cell line obtained was designated CD-PSGL-1 (R3.4). Expression of the P-selectin ligand protein was confirmed by immunoprecipitation studies using the polyclonal anti-P-selectin ligand protein antibody of Example 7(A). The functionality of the P-selectin ligand protein produced by the CD-PSGL-1 (R3.4) cell line was tested by assaying the transfectants for binding to LEC-γ1 as in Example 4(A).

The sPSL.T7 protein was expressed in a stable CHO-PACE line which was already expressing the cDNA encoding PACE as set forth in SEQ ID NO:5 under adenosine deaminase selection (Kaufman, et al., PNAS (USA) 83:3136-3140 (1986)). The psPSL.T7 (25 µg) and pED.3/4FT (8 µg) plasmids were cotransfected into CHO-PACE cells using the calcium phosphate method. Transfectants were selected for resistance to methotrexate, and individual colonies which bound to the sRBC/CSLEX-1 conjugate were picked. After two weeks in culture, the colonies were subjected to stepwise amplification as described above. The stable cell line obtained was designated CP/PSL-T7 (R4.1). Expression of sPSL.T7 protein was confirmed by standard immunoprecipitation methods using either a T7 specific monoclonal antibody or the LEC-γ1 chimera of Example 4(A). In a similar fashion, a stable cell line expressing the mature full length form (amino acids 42-402) of the P-selectin ligand protein was obtained by co-transfection of pMT21:PL85 and pED.314FT into the CHO-PACE line.

Stable cell lines expressing the sPSL.Q protein of Example 5(B) and the sPSL.Fc protein of Example 5(D) were constructed as follows: plasmids pED.sPSL.Q (25 µg) or pED-.sPSL.Fc (25 µg) were cotransfected with approximately 25 µg of the pED.3/4FT plasmid described above and approximately 20 µg of a plasmid containing the PACE cDNA as set forth in SEQ ID NO:5) as well as the neomycin resistance gene into CHO(DUKX) cells using the calcium phosphate method. Transfectants were selected for resistance to methotrexate and the G418 antibiotic. Approximately two weeks later, individual colonies were screened for SLe$^x$ expression using sRBC/CSLEX-1 conjugate binding. The positive colonies were picked in G418 medium at 1 mg/ml concentration. After 2-3 weeks in culture, cells were amplified with methotrexate in a stepwise selection. The stable cell lines obtained were designated CD-sPSL.Q (R8.2) and CD-sPSL.Fc (R8.1), respectively. The expression of sPSL.Q and sPSL.Fc protein was confirmed by standard immunoprecipitation method using the anti P-selectin ligand protein polyclonal antibody of Example 7(A).

EXAMPLE 4

Assays of P-Selectin-Mediated Intercellular Adhesion

A. LEC-γ1 Binding Assay

A DNA encoding a chimeric form of P-selectin conjugated to the Fc portion of a human IgGγ1 (LEC-γ1) was constructed using known methods (Aruffo et al. Cell 67, 3544 (1991)), and stably transfected into dhfr CHO cells (CHO DUKX) for high level production of the chimeric LEC-γ1 protein, which was purified for use in the binding assay set forth below.

Petri dishes were coated first with a polyclonal anti-human IgGγ1 Fc antibody and then with LEC-γ1. This method orients the LEC-γ1 construct such that the P-selectin portion of the chimeric molecule is presented on the surface of the plates. Adhesion of HL60 cells to the oriented LEC-γ1 was quantitated in the presence and absence of calcium. HL60 adhesion was shown to be calcium dependent, confirming that the chimeric molecule had retained functional binding of P-selectin to its ligand on HL60 cells. The binding of HL60 cells to oriented LEC-γ1 was also shown to be blocked by a neutralizing monoclonal antibody to P-selectin, demonstrating the specificity of P-selectin binding.

B. Fluorescent CHO-P-Selectin Binding Assay

The assay employed a fluorescently labeled CHO:P-selectin cell line (Larsen et al., J. Biol. Chem. 267, 11104-11110 (1992)) that can bind to and form clusters on the surface of COS cells that are co-transfected with the P-selectin ligand gene and the 3/4 FT gene. The CHO:P-selectin cells were suspended at $1.5 \times 10^6$ cells/ml in 1% fetal bovine serum in DME medium and labeled by adding 6-carboxyfluorescein diacetate (6-CFD) to a final concentration of 100 ug/ml. After incubation at 37° C. for 15 minutes, the cells were washed in medium and resuspended at $1 \times 10^5$ cells/ml. Five ml of the labeled cells were added to each washed COS transfectant-containing plate to be assayed and incubated at room temperature for 10 minutes. Nonadherent cells were removed by four washes with medium. The plates were then scanned by fluorescence microscopy for rosettes of adherent CHO:P-selectin cells.

C. Quantitative Adhesion Assay using Radioactively Labeled CHO:P-Selectin Cells

COS cells were co-transfected with the pMT21:PL85 plasmid of Example 1 and the pEA.3/4FT plasmid of Example 2 by the same procedure used in the initial stages of screening. As controls, COS cells were transfected with pMT21:PL85 alone, or with pEA.3/4FT alone, or with a similar plasmid containing no insert ("mock"). 24 hours post-transfection, the transfected cells were trypsinized and distributed into Costar 6-well tissue culture plates. CHO:P-selectin cells were labeled for 16 hours with $^3$H-thymidine using known methods and preincubated at $0.5 \times 10^6$ cells/ml for 30 minutes at 4° C. in α medium containing 1% BSA (control); α medium containing 1% BSA, 5 mM EDTA and 5 mM EGTA; α medium containing 1% BSA and 10 µg/ml of a neutralizing anti P-selectin monoclonal antibody; and α medium containing 1% BSA and a non-neutralizing anti-P-selectin monoclonal antibody. The preincubated cells were then added to the wells containing the transfected COS cells. After a 10 minute incubation, unbound cells were removed by 4 changes of medium. The bound CHO:P-selectin cells were released by trypsinization and quantified by scintillation counting.

COS cells co-transfected with P-selectin ligand and the 3/4FT induced approximately 5.4-fold more binding of CHO:P-selectin cells relative to COS mock cells; assay in the presence of EGTA and EDTA reduced binding to the level of the mock transfected COS cells. Likewise, incubation with neutralizing anti-P-selectin antibody also eliminated specific binding, whereas non-neutralizing antibody had no effect. In contrast, the binding of CHO:P-selectin to COS cells transfected with P-selectin ligand alone was not statistically different than binding to the mock-transfected COS in both the presence or absence of EDTA and EGTA, or anti-P-selectin antibodies. The binding of CHO:P-selectin cells to COS cells transfected with 3/4 FT alone was approximately 2-fold greater than to the mock-transfected COS, but was unaffected by the presence or absence of EDTA and EGTA.

EXAMPLE 5

Construction of Soluble P-Selectin Ligands

The EcoRI adaptors used to generate the cDNA library from HL60 cells in Example I contain an XbaI restriction site (TCTAGA) just 5' of the beginning of SEQ ID NO:1 as it is located in the pMT21:PL85 plasmid. In order to generate soluble forms of the PSL, the pMT21:PL85 plasmid was restricted with XbaI and with HincII (which cleaves after nucleotide 944 of SEQ ID NO:1). The approximately 950 bp fragment thus generated, containing all of the encoded extracellular segment of the ligand up to and including the codon for valine 295, was isolated and used to generate DNAs encoding soluble forms of the P-selectin ligand protein as set forth in sections A though D below.

A. Construction of psPSL.QC

The fragment was purified and ligated into mammalian expression vector pED between the XbaI and EcoRI sites, along with double stranded synthetic oligonucleotide DNA that recreated the codons from Asn 296 to Cys 310 and introduced a novel stop codon immediately following Cys 310. The sequence of the oligos is as follows:

```
                                              (SEQ ID NO: 12)
5'-AACTACCCAGTGGGAGCACCAGACCACATCTCTGTGAAGCAGTGCTAG (SEQ ID NO: 13)
5'-AATTCTAGCACTGCTTCACAGAGATGTGGTCTGGTGCTCCCACTGG
TAGTT
```

The resulting plasmid was designated pED.sPSL.QC, and the protein expressed from the plasmid was designated sPSL.QC.

B. Construction of psPSL.Q

The fragment was purified and ligated into the pED plasmid (Kaufman et al., 1991) between the XbaI and EcoRI sites, along with the double stranded synthetic oligonucleotide DNA that recreated the codons from Asn 296 to Gln 309 and introduced a novel stop codon immediately following Gln 309. The sequence of the oligos is as follows:

```
                                              (SEQ ID NO: 14)
5'-AACTACCCAGTGGGAGCACCAGACCACATCTCTGTGAAGCAGTAG (SEQ ID NO: 15)
5'-AATTCTACTGCTTCACAGAGATGTGGTCTGGTGCTCCCACTGGGTAG
TT
```

The resulting plasmid was designated pED.sPSL.Q, and the protein expressed from the plasmid was designated sPSL.Q.

C. Construction of psPSL.T7

Oligonucleotides encoding 14 amino acids including an epitope derived from the phage T7 major capsid protein were synthesized, creating a C-terminal fusion of the epitope "tag" with an additional 32 amino acids derived from the vector sequence. Two oligonucleotides having the sequences

```
                                              (SEQ ID NO: 16)
5'-CTAGACCCGGGATGGCATCCATGACAGGAGGACAACAAATGGTAGGC
CGTAG
and
                                              (SEQ ID NO: 17)
5'-AATTCTACGGCCTACCCATTTGTTGTCCTCCTGTCATGGATGCCATC
CCGGGT
``` were duplexed and ligated with the large XbaI-EcoRI fragment of mammalian expression plasmid pED. The resulting plasmid, pED.T7 was restricted with XbaI and SmaI and ligated to the 950 bp XbaI-HincII fragment described above, resulting in plasmid pED.sPSL.T7. The protein resulting from expression of pED.sPSL.T7 was designated sPSL.T7.

D. Construction of Soluble P-selectin Ligand-IgGFc Chimera

The plasmid DNA encoding a soluble, extracellular form of the P-selectin ligand protein fused to the Fc portion of human immunoglobulin IgG1 was constructed as follows: the mammalian expression vector pED.Fc contains sequences encoding the Fc region of a human IgG1 with a novel linker sequence enabling the fusion of coding sequences amino terminal to the hinge region via a unique XbaI restriction site. A three fragment ligation was performed: pED.Fc was restricted with XbaI and gel purified in linear form. The 950 bp fragment from pMT21:PL85 described above comprised the second fragment. The third fragment consisted of annealed synthetic oligonucleotide DNAs having the following sequence:

```
   5'-CTGCGGCCGCAGT          (SEQ ID NO: 18)

5'-CTAGACTGCGGCCGCAG      (SEQ ID NO: 19)
```

The ligation products were grown as plasmid DNAs and individual clones having the correct configuration were identified by DNA sequencing. The plasmid was designated pED.PSL.Fc. The DNA coding region of the resulting soluble P-selectin ligand IFc fusion protein is shown in SEQ ID NO:6.

EXAMPLE 6

Characterization of Expressed P-Selectin Ligands

A. Binding Characterization of Full-Length P-Selectin Ligand Protein Expressed on COS Cells Co-transfection of COS cells with the pEA.3/4FT plasmid of Example 2 and the pMT21:PL85 plasmid of Example 1 yields COS cells which specifically bind to CHO:P-selectin cells. This binding is observed only upon co-transfection of pEA.3/4FT and pMT21:PL85; use of either plasmid alone generates COS cells which do not bind to CHO:P-selectin cells. No binding is observed between the parental CHO (DUKX) cell line which does not express P-selectin and COS cells co-transfected with pEA.3/4FT and pMT21:PL85. The binding between the co-transfected COS cells and CHO:P-selectin cells is sensitive to chelators of divalent ions such as EDTA and EGTA, consistent with the $Ca^{++}$ dependency of P-selectin mediated cellular adhesion. A neutralizing anti-P-selectin monoclonal antibody blocked the binding between the CHO:P-selectin cells and the COS cells which had been co-transfected with pEA.3/4FT and pMT21:PL85, while a non-neutralizing anti-P-selectin monoclonal antibody had no effect on the binding. The antibody results indicate that the functional domain(s) of P-selectin are required for binding to P-selectin ligand protein expressed on the surface of COS cells.

B. Electrophoretic Characterization of Full-Length P-selectin Ligand Expressed in COS Cells Detergent extracts of co-transfected COS cells were prepared as follows: 45 hours post co-transfection, approximately $1.5 \times 10^7$ cells were suspended in 5 ml of lysis buffer (10 mM piperazine-N,N'-bis[2-ethanesulfonic acid] (PIPES) pH 7.5, 100 mM KCl, 3 mM $MgCl_2$, 1 mM benzamidine, 0.5 µg/ml leupeptin, 0.75 µg/ml pepstatin, 1 mM ethylmaleimide, and 1 µg/ml aprotinin) and lysed by sonication. Cellular debris was removed by low speed centrifugation (500×g, 10 minutes), and a membrane fraction collected by ultracentrifugation (100,000×g, 60 min). The high speed membrane pellet was resuspended in an extraction buffer (10 mM 3-[N-Morpholino]propanesulfonic acid] (MOPS) pH 7.5, 0.1 M NaCl, 0.02% $NaN_3$, 1% Thesit® (Sigma), 1 mM benzamidine, 0.5 µg/ml leupeptin, 0.75 µg/ml pepstatin, 1 mM ethylmaleimide, and 1 µg/ml aprotinin). Samples were then subjected to SDS polyacrylamide gel electrophoresis and transfer to nitrocellulose blots as follows: an aliquot of the detergent extract was suspended in 1% SDS loading buffer and heated for 5 minutes at 100° C. before loading onto an 8-16% polyacrylamide gel (reduced) or a 6% gel (non-reduced) and electrophoresed in the Laemmli buffer system. Blots were prepared using Immobilon-P® transfer membranes. The blots were immersed in 10 mM MOPS pH 7.5, 0.1 M NaCl, 0.02% $NaN_3$, 1 mM $MgCl_2$, 1 mM $CaCl_2$, and 10% non-fat milk overnight at 4° C. Blots were rinsed once in the above buffer, minus the milk, and incubated in blotting buffer (10 mMMOPS pH 7.5, 0.1M NaCl, 1% bovine serum albumin, 0.05% Thesit, 1 mM $MgCl_2$, 1 mM $CaCl_2$) for 30 minutes at room temperature.

The blots were then probed for the P-selectin ligand as follows: 50 ng of a P-selectin/Fc chimera was pre-incubated with 3 µCi of $^{125}$I-Protein A in blotting buffer for 30 minutes at room temperature. Additional excipients (e.g., EDTA, EGTA, monoclonal antibodies) could be added to the pre-incubation mixture at this point to evaluate their effects on binding of the chimera to the P-selectin ligand. The pre-incubated mixture was then incubated with the blots (prepared as above) for 60 minutes at room temperature, and the blots were subsequently washed four times with the same blotting buffer (without bovine serum albumin), air dried, and autoradiographed at −70° C.

Under non-reducing conditions, two bands were observed with this technique for membrane extracts prepared from co-transfected COS cells. The major band migrated with an estimated molecular weight of approximately 220 kD, whereas the minor band migrated with a molecular weight of approximately 110 kD. Under reducing conditions, only a single band was observed with a molecular weight of approximately 110 kD, indicating that under non-reducing conditions, the P-selectin ligand exists as a homodimer. The approximate molecular weight of the reduced monomer is greater than that predicted from the deduced amino acid sequence of the cDNA clone (45 kD), indicating that the expressed protein undergoes extensive post-translational modification (see Example 6(C)). The specificity of the P-selectin/Fc chimera was confirmed by the observation that a nonspecific $IgG_1$ probe yielded no bands on the blots. Additionally, the binding of the P-selectin/Fc chimera to the blots was abolished by EDTA, EGTA, and a neutralizing anti-P-selectin monoclonal antibody. Specific bands on the blots were observed only from membrane extracts of COS cells co-transfected with the pEA.314FT and pMT21:PL85 plasmids. Membrane extracts from control transfections (pEA.3/4FT or pMT21:PL85 alone) failed to yield observable bands on blots.

C. Glycosylation of P-selectin Ligand Protein

The presence of covalently attached carbohydrate on recombinant P-selectin ligand and its role in binding to P-selectin was determined as follows: COS cells were co-transfected with pED.sPSL.T7 of Example 5(C) and the pEA.3/4FT plasmid of Example 2. After 48 hours, the cells were pulsed with $^{35}$S-methionine. 200 µl of $^{35}$S methionine-labeled sPSL.T7 conditioned medium was incubated with 5 µg LEC-γ1 in the presence of 2 nM $CaCl_2$ and 1 mg/ml bovine serum albumin (BSA). After rotating for 2 hours at 4° C., Protein A-Sepharose beads (Pharmacia) were added for 1 hour at 4° C., pelleted by centrifugation and washed twice in Tris buffered saline (20 mM Tris-HCl, 150 mM NaCl pH 7.5, hereinafter TBS) containing 2 mM $CaCl_2$ and 1 mg/ml BSA. The pellets were then resuspended and treated with neuraminidase (*Streptococcus pneumoniae*), O-glycanase, and N-glycanase (all from Genzyme) as follows. All glycosidase digestions were done at 37° C. overnight. For neuraminidase digestion, the pellet was resuspended in 50 µl 2-(N-morpholino)-ethanesulfonic acid (MES) buffer, pH 6.5 (Calbiochem) and 0.1% SDS, heated at 95° C. for 5 minutes, then pelleted. The supernatant was modified to contain 1.4% n-Octyl B-D-glucopyranoside (OGP), 10 mM calcium acetate, 20 mM sodium cacodylate and 2.5 mM PMSF, final pH 7.0 Eight µl neuraminidase was added for a final concentration of 1 unit/ml. For neuraminidase/O-glycanase digestion, the sample was prepared as above and along with the neuraminidase, the O-glycanase was also added to a final concentration of 0.1 unit/ml. For N-glycanase digestion, the pellet was resuspended in 54 ul MES buffer and 1% SDS, heated at 95° C. for 5 minutes, then pelleted. The supernatant was modified to contain 0.2 M sodium phosphate, 3.5% OGP, and 2.5 mM PMSF, final pH 8.5. N-glycanase was added for a final concentration of 12 units/ml and incubated as above.

The effect of glycosidase treatment on sPSL.T7 was assessed in two ways. For this, each digested protein sample was divided into two equal fractions. One fraction was precipitated with the P-selectin polyclonal antibody of Example 7(A), to show the effect of digestion on the electrophoretic mobility. The other fraction was precipitated with the LEC-γ1 chimera of Example 4(A), to assess the remaining P-selectin ligand binding activity after digestion. The immunoprecipitationed samples were analyzed by SDS-polyacrylamide gel electrophoresis under reducing conditions and autoradiography.

In the absence of glycosidase treatment, autoradiography revealed comparable bands (with molecular weights of 110 kD) for each precipitation. When the P-selectin ligand protein was treated with neuraminidase, anti-P-selectin ligand polyclonal antibody precipitation revealed a slight decrease in mobility, consistent with removal of sialic acid residues. The amount of P-selectin ligand protein precipitated by LEC-γ1 was significantly reduced after neuraminidase treatment, consistent with the role of sialic acid residues in the P-selectin/P-selectin ligand interaction. When the P-selectin ligand protein was treated with both neuraminidase and O-glycanase, a substantial increase in electrophoretic mobility was observed after precipitation with the anti-P-selectin ligand polyclonal antibody, indicating that a number of O-linked oligosaccharide chains had been removed. However, removal of O-linked oligosaccharides from the P-selectin ligand protein may not have been complete, since the electrophoretic mobility did not correspond to a protein with a molecular weight of 38 kD, as would be predicted from the amino acid sequence set forth in SEQ ID NO:1. The neuraminidase/O-glycanase digested P-selectin ligand protein bound to LEC-γ1 very poorly, further indicating the role of oligosaccharides in the P-selectin/P-selectin ligand interaction. Treatment of the purified P-selectin ligand with N-glycanase resulted in a slight increase in electrophoretic mobility, demonstrating that some of the consensus sites for N-linked glycosylation are occupied. The amount of P-selectin ligand protein precipitated by LEC-γ1 was slightly reduced, indicating that N-linked glycosylation also contributes to the P-selectin/P-selectin ligand interaction, though not as dramatically as sialylation and O-linked glycosylation.

EXAMPLE 7

Polyclonal Antibodies Specific for P-Selectin Ligands

A. Polyclonal Rabbit Anti-P-Selectin Ligand Protein/Maltose Binding Protein Fusion Protein The anti-P-selectin ligand polyclonal antibody was generated by immunizing rabbits with a fusion protein generated in *E. coli*. The fusion protein consisted of the amino terminal one-third of the P-selectin ligand (amino acids 1 to 110 of SEQ ID NO:1) fused in frame to the maltose binding protein (Maina, C. V. et al., Gene 74, 365-373 (1988); Riggs, P., in Current Protocols in Molecular Biology F. M. Ausebel et al., Eds., Greene Associates/Wiley Interscience (New York, 1990) chapter 16.6). Under conditions employed herein, the fusion protein antibody recognizes the P-selectin ligand protein.

B. Polyclonal Rabbit Anti-sPSL.T7 Protein

A soluble form of the invention (sPSL.T7; see example 5(C)) was purified to apparent homogeneity according to the following scheme: COS cells were transfected with three plasmids, one encoding each of the following: sPSL.T7 (Example 5(C)), 3/4FT (Example 2), and a soluble form of PACE (as set forth in SEQ ID NO:5). After 72 hours, the conditioned medium was collected and recombinant sPSL.T7 was purified as follows.

Conditioned medium was diluted two fold with 50 mM MOPS, 150 mM NaCl, 0.5 mM $CaCl_2$ and 0.5 mM $MnCl_2$, pH 7.2, and applied to a column of lentil lectin-Sepharose 4B equilibrated in the same buffer. After loading, the column was washed with the same buffer until the optical absorbance at 280 nm dropped to a stable baseline. The column was then eluted with the same buffer which had been adjusted to 0.5 M α-methyl-mannoside and 0.3 M NaCl. Recombinant sPSL.T7 was collected over 5-15 column volumes of this elution buffer. The lentil lectin eluate was then subjected to a 0-70% ammonium sulfate precipitation by adding 472 g of ammonium sulfate per liter of column eluate at 4° C. After stirring for 30 minutes, the precipitate was resuspended in a minimal volume of TBS (20 mM Tris-HCl, 150 mM NaCl, pH 7.5) and applied to a TSK $G4000SW_{XL}$ gel filtration column equilibrated in TBS. The flow rate on the column was 0.5 m/min and a guard column was employed. In aliquots of <250 μl, the resuspended ammonium sulfate pellet was injected on the column and fractions analyzed by SDS-PAGE with Western analysis. Fractions containing sPLS.T7 were pooled and then used for immunizing rabbits.

Antibodies to sPSL.T7 were generated in the standard fashion by antigen priming and subsequent boosting over a 3 month period. Specifically, primary immunization was performed by mixing 50 μg of sPSL.T7 (denatured by mixing in 0.1% SDS and heating for 10 minutes at 100° C.) with complete Freund's adjuvant and injected at five sites subcutaneously. The second (and all subsequent) boosts were performed by mixing 25 μg of sPSL.T7 (denatured by mixing in 0.1% SDS and heating for 10 minutes at 100° C.) [12.5 μg for the third and subsequent boosts] with incomplete Freund's adjuvant and injecting at two sites subcutaneously (or later, intramuscularly) every two weeks. Test bleeds were performed every two weeks to monitor antibody titer. When the antibody titer reached a suitable level, a larger scale bleed was performed and a total serum fraction prepared. This polyclonal antibody preparation was used to inhibit the specific binding of HL60 cells to CHO:P-selectin cells in a manner similar to that described in Example 4.

This assay employed fluorescently-labeled HL60 cells (labelled with BCECFAM; 2',7'-bis-(2-carboxymethyl)-5-and-6)-carboxyfluorescein, acetoxymethyl ester) binding to CHO cells plated on the bottom of microtiter plates. The labelled HL60 cells were pre-incubated with either sera containing polyclonal antibody or with pre-immune sera for 30 minutes at 4° C. The cells were then washed and incubated with the CHO:P-selectin cells for 10 minutes. The plates were then washed and the fluorescence read with a fluorescence microtiter plate reader. Using this assay, a 1:15 dilution of the anti-sPSLT7 polyclonal serum resulted in essentially complete inhibition of HL60 cell binding to CHO:P-selectin. Demonstrable inhibition of HL60 binding to CHO:P-selectin was still observed at antiserum dilutions of 1:150. Pre-immune serum had no effect on HL60 cell binding to CHO:P-selectin.

EXAMPLE 8

Cotransformation with Core2

A. Isolation of the cDNA Encoding Core2 GlcNAc Transferase

The cDNA encoding core2 GlcNAc transferase was isolated by standard molecular biology techniques. Two oligos were designed at the 5' and 3' end (including translational initiation and termination codon, respectively) based on the published human core2 sequence (Bierhuizen, M. F. A., Fukuda, M., Proc. Natl. Acad. Sci. 89, 9326-9330 (1992)). The pools of an HL60 cDNA library (Sako, D., Cell 75, 1179-1186 (1993)) were used as template to amplify the core2 coding sequence by a standard PCR protocol. The PCR amplified fragment was purified and subcloned into pED vector. To isolate cDNA, the pools which gave a positive signal in the PCR reaction were transformed into E. coli and plated. Transformants were transferred onto nitrocellulose filters and hybridized with a $^{32}P$ radiolabelled PCR fragment according to standard protocols. Positive clones were picked and purified by replating. The sequence of the cDNA and PCR clone was confirmed by dideoxy sequencing.

B. Generation of Stable PSGL-1 Chinese Hamster Ovary Cell Lines Expressing Core2 Enzyme A cell line made in accordance with the methods of Example 3 expressing full-length P-selectin ligand protein and 3/4 fucosyltransferase was co-transfected with core2 cDNA and a neomycin resistance gene (pMT4Neo) by standard calcium phosphate methods. After about two weeks, stable G418-resistant transfectants were picked either as single isolates or in a pool. These transfectants were grown in 1 mg/ml G418 complete DMEM media and analyzed for core2 enzyme activity (Higgins, E. A., et al., J. Biol. Chem. 266, 6280-6290 (1991)). Positive clones or pools found positive for core2 activity were analyzed for P-selectin ligand binding to P-selectin by various methods. In a similar fashion, cell lines expressing either P-selectin ligand protein or soluble P-selectin ligand protein with both the 3/4 fucosyltransferase and PACE enzymes (see Example 3) were used to isolate stable cotransfectants of core2 as described above.

C. Effects of Core2 on P-Selectin Binding Activity

The effects of core2 on P-selectin binding activity was evaluated by three different methods:

1. Binding of mPSGL-1 Transfectants to Immobilized Soluble P-Selectin or P-Selectin/IgG Chimera.

Figure 1:
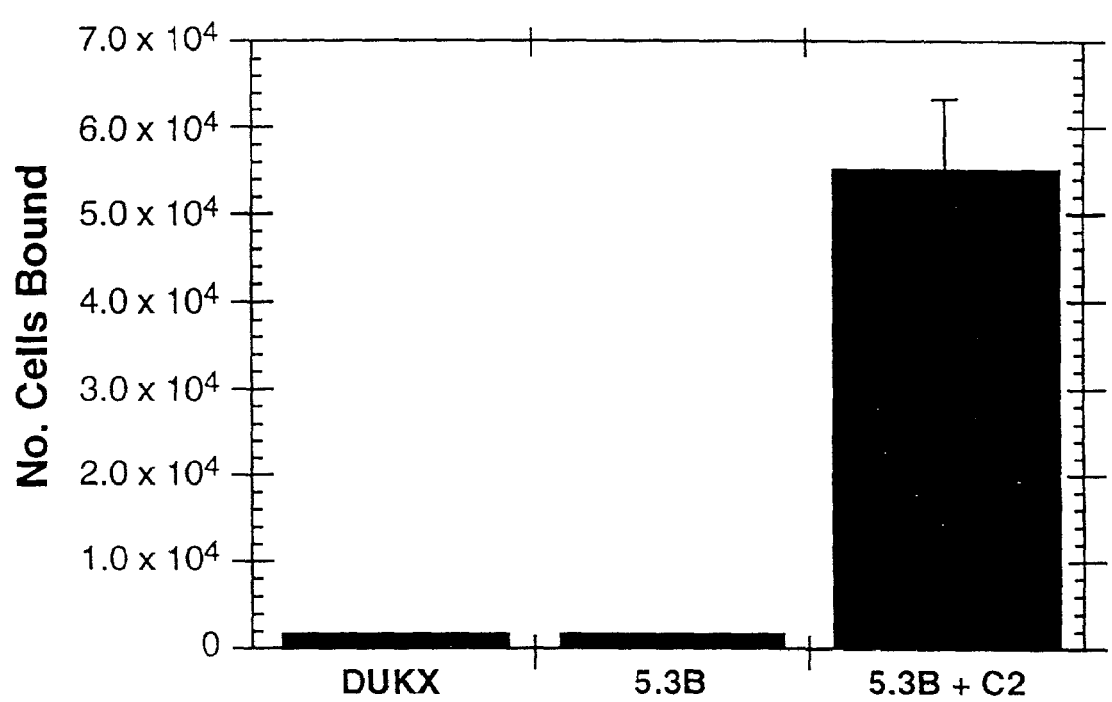
FIG. 1 is a graph comparing the binding of P-selectin ligand proteins expressed with and without core2.

48-well plates were coated with 1 ug/ml anti human Fc antibody in 50 mM Tris pH 9.5 at 4° C. for five to six hours. After washing twice with HBSS buffer, P-selectin/IgG chimera (0.1-1 ug/ml conc., Example 5) was plated in HBSS buffer overnight at 4° C. The plates were blocked with BSA (3 mg/ml) at 4° C. for three to four hours. In the case of soluble P-selectin ligand protein, the protein was coated directly onto plates in the same buffer. The $^3H$ labelled CHO cells were lifted with 2 mM EGTA, washed three times with PBS, and resuspended to a final density of $10^6$ cells/ml. A 300 ul aliquot of this suspension was added to each well (300,000 cell/well). After incubating for 12 minutes at room temperature, wells were washed four times with serum free DMEM to remove unbound cells. Bound cells were lifted with 5 mM EGTA and counted in scintillation counter. U937 cells, used as a positive control for native P-selectin ligand protein binding, were pretreated with gamma globulin (5 mg/ml) to block endogenous Fc receptor before binding to P-selectin IgG chimera. Comparative binding data are shown in FIG. 1.

2. Immunoprecipitation of PSGL-1 with P-Selectin/IgG Chimera.

Figure 2:
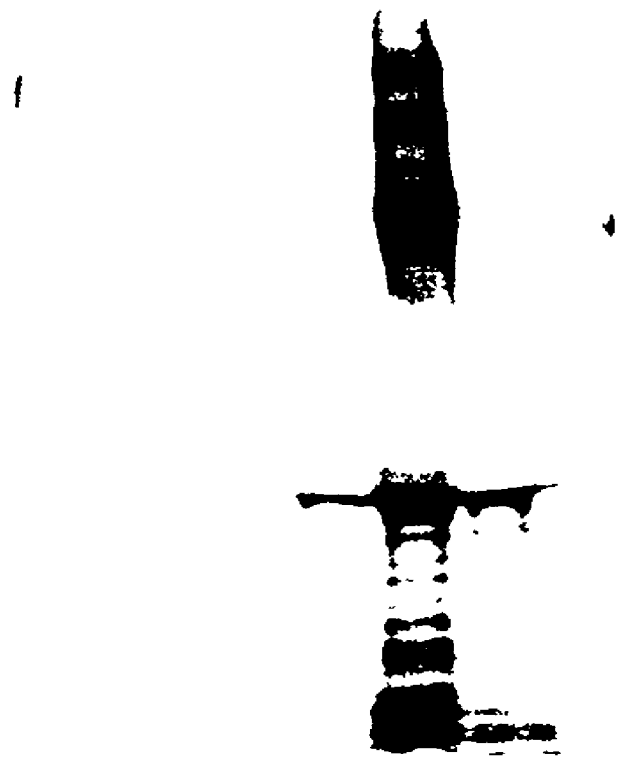
FIG. 2 is an autoradiograph of immunoprecipitations of P-selectin ligand protein expressed with and without core2.

Recombinant full-length or soluble P-selectin ligand protein prepared from transformants, with and without additional core2, was labelled with $^{35}S$-methionine and subsequently immunoprecipitated with either the anti P-selectin ligand protein polyclonal antibody or P-selectin ligand/IgG chimera as described previously in Examples 7 and 5; Sako, D., Cell 175, 1179-1186 (1993). Data are depicted in FIG. 2.

3. Flow Cytometry.

Figure 3:
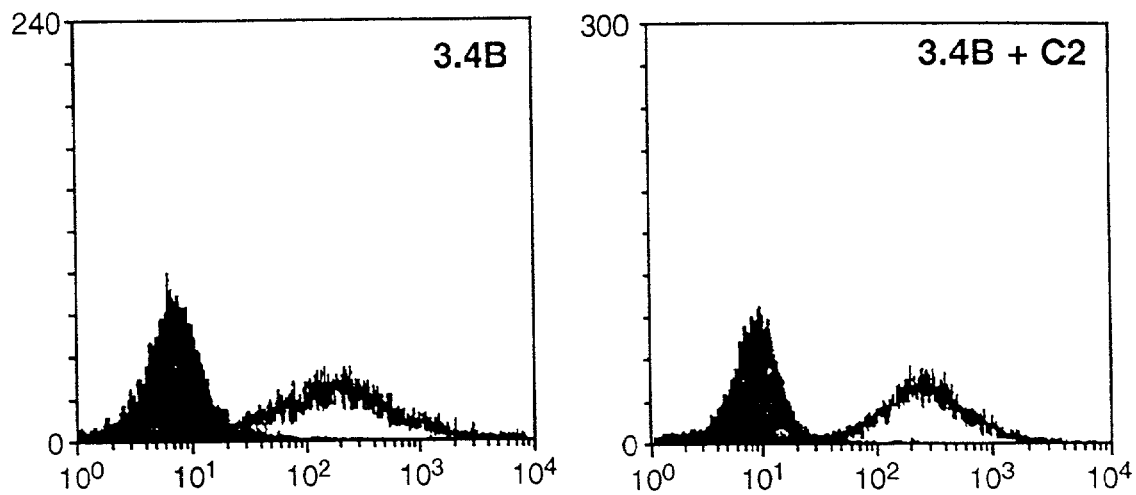
FIG. 3 depicts the results of flow cytometry analysis of the binding of P-selectin ligand protein (expressed with and without core2) to P-selectin/IgG chimera (LEC-γ1) and anti-P-selectin ligand protein monoclonal antibody (MAb 275).
Figure 3:
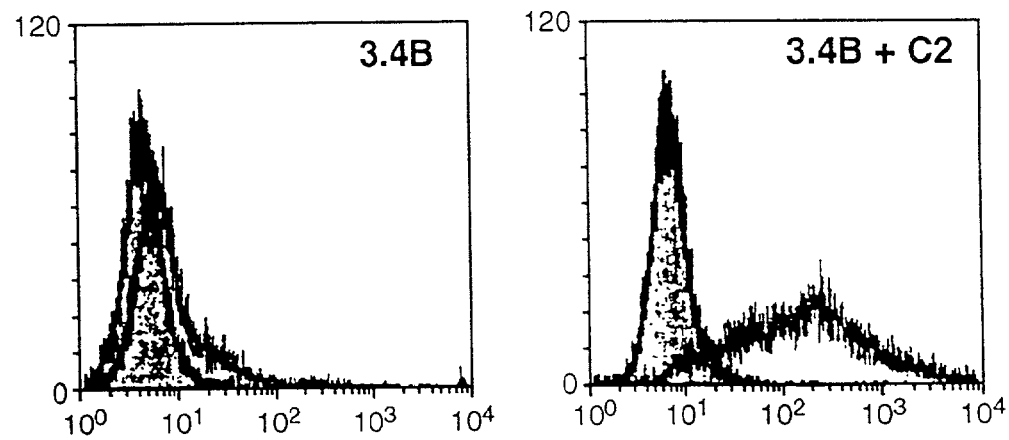
Figure 3:
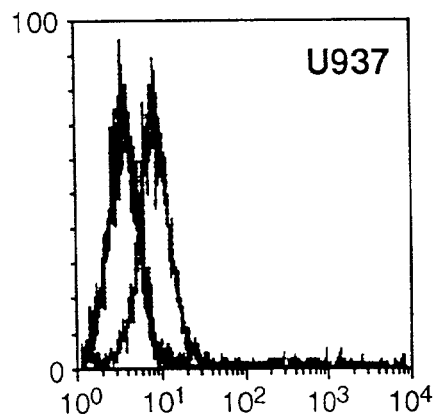

Stable murine P-selectin ligand protein transfectants (with and without core2) were analyzed by standard FACS techniques using either P-selectin/IgG chimera (LecY1) (Example 5) or anti P-selectin ligand protein monoclonal antibody (MAb 275, raised against a peptide having the sequence from amino acid 42 to amino acid 56 of SEQ ID NO:2). Both reagents were preconjugated to FITC labelled Protein A. Cells were analyzed by FACS after incubating with this conjugate for 30 minutes at 4° C. in the presence of 2 mM $CaCl_2$. Data are depicted in FIG. 3.

EXAMPLE 9

E-Selectin Binding of P-Selectin Binding Protein

E-Selectin/IgG chimera was made as described in Example 5 for the P-selectin IgG chimera using an E-selectin encoding DNA including amino acids-21 to 536 of the sequence reported in Bevilacqua et al., Science, 243:1160 (1989).

U937 cells (approximately $6.5 \times 10^7$) were recovered from tissue culture plates and divided equally into two 50 mL cultures (final concentration of $1.3 \times 10^6$ cells/mL) containing fresh complete RPMI medium and 50 µCi/ml of $^3$H-glucosamine hydrochloride (labels the protein-linked carbohydrate of glycoproteins [Varki, FASEB 5:226-235 (1991)]. After 48 hours incubation, the cells from both cultures were recovered by centrifugation and washed three times with PBS. The pelleted cells were suspended in 2.5 mL each of a lysis buffer containing 1% Triton X-100 and disrupted by probe sonication for two minutes. The detergent lysates were placed on ice for three hours and then resonicated for an additional two minutes. The lysates were centrifuged at 16,000 rpm for five minutes, the supernatants were recovered and each adjusted to 12 mL with lysis buffer containing no detergent. To one of the two diluted cell lysates was added 100 uL of protein A sepharose precoupled with P-selectin/IgG chimera (see Example 5) and to the other was added 100 uL of protein A sepharose precoupled with E-selectin/IgG chimera. Both chimeric proteins were present at a density of approximately 2 mg protein/mL of resin. Binding reactions were allowed to proceed overnight at 4 degrees C. with end-over-end mixing. On occasion, purified membranes from U937 cells served as the starting material for the detergent extraction of labeled proteins. In these cases, the detergent extraction and affinity precipitation steps were essentially identical to the above.

Following incubation, the two parallel reaction mixtures were each centrifuged at 2,000 rpm and supernatants were discarded. The resin pellets were washed four times with buffer (10 mM MOPS, 100 mM NaCl, 1 mM $CaCl_2$, 1 mM $MgCl_2$, 0.02% $NaN_3$, pH 7.5 with Triton X-100 [0.25% for the first and second washes, 0.1% for the third wash and 0.01% for the fourth wash]). A final 1 mL pre-elution wash of each resin pellet using buffer containing 0.01% Triton X-100 was conducted and these were retained for quantitation of radioactive counts by liquid scintillation counting (LSC). The resins were then eluted overnight at 4 degrees C. with end-over-end mixing in 1 mL each of buffer containing 0.01% Triton X-100 and 10 mM EDTA. The supernatants were recovered by centrifugation and then quantitated by LSC.

Autoradiography of the materials released from the resins by EDTA was performed by electrophoresis of samples (approximately 10,000 cpm samples concentrated by Centricon-10 units where needed) on 10% cross-linked SDS-PAGE gels, subsequent treatment of the gels with EN3HANCE (Dupont) as per the manufacturer's instructions followed by drying for two hours on a commercially available gel dryer (Bio-Rad). Exposure of the dried gels to X-ray film was conducted for a minimum of three days at −80 degrees C.

Elution of immobilized E- or P-selectin, previously exposed to detergent extracts of U937 cells and exhaustively washed, with EDTA yielded liberated, $^3$H-glucosamine labeled proteins. The amount of radiolabel recovered from the EDTA eluates was at least 10-fold higher than the counts observed in the final, pre-EDTA washes. This observation suggests that both P- and E-selectin chimeras affinity captured ligand(s) from U937 whole cell lysates in an EDTA-dependent manner and that captured ligands were subsequently released upon treatment of the resins with EDTA.

Figure 4:
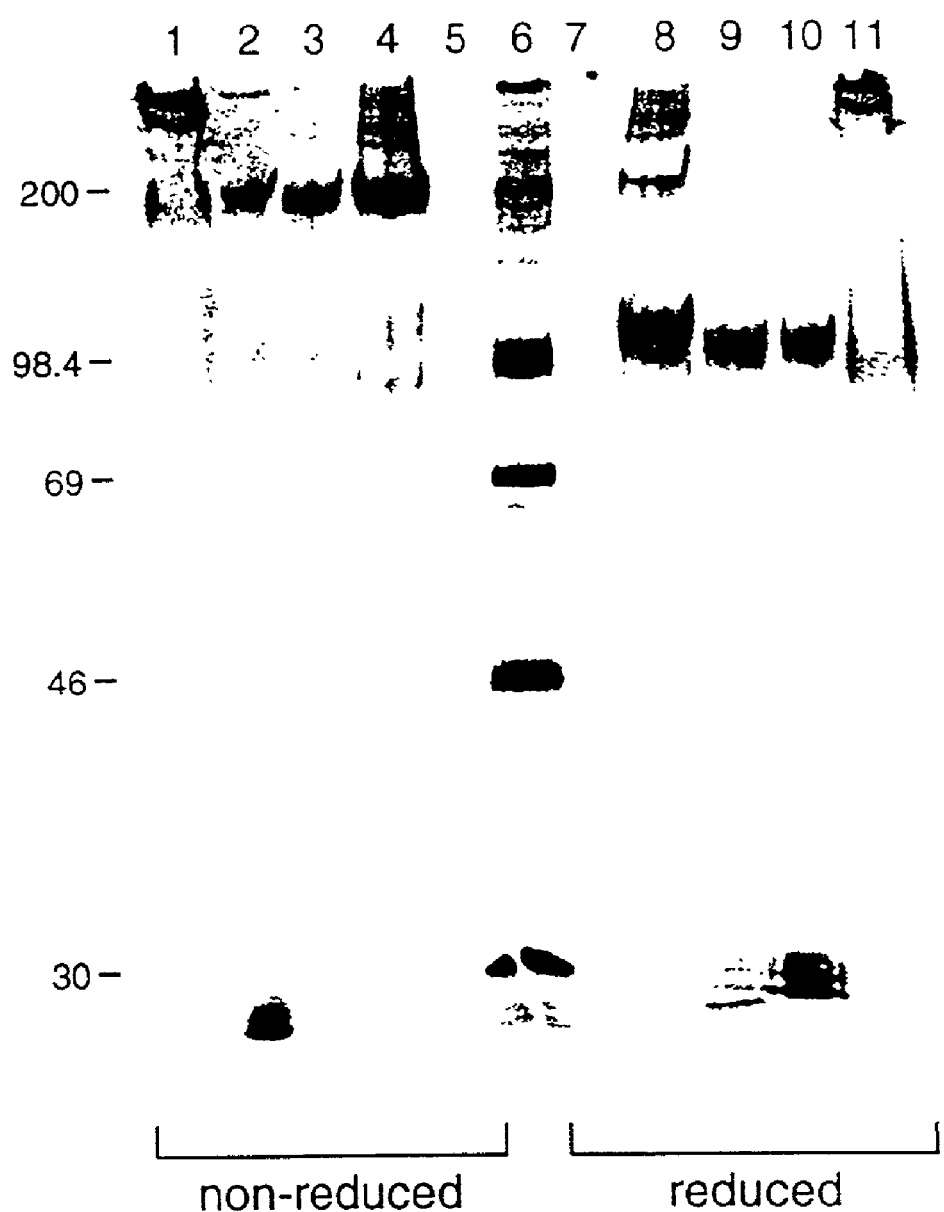
FIG. 4 is an autoradiograph of proteins, including P-selectin ligand protein, which bound to P- and E-selectin/IgG chimeras.

The evaluation of the proteins released by EDTA from the two chimeras was performed by SDS-PAGE and autoradiography under reducing and non-reducing conditions (commercially available $^{14}$C-labeled molecular weight standards were employed). As shown by the autoradiograph depicted in FIG. 4, the released counts from the whole cell lysates treated with the P-selectin chimera (lanes 2 and 10) and the E-selectin chimera (lanes 4 and 8) correlated to a major species of 200 kD molecular weight, non-reduced (lanes 2 and 4), and 100 kD reduced (lanes 8 and 10). In different experiments depicted in FIG. 4, where purified membrane extracts were used as the starting material in place of whole cells, both the E-selectin chimera (lane 3, non-reduced and lane 9, reduced) and the P-selectin chimera (not shown) gave similar results. Other experiments have demonstrated that the major U937 glycoprotein which binds to P-selectin is immunoreactive with Rb3026, a polyclonal antibody raised against recombinant sPSGL1.T7. Therefore, P- and E-selectin specifically recognize a single major glycoprotein species with identical properties in each case.

EXAMPLE 10

Production and Analysis of Deleted or Altered Forms of Soluble P-Selectin Ligand Protein A. Generation of DNA Constructs Truncated forms of the P-selectin ligand protein-IgG chimeras were generated as follows. Plasmid pED.PSL.Fc was restricted with PstI and NotI and the 6 kb fragment comprising the Fc portion and vector, pEDFc6 kb, was gel purified. Plasmid constructs pED. 149.Fc, pED.47.Fc and pED. 19.Fc were created by standard PCR technique, using the following pairs of oligonucleotide primers:

"Upstream" primer for all constructs:

```
                                          (SEQ ID NO: 20)
5'-CCAGGTCCAACTGCAGGTCGACTCTAGAGGGCACTTCTTCTGGGCCC
ACG-3'
```

"Downstream" primer for 148Fc:

```
                                          (SEQ ID NO: 21)
5'-TATTATCTGTGCGGCCGCCCTCCAGAACCCATGGCTGCTGGTTGCAG
TGG-3'
```

"Downstream" primer for 47Fc:

```
                                          (SEQ ID NO: 22)
5'-TATTATCTGTGCGGCCGCGCAGCAGGCTCCACAGTGGTAG-3'
```

"Downstream" primer for 19Fc:

(SEQ ID NO: 23)
5'-TATTATCTGTGCGGCCGCGGAGGCTCCGTTTCTGGCAG-3'.

The template DNA for PCR reaction was pED.PSL.Fc. The PCR conditions were 94° C., 1 min.; 42° C., 1 min.; 72° C., 3 min.; 25 cycles, using a Perkin-Elmer Thermocycler. After completion of the last cycle, the reaction was treated with Klenow enzyme at 25° C. for 30 min., extracted with phenol chloroform, sodium acetate added to 0.3M, and the PCR product DNA was precipitated with 2.5 volumes of ethanol. The DNA pellet was rinsed with 70% ethanol and residual ethanol was evaporated. The resuspended DNA was digested with PstI and NotI, gel purified and ligated with the pEDFc6 kb fragment described above. Correct constructs were identified by restriction analysis and confirmed by DNA sequencing.

Plasmid pED.ΔY148.Fc, pED.H24.Q70.148.Fc were created by site directed mutagenesis (Maniatis et al., 1989, Molecular Cloning: A Laboratory Manual, Cold Spring Harbor Laboratories) using pED.148Fc as template and the following mutagenesis oligonucleotides:

for ΔY148:
(SEQ ID NO: 24)
5'-CGGAGACAGGCCACCGAATTCCTGCCAGAAACG-3' for H24:
(SEQ ID NO: 25)
5'-CCTCCAGAAATGCTGAGGCACAGCACTGACACCACTCCTC-3' for Q70:
(SEQ ID NO: 26)
5'-GAGCTGGCCAACATGGGGCAACTGTCCACGGATTCAGCAG-3'

Positive clones were identified by colony hybridization (Maniatis et al, supra).

pED.FFFE.148.Fc was constructed by restricting pED.AY148.Fc with EcoRI and ligating the following duplexed oligonucleotides:

5'-AATTCGAGTTCCTAGATTTTG-3'    (SEQ ID NO: 27)
and
5'-AATTCAAAATCTAGGAACTCG-3'.   (SEQ ID NO: 28)

Constructs of the series pED.FYYD.19.Fc, pED.FFYD.19.Fc and pED.FFFD.19.Fc, were made by restricting pED.ΔY148.Fc with EcoRI and NotI and ligating the following duplexed oligonucleotides:

for pED.FYYD.19.Fc:

(SEQ ID NO: 29)
5'-AATTCGAGTACCTAGATTATGATTTCCTGCCAGAAACTGAGCCTCCGC-3' and (SEQ ID NO: 30)
5'-GGCCGCGGAGGCTCAGTTTCTGGCAGGAAATCATAATCTAGGTACTCG-3';

for pED.FFYD.19.Fc:

(SEQ ID NO: 31)
5'-AATTCGAGTTCCTAGATTATGATTTCCTGCCAGAAACTGAGCCTCCGC-3' and (SEQ ID NO: 32)
5'-GGCCGCGGAGGCTCAGTTTCTGGCAGGAAATCATAATCTAGGAACTCG-3';

for pED.FFFD.19.Fc:

(SEQ ID NO: 33)
5'-AATTCGAGTTCCTAGATTTCGATTTCCTGCCAGAAACTGAGCCTCCGC-3' and (SEQ ID NO: 34)
5'-GGCCGCGGAGGCTCAGTTTCTGGCAGGAAATCGAAATCTAGGAACTCG-3'.

B. Plate Binding Assay for Analysis of Deleted or Altered Forms of Soluble P-Selectin Ligand Protein The individual plasmid DNAs encoding the various mutated forms of soluble PSGL-1/Fc chimeras were co-transfected with pEA.3/4FT and PACE cDNA in COS cells as described in Example 3(c). 50 mls of serum free medium, collected 40-64 hours post transfection from approximately $10^7$ COS cells, was purified on a column of 0.25 ml of protein A sepharose (Pharmacia) equilibrated with TBS supplemented with 2 mM $CaCl_2$. After washing with 20 mls of TBS/$CaCl_2$, the bound material was eluted with 0.5 mls of 0.1M acetic acid, 0.15M NaCl, 2 mM $CaCl_2$. The eluted material was neutralized with ½oth volume 3M Tris pH 9.0. The material was quantitated by measuring absorbance at 280 nm and by comassie blue staining of PAGE/SDS/Laemmli gels.

In order to produce non-sulfated forms of soluble PSGL-1, COS cell transfections of the relevant Fc chimeras were performed as described above except that following transfection the cells were cultured in the presence of 50 mM Chlorate (Sigma).

Quantitative adhesion of CHO:P-selectin, CHO:E-selectin and CHO:L-selectin expressing cells was performed as described in Example 4(c), with the following modifications: COS cell and antibodies were omitted. Instead, 48-well microtiter plates (Costar) were coated for 16 hours at 4° C. with varying quantities of protein A-purified soluble PSGL-1/Fc chimeras. The unbound material was removed and the coated wells were treated with Hank's buffered saline (HBS) with 1 mg/ml BSA and 2 mM $CaCl_2$ for 1 hour at 4° C. Tritium labeled CHO selectin expressing cells were added and binding quantitated as described in Example 4(c).

C. Effects of Alteration of N-Linked Glycosylation Sites

Figure 6:
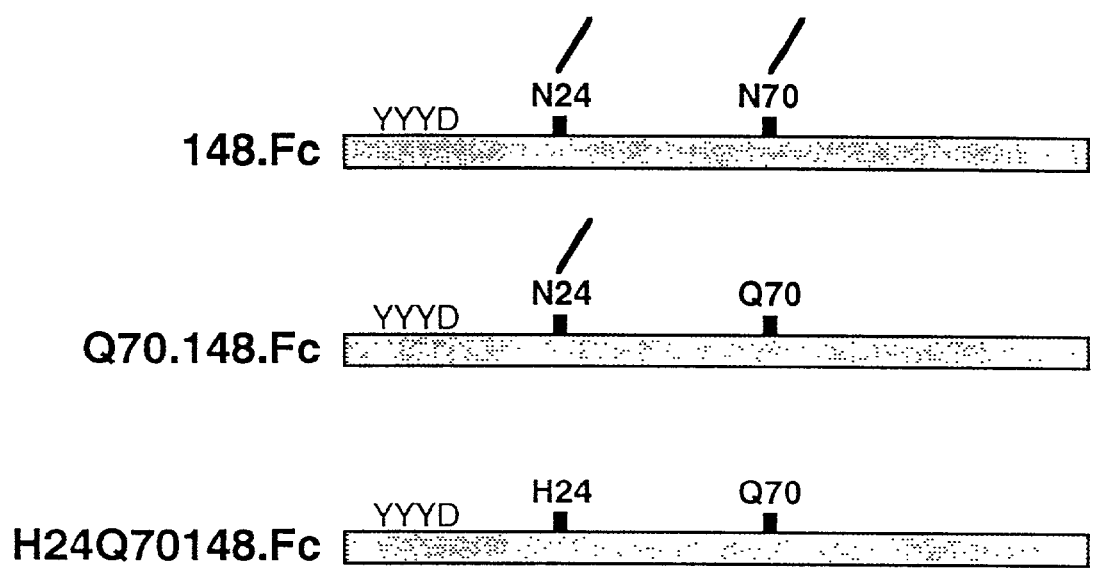
FIG. 6 is a schematic representation of several P-selectin ligand protein fragments constructed for the purpose of examining the role of N-linked glycosylation sites in binding of the P-selectin ligand proteins to selecting.

Constructs expressing three P-selectin ligand-IgG chimeras were constructed to examine the effects of N-linked glycosylation sites on selectin binding. These constructs had the following characteristics:

148.Fc amino acids 42-189 of SEQ ID NO:2
Q70.148.Fc amino acids 42-189 of SEQ ID NO:2, with the asparagine residue at position 111 of SEQ ID NO:2 replaced with a glutamine residue
H24.Q70.148.Fc amino acids 42-189 of SEQ ID NO:2, with the asparagine residue at position 65 of SEQ ID NO:2 with a histidine residue and the asparagine residue at position 111 of SEQ ID NO:2 replaced with glutamine residue These constructs are schematically represented in FIG. 6.

Figure 7:
FIG. 7 depicts the results of experiments to determine the role of N-linked glycosylation sites in binding of the P-selectin ligand proteins to selectins.

The binding of these constructs to protein A and P-selectin-IgG chimera (LEC-γ1) was compared. The results of these experiments are shown in FIG. 7. Comparison of lanes 4, 5 and 6 in the autoradiograph demonstrates that removal of one or both of the first two N-linked glycosylation sites in soluble P-selectin ligand protein does not significantly effect its binding to P-selectin.

D. Effects of Tyrosines

Constructs were made to examine the role of tyrosine in P-selectin ligand protein binding to selectins by alteration of the anionic region of the soluble protein. The following constructs were made:

ΔY148.Fc amino acids 42-189 of SEQ ID NO:2, with amino acids 46-52 deleted

Figure 8:
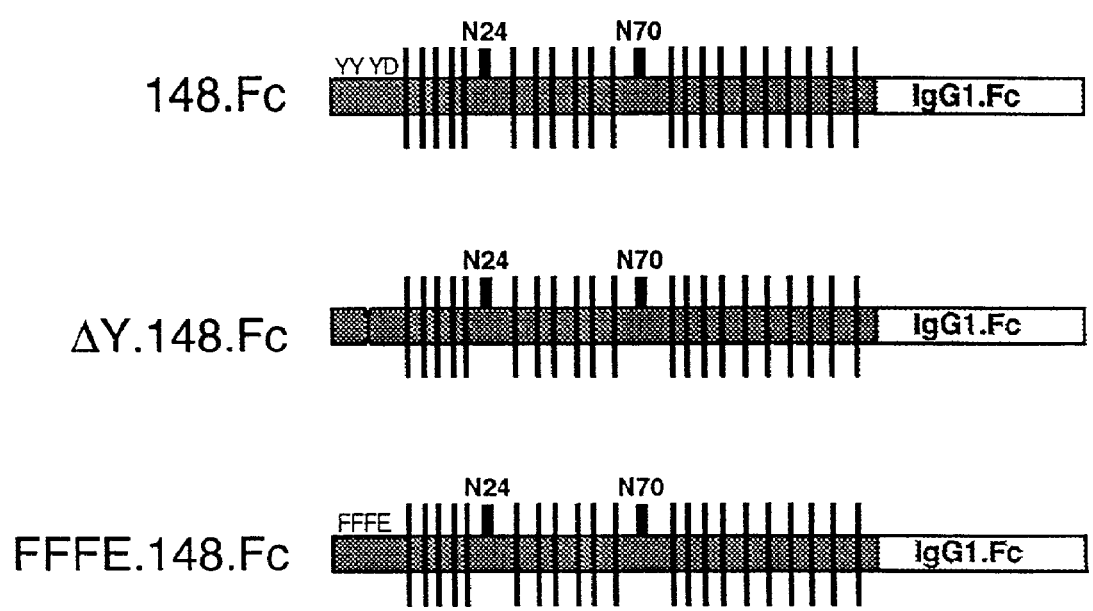
FIG. 8 is a schematic representation of several P-selectin ligand protein fragments constructed for the purpose of examining the role of sulfated tyrosine residues in binding of the P-selectin ligand proteins to selecting.

FFFE.148.Fc amino acids 42-189 of SEQ ID NO:2, with the tyrosine residues at positions 46, 48 and 51 replaced with phenylalanine residues and the aspartic acid residue at position 52 replaced with a glutamic acid residue These constructs are schematically represented in FIG. 8.

Figure 9:
FIGS. 9-11 depicts the results of experiments to determine the role of sulfated tyrosine residues in binding of the P-selectin ligand proteins to selecting.

The degree and sites of sulfation of P-selectin ligand protein were examined by expressing relevant constructs in the presence of radioactively labelled sulfate. The degree of sulfation of 148.Fc and ΔY.148.Fc were compared to that of a P-selectin-IgG chimera, which was not sulfated. Results are depicted in FIG. 9. These data demonstrate that the majority of sulfate incorporation is into the anionic region of the P-selectin ligand protein.

Additional constructs were made to determine whether the sulfation of the anionic region occurred at the tyrosine residues. The following additional constructs were made:

FYYD.19.Fc amino acids 42-60 of SEQ ID NO:2, with the tyrosine residue at position 46 of SEQ ID NO:2 replaced with a phenylalanine residue FFYD.19.Fc amino acids 42-60 of SEQ ID NO:2, with the tyrosine residues at positions 46 and 48 of SEQ ID NO:2 replaced with a phenylalanine residues FFFD.19.Fc amino acids 42-60 of SEQ ID NO:2, with the tyrosine residues at positions 46, 48 and 51 of SEQ ID NO:2 replaced with phenylalanine residues These constructs are schematically represented in FIG. 9.

Figure 10:
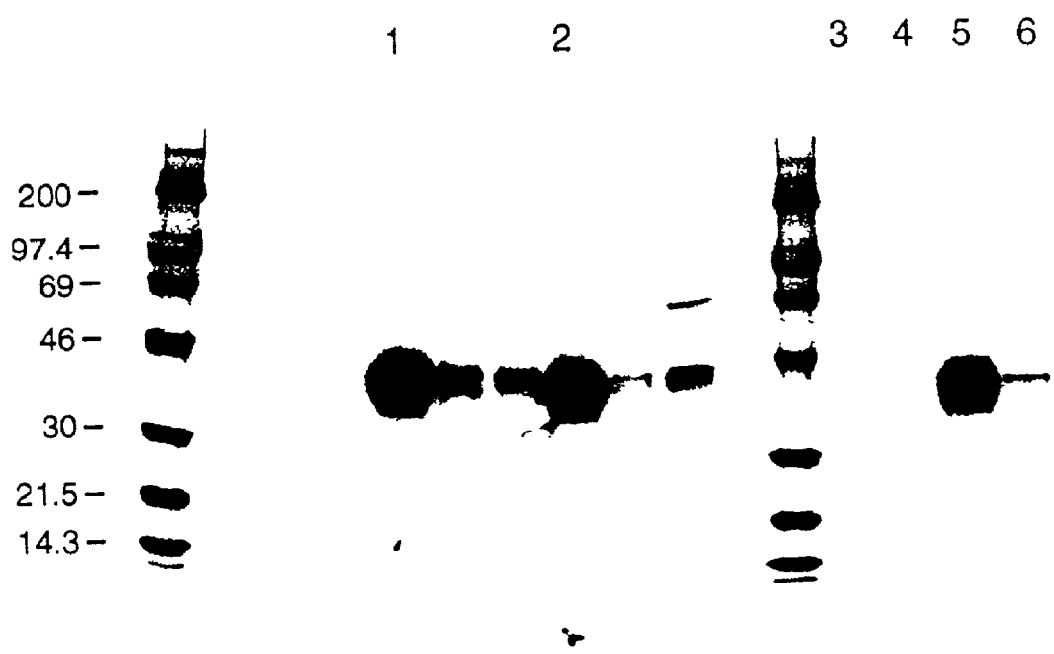

The degree of sulfation of these constructs was compared to 19.Fc ("YYYD.19.Fc"). Results are shown in FIG. 10. FYYD.19.Fc showed significant sulfation while FFFD.19.Fc was substantially less sulfated. Thus, the tyrosine residues of the anionic region of P-selectin ligand proteins are the major site of sulfation.

Figure 11:

Removal of sulfate from P-selectin ligand protein substantially reduces its binding to P-selectin. The binding of 148.Fc treated with chlorate to P-selectin was examined. As shown in FIG. 11, inhibition of sulfation by chlorate treatment substantially reduced the amount of P-selectin ligand protein binding to P-selectin.

E. Effects of C-Terminal Deletions

Several additional C-terminal deleted constructs were made as follows:

254.Fc amino acids 42-295 of SEQ ID NO:2
47.Fc amino acids 42-88 of SEQ ID NO:2
19.Fc amino acids 42-60 of SEQ ID NO:2

Figure 12:
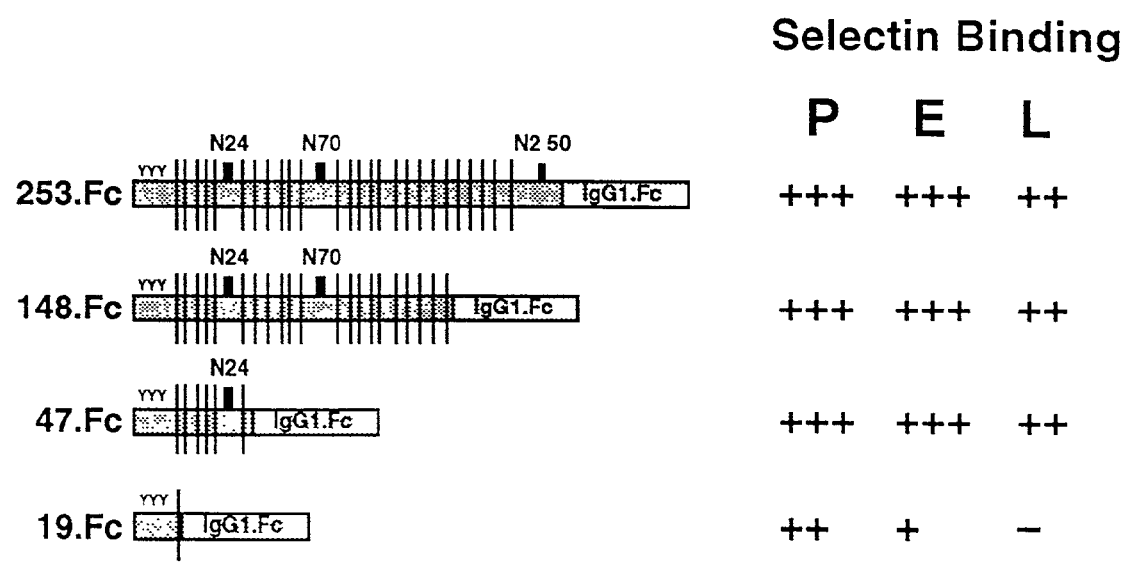

These constructs are schematically represented in FIG. 12.

Figure 23:
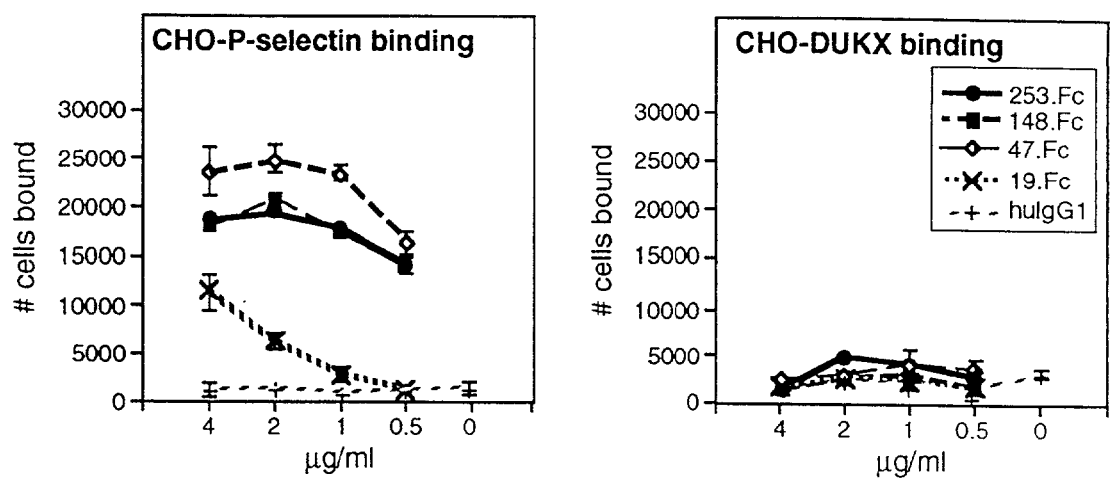
FIGS. 23 and 24 depict the results of experiments comparing the binding of various deleted and altered P-selectin ligand proteins to selecting.
Figure 24:
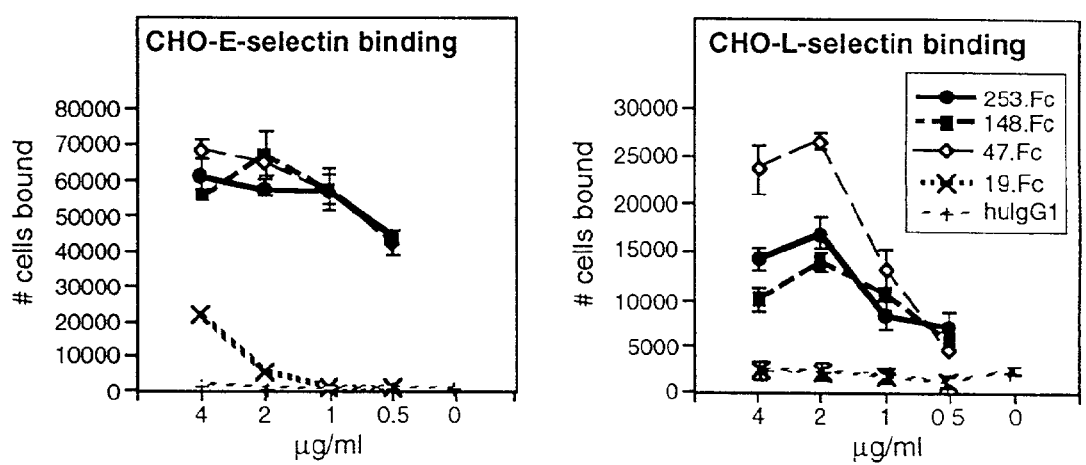

The binding of 254.Fc, 148.Fc, 47.Fc and 19.Fc to P-selectin, E-selectin and L-selectin was tested. FIGS. 23 and 24 compare the binding of these deletion chimeras to selectins and controls. Results are also summarized in FIG. 12.

F. Binding to P-Selectin and E-Selectin Expressing Cells

Figure 13:
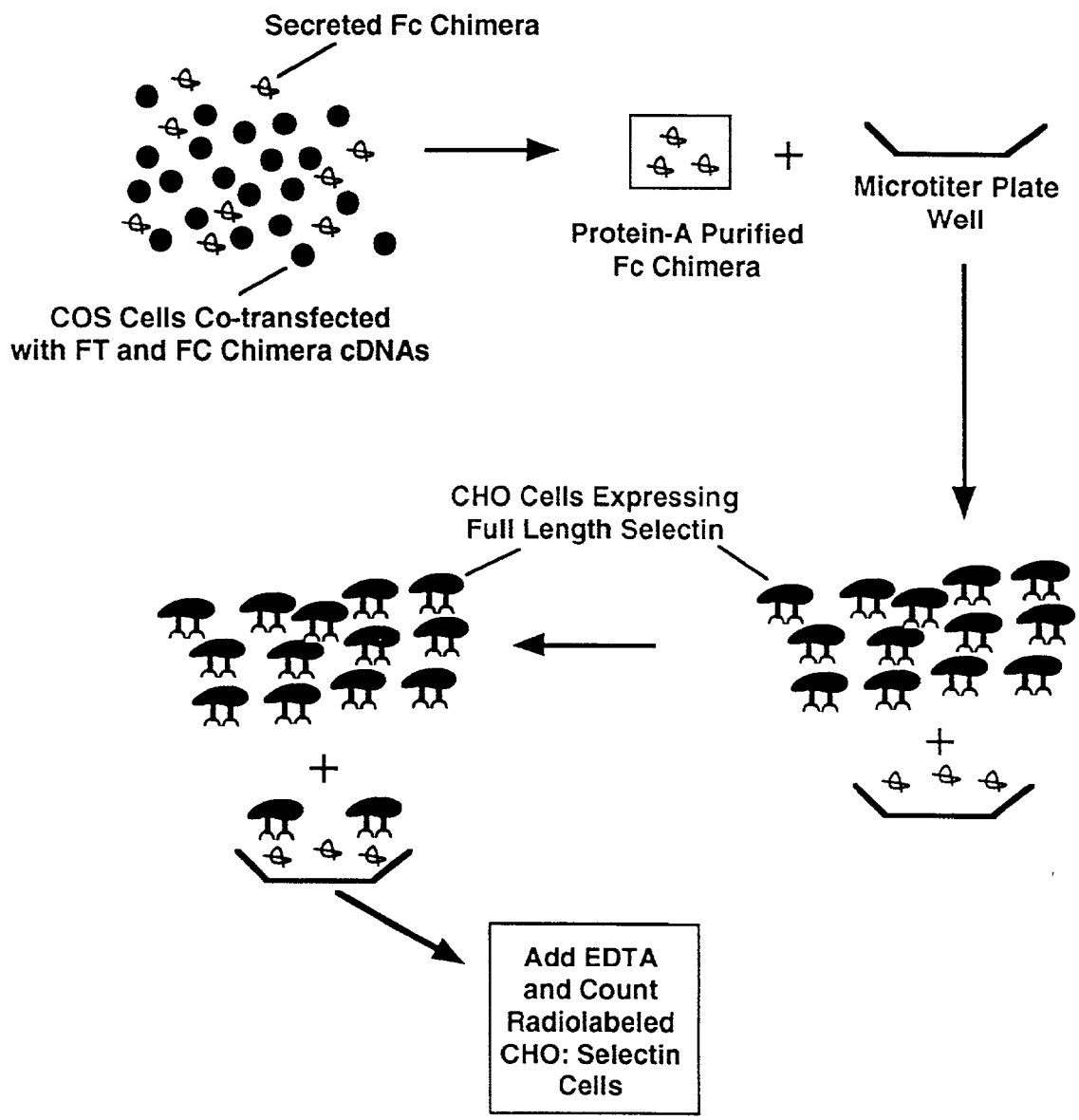
FIG. 13 is a schematic depiction of the quantitative plate binding assay of Example 4(c).

Binding of various constructs described above to cells expressing P-selectin and E-selectin was compared using a quantitative plate binding assay of Example 4(c) (which is schematically described in FIG. 13).

Figure 14:
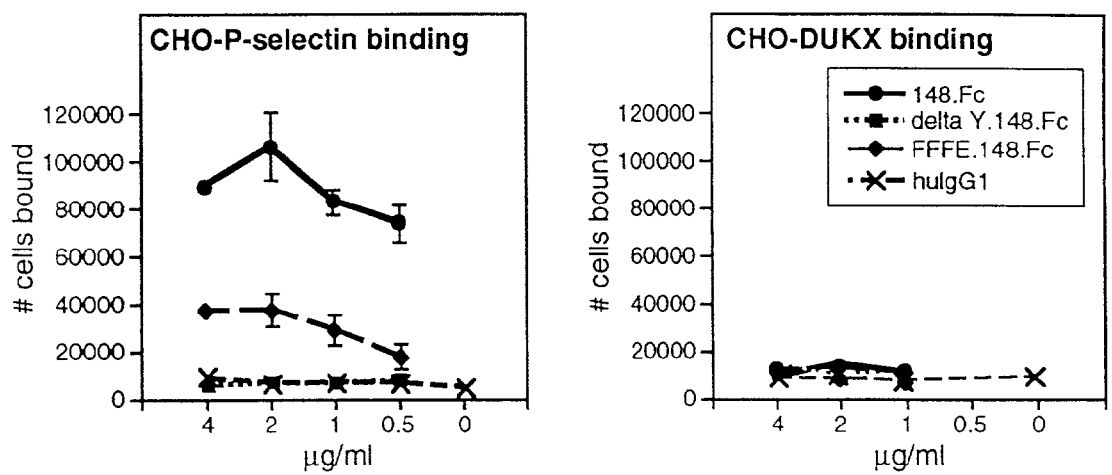

FIG. 14 compares the binding of 148.Fc, ΔY.148.Fc, FFFE.148.Fc and human IgG1 to P-selectin expressing CHO cells. Deletion of all of the tyrosine residues in the anionic region in ΔY.148.Fc eliminated binding. Changing the tyrosine residues to phenylalanine residues in FFFE.148.Fc substantially reduced binding as compared to 148.Fc. Thus, it was demonstrated that the presence of the full length anionic region is essential to P-selectin binding and that P-selectin binding is enhanced by sulfation in this region. FIG. 14 also reports control experiments demonstrating that 148.Fc, ΔY.148.Fc and FFFE.148.Fc do not bind to CHO cells which do not express selectin.

Figure 15:
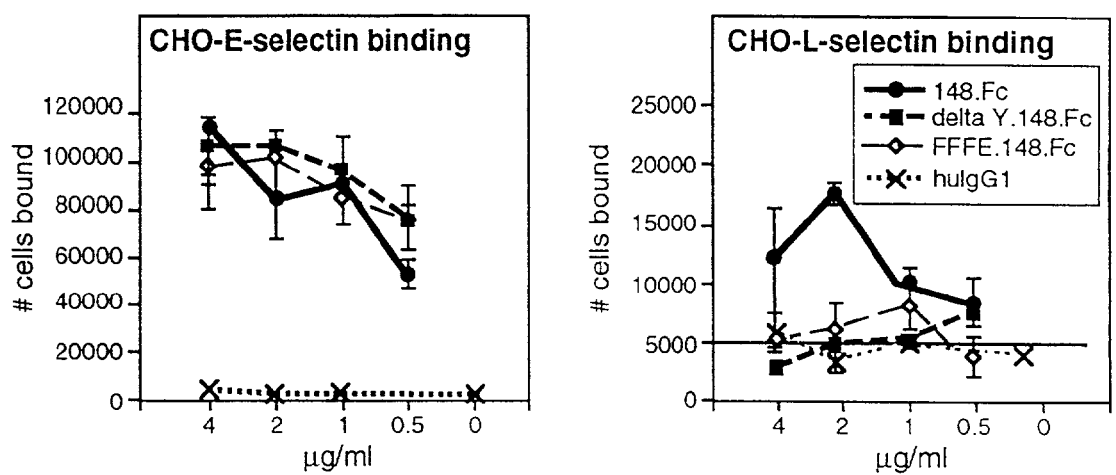

FIG. 15 compares the binding of 148.Fc, ΔY.148.Fc, FFFE.148.Fc and human IgG1 to E-selectin expressing CHO cells. E-selectin binding was unaffected by the deletions or alterations of the native sequence. Thus, it was demonstrated that the anionic region is not required for E-selectin binding.

FIG. 16 summarizes the results of FIGS. 14 and 15.

Figure 17:
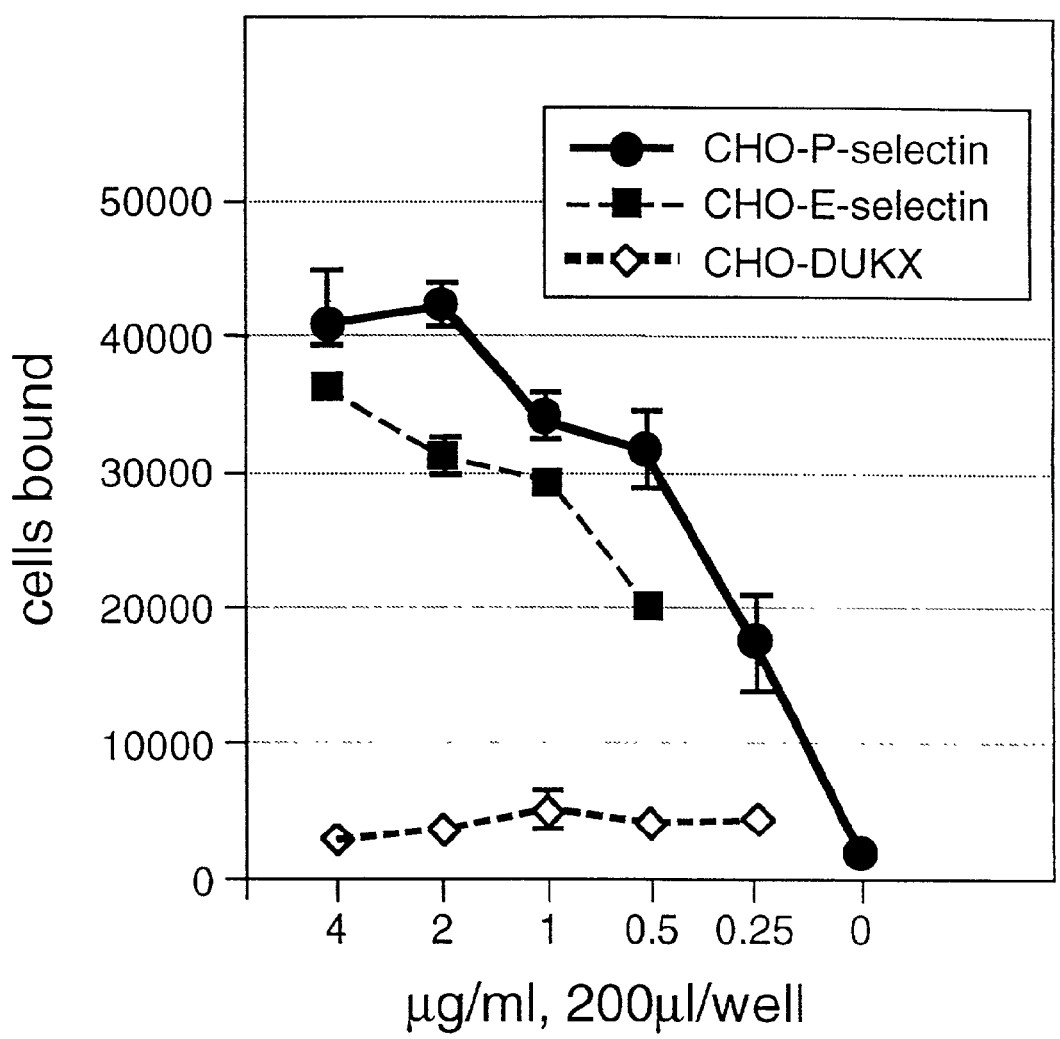
Figure 18:
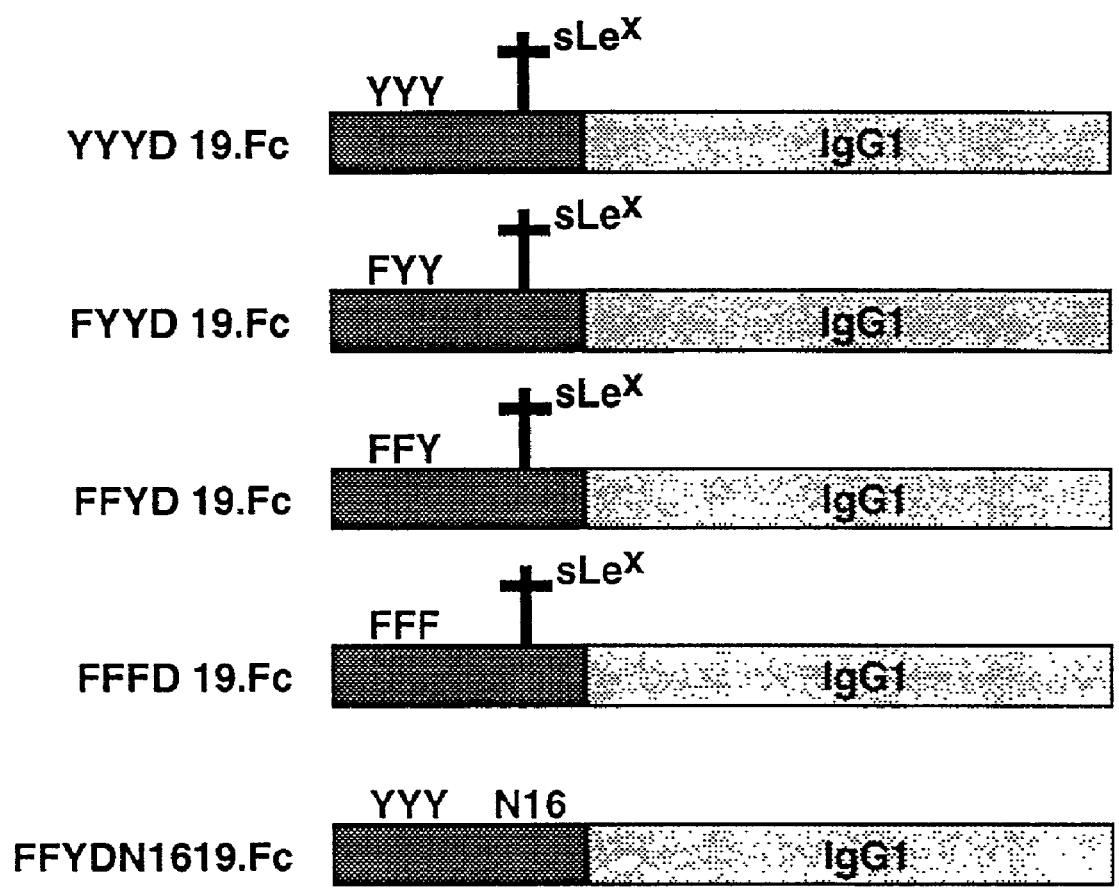
FIG. 18 is a schematic representation of several P-selectin ligand protein fragments constructed for the purpose of examining the effects of alteration of tyrosine residues in the anionic region of the P-selectin ligand proteins on selectin binding.
Figure 18:

FIG. 17 compares the binding of 47.Fc to P- and E-selectin expressing CHO cells. 47.Fc demonstrated substantial binding to both selectins despite deletion of the N-linked glycosylation sites at positions 111 and 292 of SEQ ID NO:2.

Figure 19:
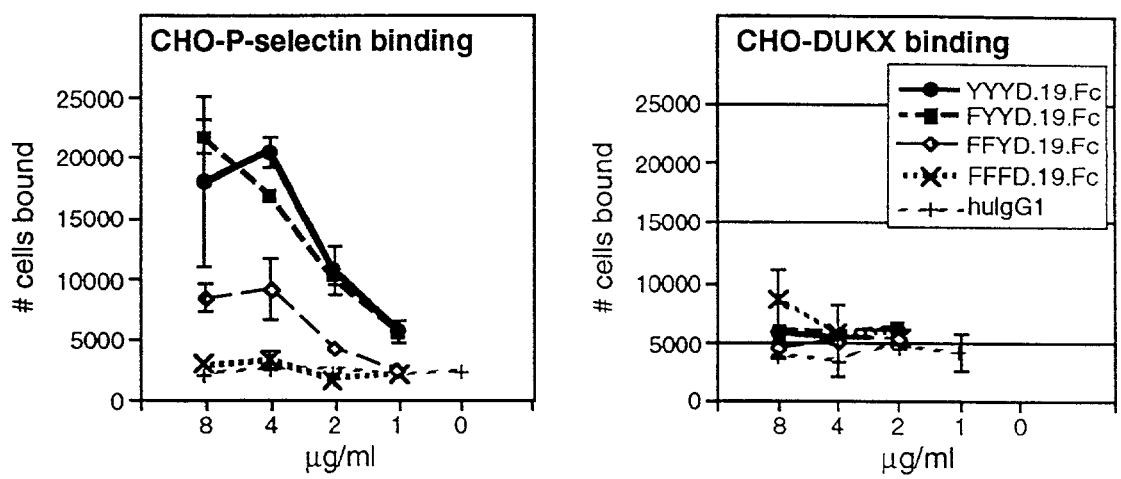

FIG. 19 compares the binding of FYYD.19.Fc, FFFD.19.Fc, H24.Q70.148.Fc, 148.Fc, and human IgG1 to P-selectin expressing CHO cells. Replacement of all of the tyrosine residues in the anionic region in FFFD.19.Fc eliminated binding. Changing the tyrosine residue at position 46 to a phenylalanine residue in FYYD.19.Fc substantially reduced binding as compared to 148.Fc. Alteration of the N-linked glycosylation sites in H24.Q70.148.Fc did not affect binding. Thus, it was demonstrated that P-selectin binding is enhanced by sulfation in the anionic region and that N-linked glycosylation is not required for P-selectin binding. FIG. 19 also reports control experiments demonstrating that FYYD.19.Fc, FFFD.19.Fc, H24.Q70.148.Fc and 148.Fc do not bind to CHO cells which do not express selectin more than human IgG1 alone.

Figure 20:
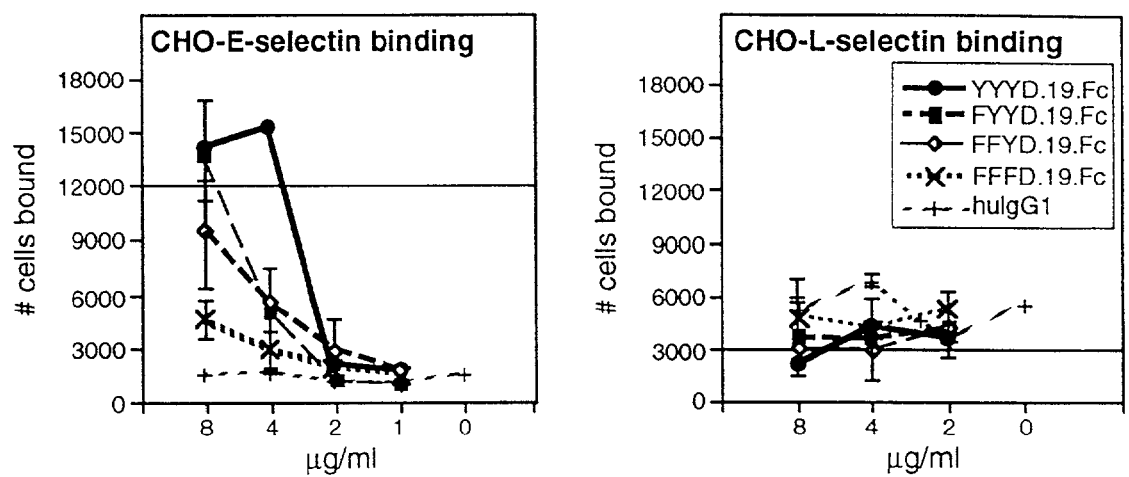

FIG. 20 compares the binding of FYYD.19.Fc, FFFD.19.Fc, H24.Q70.148.Fc, 148.Fc, and human IgG1 to E-selectin expressing CHO cells. Truncation of the ligand protein to the degree of FYYD.19.Fc and FFFD.19.Fc substantially reduced E-selectin binding. Alteration of the N-linked glycosylation sites in H24.Q70.148.Fc did not significantly affect E-selectin binding. Thus, it was demonstrated that P-selectin ligand proteins comprising amino acids 42 to 60 of SEQ ID NO:2 can selectively bind P-selectin, and, to a substantially less, extent E-selectin.

FIG. 21 summarizes the results of FIGS. 19 and 20.

G. Conclusions Regarding P- and E-Selectin Binding

Although applicants do not which to be bound by any theory, these data allow several conclusion regarding the relationship between P-selectin binding and E-selectin binding by P-selectin ligand proteins. N-linked carbohydrates are not required for binding of a P-selectin ligand protein to either P- or E-selectin. P-selectin ligand proteins as small comprising as little as amino acids 42-60 of SEQ ID NO:2 are capable of binding to P-selectin, and, to a substantially less, extent E-selectin.

Figure 22:
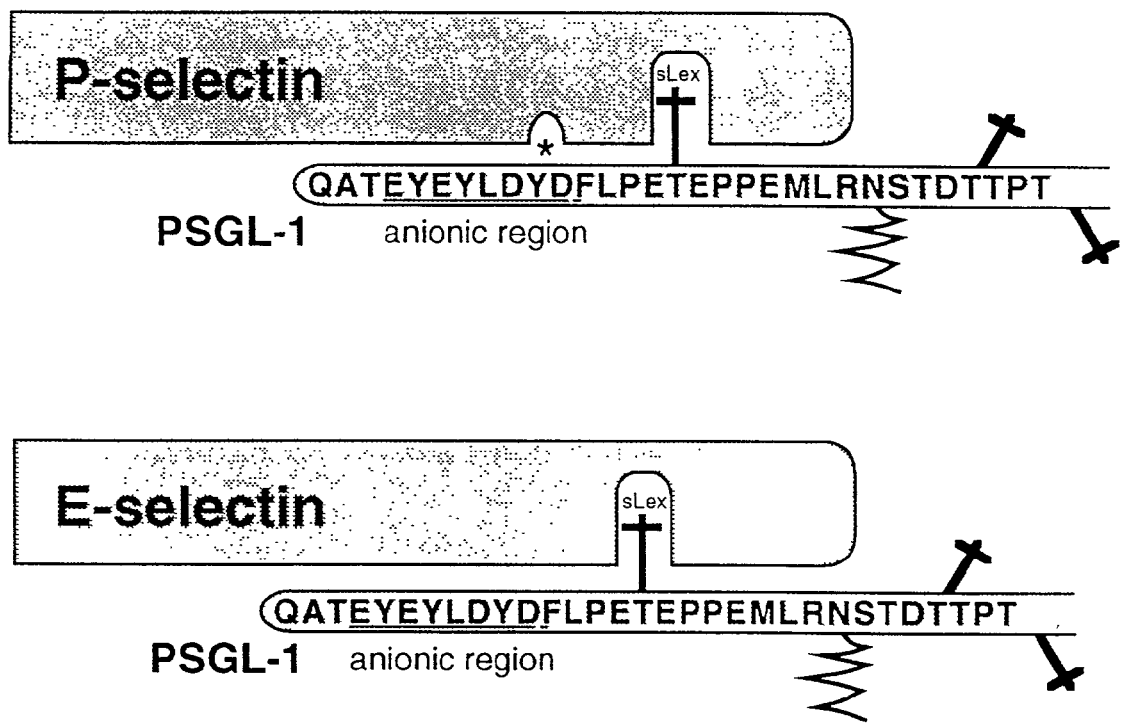
FIG. 22 depicts a proposed model for binding of P-selectin ligand proteins to P- and E-selectin.

FIG. 22 depicts a proposed schematic model for binding of P-selectin ligand proteins to P- and E-selectin. O-linked sLe$^x$ carbohydrate has been demonstrated to be required for both P- and E-selectin binding. Data presented herein demonstrate that sulfated tyrosine residues are implicated in P-selectin binding, but not E-selectin binding. Applicants' data also suggests that no N-linked glycosylation binding site is required.

EXAMPLE 11

Examination of Aggregation Phenomena and Dimer Formation in Forms of PSGL-1

A panel of PSGL-1 mutants were constructed by site-directed mutagenesis and/or PCR amplification with primers that introduced a stopcodon. The template for all mutagenesis experiments was pPL85.R16 (ATCC 75577, deposited by applicants).

The first group of mutants (C310S and C327S) encode full-length PSGL-1.R16 with only one amino acid change compared to wild-type PSGL-1.R16 (Cys to Ser at position 310 or 327, respectively). COS cells, co-transfected with pEA.3/4FT and the mutants C310S or C327S, were labeled with $^{35}$S-methionine. Cell lysates were prepared and the mutant proteins were immunoprecipitated with the P-selectin ligand polyclonal antibody of Example 7(A) and analyzed by SDS-polyacrylamide gel electrophoresis under non-reducing and reducing conditions.

The mutant C327S as well as wild-type PSGL-1.R16 migrated as a homodimer under non-reducing conditions and as a monomer under reducing conditions. In contrast, the mutant C310S migrated as a monomer both under non-reducing and reducing conditions, indicating that the cysteine at position 310 is required for dimer formation of PSGL-1.

Both mutants were also analyzed for their ability to bind to P-selectin. Detergent extracts of co-transfected COS cells were precipitated with the LEC-γ1 chimera of Example 4(A). The precipitates were analyzed by SDS-PAGE under non-reducing and reducing conditions and by autoradiography. Both PSGL-1.R16 and C327S were efficiently precipitated by LEC-g1, whereas C310S binding to LEC-γ1 was greatly reduced, indicating that the dimeric form of PSGL-1 binds P-selectin more tightly than the monomeric form.

The second set of mutants encode soluble forms of PSGL-1.R16 and are listed in Table I. The mutant ΔTM was generated by site-directed mutagenesis and has a deletion of the transmembrane domain (amino acids 313-333) followed by RLSRKA. The mutants L311, L312, A313, I314, L315, A318 and T322 were generated by site-directed mutagenesis or PCR amplication with PCR primers that introduced a stop codon in the desired position. The name of the mutant refers to the C-terminal amino acid of each truncated soluble form of PSGL-1.R 6. The mutants were analyzed according to the following criteria:
1. Expression and secretion from transfected COS cells
2. Dimer versus monomer formation
3. Lack of aggregate formation
4. P-selectin binding (LEC-γ1 chimera)

The mutants ΔTM and I316 fulfilled all four criteria. The shorter soluble forms of PSGL-1, such as sPSL.QC of Example 5(A), L311, L312, A313, I314 and L315 did not form dimers as well and the longer soluble forms of PSGL-1, such as sPSL.T7 of Example 5(C), A318 and T322 formed high molecular weight aggregates which were less desirable.

CHO cells, already expressing 3/4 fucosyltransferase and Core2 transferase, were transfected with psPSL.T7, ΔTM, I316 or psPSL.QC and amplified using methotrexate. Stable clones were isolated and labeled with $^{35}$S-methionine. Conditioned media was either analyzed directly or first precipitated with LEC-γ1 and then analyzed by SDS-PAGE under non-reducing and reducing conditions (FIG. 25). The results indicated that ΔTM and I316 were most efficient in dimer formation and P-selectin binding.

TABLE I

| Mutant | Dimer Formation | High MW Aggregates | P-selectin binding |
|---|---|---|---|
| PSL.QC | + | − | + |
| L311 | + | − | + |
| L312 | − | − | − |
| A313 | − | − | − |
| I314 | − | − | − |
| L315 | + | − | + |
| I316 | ++ | − | ++ |
| A318 | ++ | + | ++ |
| T322 | ++ | + | ++ |
| ΔTM | ++ | − | ++ |

EXAMPLE 12

Specificity of PSGL-1 Binding to P- and E-Selectins

Materials. A chimeric protein comprising the extracellular domain of human E-selectin and the Fc portion of human IgG$_1$ was constructed analogously to the P-selectin chimera, LEC-γ1, described earlier. The soluble E-selectin chimera was expressed in baculovirus-infected *Trichoplusia ni* high five cells (Invitrogen) and purified to homogeneity by Protein A Sepharose chromatography. Plasmid vectors pEA.3/4FT, pPL85, pFCD43, and pEA.sPACE, for COS expression of a(1,3/1,4)-fucosyltransferase (Fuc-TIII), PSGL-1, CD43 (leukosialin), and soluble paired basic amino acid converting enzyme (PACE), respectively, have been described herein and in the literature (Sako et al. (1993) Cell 75, 1179-1186; Rehemtulla, A. & Kaufman, R. J. (1992) *Curr. Opin. Biotechnol.* 3, 560-565; Wasley et al. (1993) J. Biol. Chem. 268, 8458-8465). Fuc-TVII cDNA (plasmid pMT.FT7) was cloned from an HL60 cDNA expression library using oligonucleotide probes derived from the published sequence (Natsuka et al. (1994) *Journal of Biological Chemistry* 269, 16789-16794; Sasaki et al. (1994) J. Biol. Chem. 269, 14730-14737). A polyclonal neutralizing rabbit antibody, Rb3443, was raised against a peptide comprising the first 15 amino acids of the mature (PACE-cleaved) N-terminus of PSGL-1. Monoclonal anti-CD43 antibodies from either Becton Dickinson or Biodesign International and isotype control antibodies were coupled to a solid support consisting of Sepharose TM-4B with a covalently attached goat affinity-purified antibody to mouse IgG (Cappel, Organon Teknika Corporation). Affinity coupling of selectin chimeras and murine antibodies to Protein A Sepharose 4 Fast Flow (Pharmacia) and to the anti-mouse IgG resin, respectively, was carried out at a ratio of 2 mg protein/ml of resin. Antiserum Rb3443 was coupled to Protein A Sepharose at 1 ml/ml resin. Coupling efficiencies, indicated by micro-BCA assay (Pierce) of the post-reacted supernatants, were at least 95%. Aprotinin and pepstatin were from Boehringer Mannheim and benzamidine, leupeptin, and phenylmethylsulfonyl fluoride (PMSF) were from Sigma.

Labeling and Membrane Extraction of Myeloid Cells. U937 or HL60 cells grown in suspension to a density of ~1.3×10$^6$ cells/ml were labeled in 50 ml of RPMI1640 medium supplemented with 10% fetal bovine serum and 2.5 mCi of $^3$H-glucosamineHCl (Dupont/NEN) for 48 hr. Activities of greater than 1 cpm/cell were routinely obtained by this technique. The labeled cells were washed with PBS, resuspended in cell lysis buffer (10 mM MOPS, 150 mM NaCl, 4 mM CaCl$_2$ and 4 mM MgCl$_2$, pH 7.5 containing protease inhibitors 20 mg/ml aprotinin, 10 mM benzamidine, 20 mg/ml leupeptin, 8 mg/ml pepstatin, and 10 mM PMSF) and subjected to several cycles of probe sonication on ice. Nuclei and cell debris were removed by low speed centrifugation and the cell membranes recovered from the supernatant by centrifugation at 100,000 g RCF for 1 hr, washed by resuspension and high speed centrifugation in cell lysis buffer containing 1 M NaCl, and finally resuspended in 3 ml membrane solubilization buffer (cell lysis buffer containing 1% Triton X-100). Several cycles of sonication and incubation on ice were employed to solubilize the membrane fraction. Finally, a low speed centrifugation step was employed to remove insoluble membrane residue.

Labeling and Membrane Extraction of Transfected COS Cells. COS M6 cells were transfected using DEAE-dextran and chloroquine (25) employing 8 µg of plasmids pPL85 or pFCD43 and 4 µg of pEA.sPACE, as well as 4 µg of pEA.3/4FT or pMT.FT7. After 40-45 hr recovery the transfected cells were starved in serum- and methionine-free DME medium for 30 min and then fed [$^{35}$S]-methionine in serum-free DME for 5 hr. The labeled cells were washed, incubated with EGTA to loosen them from the dish surface, scraped from the dish, pelleted, and suspended in cold 10 mM PIPES buffer, pH 7.5, containing 100 mM KCl, 3 mM NaCl, 3.5 mM MgCl$_2$, and protease inhibitors (see above). Membrane extraction then was carried out by sonication, low speed centrifugation, high speed centrifugation, and solubilization in membrane lysis buffer as above, for labeled myeloid cells.

Affinity Precipitations. Membrane extracts were diluted 1:4 or 1:5 with cell lysis buffer or with TBSC buffer (20 mM Tris HCl, 150 mM NaCl, 2 mM CaCl$_2$, pH 7.5) supplemented with 5 mg/ml bovine serum albumin (approximately 99%, Sigma). Extracts thus diluted to 0.2-0.25% Triton X-100 were incubated with human IgG$_1$-Protein A Sepharose with end-over-end mixing at 4° C. overnight. The precleared supernatants then were reacted for 6-12 hrs at 4° C. with Protein A Sepharose precoupled with E- or P-selectin chimeras, control human IgG$_1$, Rb3443 or with rabbit pre-immune serum or with anti-CD43 antibody or isotype control precoupled to goat anti-mouse IgG Sepharose. The resins were washed 5 or more times in buffer containing 0.1-0.5% Triton X-100 until the radioactivity of the wash supernatants was reduced to background level. Elution of proteins bound specifically to P- or E-selectin resins was accomplished with 10 mM EDTA or 5 mM EDTA/5 mM EGTA at room temperature or by boiling in SDS-PAGE sample buffer (Laemmli, U. K. (1970) Nature 227, 680-685), whereas elution of proteins bound to antibody resins was achieved exclusively by the latter means. For resolution under reducing conditions, dithiothreitol was added to the sample buffer to a final concentration of 100 mM. Samples thus prepared were resolved by SDS-PAGE on 7.5% gels, treated with En$^3$Hance (Dupont), dried, and exposed to autoradiography film.

For sequential affinity capture experiments, membrane extracts were precleared, affinity precipitated with P- or E-selectin or human IgG$_1$, and washed as above. Samples then were eluted twice from the resins with 5 mM EDTA in 10 mM MOPS, 150 mM NaCl, pH 7.5 for 1 hr at 4° C. with tumbling. The first and second eluates were combined and then immunoprecipitated with immobilized Rb3443 according to the protocols outlined above.

Results:

Soluble E- and P-selectin chimeras were used, in parallel with control human IgG$_1$ to probe detergent-solubilized membrane extracts of $^3$H-glucosamine-labeled U937 cells as described under "Methods". Examination of eluates from the immobilized selectins by SDS-PAGE/autoradiography (FIG. 26) revealed the presence in both P- and E-selectin eluates of a major protein species with identical electrophoretic properties: Mr 200-kDa non-reduced with conversion to a species of Mr 120-kDa following reduction (FIG. 26, lanes 2 and 3, respectively). Occasionally, additional bands were observed in both E- and P-selectin eluates presumably corresponding to this major band and reflecting the presence of naturally reduced material (the 120-kDa species in non-reduced samples) and incomplete reduction (the 200-kDa species in reduced samples). Additionally, a trace band of Mr 150-kDa in the E-selectin eluate which was unaffected by reduction with DTT was occasionally observed. No bands were observed in control experiments using immobilized human IgG$_1$ (FIG. 26, lane 1) or where elution of selectin resins was performed in the absence of EDTA or SDS (data not shown). Essentially identical results were obtained using HL-60 cells (data not shown). Hence, the nature of these recognition events is interpreted to be specific metal-dependant interactions of these proteins with the respective selecting, presumably via the lectin domains (Lasky, L. A. (1992) Science 258, 964-969; Drickamer, K. (1988) J. Biol. Chem. 263, 9557).

The metal-dependant recognition and electrophoretic behavior of the major band precipitated with E-selectin was consistent with the properties of the previously identified P-selectin counterreceptor, P-selectin glycoprotein ligand or PSGL-1 (Moore et al. (1994) J. Biol. Chem. 269, 23318-23327; Moore et al. (1992) J. Cell Biol. 118, 445-456; Sako et al.).

To assess whether this species was indeed PSGL-1, EDTA eluates of the both E- and P-selectin precipitates were subsequently reacted with the PSGL-1 specific polyclonal antiserum Rb3443. As shown in FIG. 27, the major band isolated by affinity capture with either selectin was immunoprecipitated using this antiserum (lanes 3 and 4, respectively). No species were detected after immunoprecipitation of the control IgG$_1$ EDTA eluate (FIG. 27, lane 5). Direct immunoprecipitations using fresh $^3$H-labeled U937 membrane extracts confirmed the specificity of Rb3443: precipitation with Rb3443 results in the recovery of a single band with the electrophoretic properties of PSGL-1 (Mr 200-kDa non-reduced, Mr 120-kDa reduced; FIG. 27, lane 2) whereas precipitation with pre-immune antiserum fails to capture any material (FIG. 27, lane 1). These results indicate that the major protein species specifically captured from myeloid cells by both E- and P-selectins is PSGL-1.

To further assess the specificity of E-selectin for PSGL-1, U937 membrane lysates were probed directly for the presence of CD43 (or leukosialin), an abundant cell surface sialoglycoprotein known to bear the major portion of myeloid cell SLe$^x$ residues (Maemura, K. & Fukuda, M. (1992) J. Biol. Chem. 267, 24379-24386). Thus, membrane extracts of $^3$H-glucosamine-labeled U937 cells were probed with an anti-CD43 antibody in parallel with the PSGL-1 specific antiserum Rb3443 and control antibodies as described under "Methods". From identical quantities of membrane lysate, the CD43 antibody precipitated in excess of 30-fold greater radioactive counts than did the PSGL-1 antiserum. Evaluation of the immunoprecipitates by SDS-PAGE/autoradiography (FIG. 28) revealed a single specific band for each antibody. Rb3443 captured a single species with the electrophoretic characteristics of PSGL-1 (FIG. 28, Lane 2). In contrast, the CD43 antibody precipitated a species with an Mr 120-kDa which was insensitive to reduction (FIG. 28, Lane 4), consistent with the absence of cysteine in CD43. Immunoprecipitations with control antibodies (FIG. 28, lanes 1 and 3) proved negative as expected. There appears to be considerably greater quantities of CD43 than PSGL-1 in U937 cells, consistent with the quantitation of these proteins in HL-60 cells (Ushiyama et al. (1993) *J. Biol. Chem.* 268, 15229-15237). Thus, the inability of E-selectin to precipitate CD43 from myeloid cells does not appear to be due to its absence in these cell lines. While we cannot exclude the possibility that E-selectin captures trace quantities of CD43 (ie., the low-intensity Mr 120-kDa band in FIG. 26, non-reduced lane 3 which is also consistent with monomeric PSGL-1), PSGL-1 appears to be the major protein precipitated from myeloid membrane extracts.

Recombinant PSGL-1 expressed in COS cells is best achieved with cotransfection of the PSGL-1 cDNA with a cDNA encoding an a(1,3/1,4) fucosyltransferase (Fuc-TIII) for P-selectin binding (Sako et al.). Interestingly, initial efforts to demonstrate E-selectin recognition of recombinant PSGL-1 failed: E-selectin was unable to capture the counter-receptor from cotransfected COS cell membrane lysates under conditions where P-selectin capture was successful. One interpretation of this result is that Fuc-TIII was able to modify recombinant PSGL-1 for recognition by P-selectin but was unable to replicate the appropriate modification(s) found in myeloid PSGL-1 necessary for E-selectin recognition. The recent cloning of a myeloid fucosyltransferase, Fuc-TVII (Natsuka et al. (1994) *Journal of Biological Chemistry* 269, 16789-16794; Sasaki et al. (1994) *J. Biol. Chem.* 269, 14730-14737), that is also capable of generating SLe$^x$ carbohydrate structures, allowed evaluation of this interpretation.

COS cells were cotransfected with cDNAs encoding either PSGL-1 or CD43 and either Fuc-TIII or Fuc-TVII. Membrane lysates were prepared from the transfected COS cells and these were precipitated with either immobilized E- or P-selectin chimeras or with antibodies to either PSGL-1 or to CD43. The precipitated products were evaluated by SDS-PAGE/autoradiography following their release by EDTA/EGTA (for selectin mediated binding) or by boiling in SDS (for immunoprecipitations). The results are shown in FIG. 29.

As observed in FIG. 29A, E-selectin capture of COS-expressed PSGL-1 was dependant upon the nature of the fucosyltransferase used in the transfection. In three separate experiments, Fuc-TVII, but not Fuc-TIII, supported PSGL-1 precipitation by E-selectin. The inability of Fuc-TIII to confer E-selectin reactivity to PSGL-1 cannot be attributed to a lack of PSGL-1 expression as the specific antiserum Rb3443 immunoprecipitated significant and comparable quantities of PSGL-1 from both Fuc-TIII and Fuc-TVII transfections (FIG. 29C). Furthermore, P-selectin was capable of precipitating equivalent quantities of PSGL-1 with either fucosyltransferase (FIG. 29B), demonstrating that Fuc-TIII and Fuc-TVII are expressed and active in these cotransfections.

Within the COS recombinant expression system as in myeloid cells, high-affinity E-selectin recognition was also dependent upon the presence of an appropriate polypeptide. Although the polypeptide length, apparent molecular weight, and high frequency and specific types of posttranslational modifications are similar in CD43 and PSGL-1 (Maemura, K. & Fukuda, M. (1992) *J. Biol. Chem.* 267, 24379-24386), neither fucosyltransferase was able to confer high-affinity E-selectin (or P-selectin) recognition to recombinant leukosialin in cotransfected COS cells (FIG. 29A). Immunoprecipitations with the anti-CD43 antibody indicate that comparable quantities of leukosialin were expressed in both Fuc-TIII and Fuc-TVII cotransfections (FIG. 29C). The failure of E-selectin to capture CD43 was not due to lack of fucosyltransferase activity within the cotransfected COS cells. FACS analysis of COS cells transfected with either PSGL-1 or CD43 and either Fuc-TIII or Fuc-TVII all show high levels of reactivity with the SLeX specific antibody CSLEX-1. Therefore, these results suggest that high-affinity E-selectin recognition requires the presence of a specific polypeptide(s) that is appropriately modified by a specific fucosyltransferase.

EXAMPLE 13

Inhibition of P-Selectin/PSGL-1 Binding by PSGL-1 Derived Peptides

A number of peptides derived from the sequence of PSGL-1 (SEQ ID NO:2) were tested for their ability to inhibit P-selectin/PSGL-1 binding. The tested peptides are listed in FIG. 30.

Inhibition was tested according to the following protocol. The wells of a 96 well plate were coated overnight at 4° C. with PSGL-1 in 50 μl of 10 mM MOPS, 150 mM NaCl, 1 mM CaCl$_2$, 1 mM MgCl at pH 7.5. After removal of the liquid from the wells, 150 μl of 10 mM MOPS, 150 mM NaCl, 1 mM CaCl$_2$, 1 mM MgCl$_2$, 0.05% tween-20, 0.05% gelatin at pH 7.5 was added per well to block the unoccupied sites. After ½ hr. to 2 hr. the block buffer was removed from the wells and 100 μl of a complex of Lec-γ1 (P-selectin-human IgG Fc chimera) (2 μg/ml), biotinylated goat anti-human antibody, and streptavidin-conjugated alkaline phosphatase (which had been allowed to tumble at room temperature for 30 minutes to 1 hour) plus any potential inhibitors were added per well. Each plate was shaken and rapped to remove the block from plate. The incubation proceeded for 1 hr at room temperature rotating in the dark. The unbound complex was washed off the plate with two 150 μl portions of 10 mM MOPS, 150 mM NaCl, 1 mM CaCl$_2$, 1 mM MgCl$_2$, 0.05% tween-20 followed by 150 μl of 1M diethanolamine, 0.5 mM MgCl$_2$. The chromogenic substrate for alkaline phosphatase, PNPP, in 10 mM DEA/0.5 mM MgCl$_2$ was added and the plate is then read at 405 nm.

The results of these assays are reported in FIG. 30. The peptides comprising amino acids 48-51 (in which the tyrosine residues have been phosphorylated) and amino acids 42-56 of SEQ ID NO:2 provided particularly desirable results.

EXAMPLE 14

Purification of a Soluble Form of PSGL-1

Substantial purification of a soluble form of P-selectin ligand protein has been achieved according to the protocol described below.

A soluble P-selectin ligand protein, 1316 (amino acid 42 to amino acid 316 of SEQ ID NO:2) was expressed in CHO cells as described herein. CHO cell conditioned media was concentrated with a Pellicon ultrafiltration membrane unit (Millipore) with either 10,000 molecular weight cutoff (MWCO) or 30,000 MWCO to about 10 times the original concentration. The buffer was then exchanged into 25 mM Tris, 1 mM CaCl$_2$, pH 7.4.

The buffer-exchanged concentrate was loaded onto a Toyopearl QAE 550C (TosoHaas) column. Alternatively, the buffer exchange step can be omitted and the concentrate can be diluted one part concentrate to three parts 25 mM Tris, 1 mM CaCl$_2$, pH 7.4, and then loaded onto the column. The column was washed with 5-10 column volumes (CV) of 25 mM Tris, 1 mM CaCl$_2$, pH 7.4 at 4° C.

The P-selectin ligand protein eluted from the column with a linear NaCl gradient (0 M NaCl to 1.0 M NaCl) in the 25 mM Tris, 1 mM CaCl$_2$, pH 7.4 buffer in approximately five column volumes. Two peaks were eluted from the column. The second peak contained the P-selectin ligand protein and was collected in bulk.

The peak from the QAE column was concentrated with a tangential flow ultrafiltration membrane (Millipore) with a 30,000 MWCO and was then buffer exchanged into 25 mM Tris, 150 mM NaCl, 1 mM CaCl$_2$, pH 7.4 at 4° C.

The buffer exchanged concentrate was loaded onto a Jacalin Agarose column overnight at 4° C. The column was washed with the diafiltration buffer and the P-selectin ligand protein was eluted with a gradient of methyl α-D-galactopyranoside (0-100 mM or)-50 mM methyl α-D-galactopyranoside) at 20° C. Fractions from the Jacalin column were analyzed by SDS-PAGE and the purest fractions were pooled.

EXAMPLE 15

P-Selectin Ligand Protein Fusions

Four fusions of a P-selectin ligand protein with a different amino acid sequence were constructed: 47.Fc, 47.AGP, 47.BMP and 47.IL11.

47.Fc: A cDNA was constructed encoding the signal peptide, PACE cleavage site and first 47 amino acids of the mature P-selectin ligand sequence fused to a mutated Fc region of human IgG1 at His224 of the native Fc sequence. The sequence of the cDNA construct is reported as SEQ ID NO:35. The fusion point is a novel NotI site at nucleotide 261. The amino acid sequence encoded by the cDNA construct is reported as SEQ ID NO:36. The mature amino acid sequence of the encoded fusion protein begins at amino acid 42 of SEQ ID NO:36. The mutations in the Fc portion were a change of Leu 234 and Gly237 of the native Fc sequence to Ala.

47.AGP: A cDNA was constructed encoding the signal peptide, PACE cleavage site and first 47 amino acids of the mature P-selectin ligand sequence fused to the first leucine residue of mature human AGP. The sequence of the EDNA construct is reported as SEQ ID NO:37. The fusion point is a novel NotI site at nucleotide 261. The amino acid sequence encoded by the cDNA construct is reported as SEQ ID NO:38. The mature amino acid sequence of the encoded fusion protein begins at amino acid 42 of SEQ ID NO:38.

47.BMP: A cDNA was constructed encoding the signal peptide, PACE cleavage site and first 47 amino acids of the mature P-selectin ligand sequence fused to the sequence of mature human BMP-2 (with its first 8 amino acids deleted). The sequence of the cDNA construct is reported as SEQ ID NO:39. The fusion point is a novel NotI site at nucleotide 261. The amino acid sequence encoded by the cDNA construct is reported as SEQ ID NO:40. The mature amino acid sequence of the encoded fusion protein begins at amino acid 42 of SEQ ID NO:40.

47.IL11: A cDNA was constructed encoding the signal peptide, PACE cleavage site and first 47 amino acids of the mature P-selectin ligand sequence fused to mature human IL-11. The sequence of the cDNA construct is reported as SEQ ID NO:41. The fusion point is a novel NotI site at nucleotide 261. The amino acid sequence encoded by the cDNA construct is reported as SEQ ID NO:42. The mature amino acid sequence of the encoded fusion protein begins at amino acid 42 of SEQ ID NO:42.

Patent and literature references cited herein are incorporated as if fully set forth.

The invention claimed is:

1. An isolated DNA encoding a fusion protein comprising (a) a first amino acid sequence comprising amino acid 42 to amino acid 60 of SEQ ID NO:2, and (b) a second amino acid sequence derived from the sequence of a protein other than P selectin ligand.

2. The DNA of claim 1 which further comprises an expression control sequence operably linked to said nucleotide sequence.

3. An isolated host cell transformed with the DNA of claim 2.

4. A process for producing a fusion protein, which comprises:
   (a) culturing the host cell of claim 3 under condition suitable for expression of the fusion protein; and
   (b) purifying the fusion protein from the culture medium.

5. The DNA of claim 1 wherein said first amino acid sequence comprises amino acid 42 to amino acid 402 of SEQ ID NO:2.

6. The DNA of claim 1 wherein said first amino acid sequence comprises amino acid 42 to amino acid 310 of SEQ ID NO:2.

7. The DNA of claim 1 wherein said first amino acid sequence comprises amino acid 42 to amino acid 88 of SEQ ID NO:2.

8. The DNA of claim 1 wherein said first amino acid sequence comprises amino acid 42 to amino acid 118 of SEQ ID NO:2.

9. The DNA of claim 1 wherein said first amino acid sequence comprises amino acid 42 to amino acid 189 of SEQ ID NO:2.

10. The DNA of claim 1 wherein said second amino acid sequence is linked to the C-terminus of said first amino acid sequence.

11. The DNA of claim 10 wherein said sequences are linked by a linking sequence.

12. The DNA of claim 1 wherein said second amino acid sequence is joined to the N-terminus of said first amino acid sequence.

13. The DNA of claim 12 wherein said sequences are linked by a linking sequence.

14. The DNA of claim 1 wherein said second amino acid sequence is an Fc portion of an antibody.

15. The DNA of claim 14, wherein the Fc portion of an antibody is from a human antibody.

16. The DNA of claim 15, wherein Leu234 and Gly237 of the Fc portion of the human antibody are changed to Ala.

* * * * *

SEQUENCE LISTING

```
<160> NUMBER OF SEQ ID NOS: 48

<210> SEQ ID NO 1
<211> LENGTH: 1649
<212> TYPE: DNA
<213> ORGANISM: Homo sapiens
<220> FEATURE:
<221> NAME/KEY: CDS
<222> LOCATION: (60)..(1268)

<400> SEQUENCE: 1
gccacttctt ctgggcccac gaggcagctg tcccatgctc tgctgagcac ggtggtgcc        59 atg cct ctg caa ctc ctc ctg ttg ctg atc cta ctg ggc cct ggc aac       107
Met Pro Leu Gln Leu Leu Leu Leu Leu Ile Leu Leu Gly Pro Gly Asn
 1               5                  10                  15 agc ttg cag ctg tgg gac acc tgg gca gat gaa gcc gag aaa gcc ttg       155
Ser Leu Gln Leu Trp Asp Thr Trp Ala Asp Glu Ala Glu Lys Ala Leu
             20                  25                  30 ggt ccc ctg ctt gcc cgg gac cgg aga cag gcc acc gaa tat gag tac       203
Gly Pro Leu Leu Ala Arg Asp Arg Arg Gln Ala Thr Glu Tyr Glu Tyr
         35                  40                  45 cta gat tat gat ttc ctg cca gaa acg gag cct cca gaa atg ctg agg       251
Leu Asp Tyr Asp Phe Leu Pro Glu Thr Glu Pro Pro Glu Met Leu Arg
     50                  55                  60 aac agc act gac acc act cct ctg act ggg cct gga acc cct gag tct       299
Asn Ser Thr Asp Thr Thr Pro Leu Thr Gly Pro Gly Thr Pro Glu Ser
 65                  70                  75                  80 acc act gtg gag cct gct gca agg cgt tct act ggc ctg gat gca gga       347
Thr Thr Val Glu Pro Ala Ala Arg Arg Ser Thr Gly Leu Asp Ala Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 85  |     |     |     |     | 90  |     |     |     |     | 95  |     |     |
| ggg | gca | gtc | aca | gag | ctg | acc | acg | gag | ctg | gcc | aac | atg | ggg | aac | ctg | 395 |
| Gly | Ala | Val | Thr | Glu | Leu | Thr | Thr | Glu | Leu | Ala | Asn | Met | Gly | Asn | Leu |     |
|     |     |     |     | 100 |     |     |     |     | 105 |     |     |     |     | 110 |     |     |
| tcc | acg | gat | tca | gca | gct | atg | gag | ata | cag | acc | act | caa | cca | gca | gcc | 443 |
| Ser | Thr | Asp | Ser | Ala | Ala | Met | Glu | Ile | Gln | Thr | Thr | Gln | Pro | Ala | Ala |     |
|     |     |     | 115 |     |     |     |     | 120 |     |     |     |     | 125 |     |     |     |
| acg | gag | gca | cag | acc | act | cca | ctg | gca | gcc | aca | gag | gca | cag | aca | act | 491 |
| Thr | Glu | Ala | Gln | Thr | Thr | Pro | Leu | Ala | Ala | Thr | Glu | Ala | Gln | Thr | Thr |     |
|     | 130 |     |     |     |     | 135 |     |     |     |     | 140 |     |     |     |     |     |
| cga | ctg | acg | gcc | acg | gag | gca | cag | acc | act | cca | ctg | gca | gcc | aca | gag | 539 |
| Arg | Leu | Thr | Ala | Thr | Glu | Ala | Gln | Thr | Thr | Pro | Leu | Ala | Ala | Thr | Glu |     |
| 145 |     |     |     |     | 150 |     |     |     |     | 155 |     |     |     |     | 160 |     |
| gca | cag | acc | act | cca | cca | gca | gcc | acg | gaa | gca | cag | acc | act | caa | ccc | 587 |
| Ala | Gln | Thr | Thr | Pro | Pro | Ala | Ala | Thr | Glu | Ala | Gln | Thr | Thr | Gln | Pro |     |
|     |     |     |     | 165 |     |     |     |     | 170 |     |     |     |     | 175 |     |     |
| aca | ggc | ctg | gag | gca | cag | acc | act | gca | cca | gca | gcc | atg | gag | gca | cag | 635 |
| Thr | Gly | Leu | Glu | Ala | Gln | Thr | Thr | Ala | Pro | Ala | Ala | Met | Glu | Ala | Gln |     |
|     |     |     | 180 |     |     |     |     | 185 |     |     |     |     | 190 |     |     |     |
| acc | act | gca | cca | gca | gcc | atg | gaa | gca | cag | acc | act | cca | cca | gca | gcc | 683 |
| Thr | Thr | Ala | Pro | Ala | Ala | Met | Glu | Ala | Gln | Thr | Thr | Pro | Pro | Ala | Ala |     |
|     | 195 |     |     |     |     | 200 |     |     |     |     | 205 |     |     |     |     |     |
| atg | gag | gca | cag | acc | act | caa | acc | aca | gcc | atg | gag | gca | cag | acc | act | 731 |
| Met | Glu | Ala | Gln | Thr | Thr | Gln | Thr | Thr | Ala | Met | Glu | Ala | Gln | Thr | Thr |     |
| 210 |     |     |     |     | 215 |     |     |     |     | 220 |     |     |     |     |     |     |
| gca | cca | gaa | gcc | acg | gag | gca | cag | acc | act | caa | ccc | aca | gcc | acg | gag | 779 |
| Ala | Pro | Glu | Ala | Thr | Glu | Ala | Gln | Thr | Thr | Gln | Pro | Thr | Ala | Thr | Glu |     |
| 225 |     |     |     | 230 |     |     |     |     | 235 |     |     |     |     | 240 |     |     |
| gca | cag | acc | act | cca | ctg | gca | gcc | atg | gag | gcc | ctg | tcc | aca | gaa | ccc | 827 |
| Ala | Gln | Thr | Thr | Pro | Leu | Ala | Ala | Met | Glu | Ala | Leu | Ser | Thr | Glu | Pro |     |
|     |     |     |     | 245 |     |     |     |     | 250 |     |     |     |     | 255 |     |     |
| agt | gcc | aca | gag | gcc | ctg | tcc | atg | gaa | cct | act | acc | aaa | aga | ggt | ctg | 875 |
| Ser | Ala | Thr | Glu | Ala | Leu | Ser | Met | Glu | Pro | Thr | Thr | Lys | Arg | Gly | Leu |     |
|     |     | 260 |     |     |     |     | 265 |     |     |     |     | 270 |     |     |     |     |
| ttc | ata | ccc | ttt | tct | gtg | tcc | tct | gtt | act | cac | aag | ggc | att | ccc | atg | 923 |
| Phe | Ile | Pro | Phe | Ser | Val | Ser | Ser | Val | Thr | His | Lys | Gly | Ile | Pro | Met |     |
|     |     | 275 |     |     |     |     | 280 |     |     |     |     | 285 |     |     |     |     |
| gca | gcc | agc | aat | ttg | tcc | gtc | aac | tac | cca | gtg | ggg | gcc | cca | gac | cac | 971 |
| Ala | Ala | Ser | Asn | Leu | Ser | Val | Asn | Tyr | Pro | Val | Gly | Ala | Pro | Asp | His |     |
|     | 290 |     |     |     |     | 295 |     |     |     |     | 300 |     |     |     |     |     |
| atc | tct | gtg | aag | cag | tgc | ctg | ctg | gcc | atc | cta | atc | ttg | gcg | ctg | gtg | 1019 |
| Ile | Ser | Val | Lys | Gln | Cys | Leu | Leu | Ala | Ile | Leu | Ile | Leu | Ala | Leu | Val |     |
| 305 |     |     |     |     | 310 |     |     |     |     | 315 |     |     |     |     | 320 |     |
| gcc | act | atc | ttc | ttc | gtg | tgc | act | gtg | gtg | ctg | gcg | gtc | cgc | ctc | tcc | 1067 |
| Ala | Thr | Ile | Phe | Phe | Val | Cys | Thr | Val | Val | Leu | Ala | Val | Arg | Leu | Ser |     |
|     |     |     |     | 325 |     |     |     |     | 330 |     |     |     |     | 335 |     |     |
| cgc | aag | ggc | cac | atg | tac | ccc | gtg | cgt | aat | tac | tcc | ccc | acc | gag | atg | 1115 |
| Arg | Lys | Gly | His | Met | Tyr | Pro | Val | Arg | Asn | Tyr | Ser | Pro | Thr | Glu | Met |     |
|     |     |     | 340 |     |     |     |     | 345 |     |     |     |     | 350 |     |     |     |
| gtc | tgc | atc | tca | tcc | ctg | ttg | cct | gat | ggg | ggt | gag | ggg | ccc | tct | gcc | 1163 |
| Val | Cys | Ile | Ser | Ser | Leu | Leu | Pro | Asp | Gly | Gly | Glu | Gly | Pro | Ser | Ala |     |
|     |     | 355 |     |     |     |     | 360 |     |     |     |     | 365 |     |     |     |     |
| aca | gcc | aat | ggg | ggc | ctg | tcc | aag | gcc | aag | agc | ccg | ggc | ctg | acg | cca | 1211 |
| Thr | Ala | Asn | Gly | Gly | Leu | Ser | Lys | Ala | Lys | Ser | Pro | Gly | Leu | Thr | Pro |     |
|     | 370 |     |     |     |     | 375 |     |     |     |     | 380 |     |     |     |     |     |
| gag | ccc | agg | gag | gac | cgt | gag | ggg | gat | gac | ctc | acc | ctg | cac | agc | ttc | 1259 |
| Glu | Pro | Arg | Glu | Asp | Arg | Glu | Gly | Asp | Asp | Leu | Thr | Leu | His | Ser | Phe |     |
| 385 |     |     |     |     | 390 |     |     |     |     | 395 |     |     |     |     | 400 |     |
| ctc | cct | tag | ctcactctgc | catctgtttt | ggcaagaccc | cacctccacg |     |     |     |     |     |     |     |     |     | 1308 |
| Leu | Pro |     |     |     |     |     |     |     |     |     |     |     |     |     |     |     |

```
ggctctcctg ggccaccct gagtgcccag accccaatcc acagctctgg gcttcctcgg    1368
agacccctgg ggatggggat cttcagggaa ggaactctgg ccacccaaac aggacaagag    1428
cagcctgggg ccaagcagac gggcaagtgg agccacctct ttcctccctc cgcggatgaa    1488
gcccagccac atttcagccg aggtccaagg caggaggcca tttacttgag acagattctc    1548
tcctttttcc tgtcccccat cttctctggg tccctctaac atctcccatg ctctccccg    1608 cttctcctgg tcactggagt ctcctcccca tgtacccaag g                       1649

<210> SEQ ID NO 2
<211> LENGTH: 402
<212> TYPE: PRT
<213> ORGANISM: Homo sapiens

<400> SEQUENCE: 2

Met Pro Leu Gln Leu Leu Leu Leu Ile Leu Leu Gly Pro Gly Asn
  1               5                  10                  15

Ser Leu Gln Leu Trp Asp Thr Trp Ala Asp Glu Ala Glu Lys Ala Leu
                 20                  25                  30

Gly Pro Leu Leu Ala Arg Asp Arg Arg Gln Ala Thr Glu Tyr Glu Tyr
             35                  40                  45

Leu Asp Tyr Asp Phe Leu Pro Glu Thr Glu Pro Pro Glu Met Leu Arg
         50                  55                  60

Asn Ser Thr Asp Thr Thr Pro Leu Thr Gly Pro Gly Thr Pro Glu Ser
 65                  70                  75                  80

Thr Thr Val Glu Pro Ala Ala Arg Arg Ser Thr Gly Leu Asp Ala Gly
                 85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125

Thr Glu Ala Gln Thr Thr Pro Leu Ala Ala Thr Glu Ala Gln Thr Thr
    130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
            180                 185                 190

Thr Thr Ala Pro Ala Ala Met Glu Ala Gln Thr Thr Pro Pro Ala Ala
        195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Thr Gln Pro Thr Ala Thr Glu
225                 230                 235                 240

Ala Gln Thr Thr Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
            260                 265                 270

Phe Ile Pro Phe Ser Val Ser Ser Val Thr His Lys Gly Ile Pro Met
        275                 280                 285

Ala Ala Ser Asn Leu Ser Val Asn Tyr Pro Val Gly Ala Pro Asp His
    290                 295                 300

Ile Ser Val Lys Gln Cys Leu Leu Ala Ile Leu Ile Leu Ala Leu Val
305                 310                 315                 320
```

```
Ala Thr Ile Phe Phe Val Cys Thr Val Leu Ala Val Arg Leu Ser
                325                 330                 335

Arg Lys Gly His Met Tyr Pro Val Arg Asn Tyr Ser Pro Thr Glu Met
            340                 345                 350

Val Cys Ile Ser Ser Leu Leu Pro Asp Gly Gly Glu Gly Pro Ser Ala
            355                 360                 365

Thr Ala Asn Gly Gly Leu Ser Lys Ala Lys Ser Pro Gly Leu Thr Pro
370                 375                 380

Glu Pro Arg Glu Asp Arg Glu Gly Asp Asp Leu Thr Leu His Ser Phe
385                 390                 395                 400

Leu Pro

<210> SEQ ID NO 3
<211> LENGTH: 1239
<212> TYPE: DNA
<213> ORGANISM: Homo sapiens
<220> FEATURE:
<221> NAME/KEY: CDS
<222> LOCATION: (1)..(1239)

<400> SEQUENCE: 3 atg cct ctg caa ctc ctc ctg ttg ctg atc cta ctg ggc cct ggc aac     48
Met Pro Leu Gln Leu Leu Leu Leu Ile Leu Leu Gly Pro Gly Asn
 1               5                  10                  15 agc ttg cag ctg tgg gac acc tgg gca gat gaa gcc gag aaa gcc ttg     96
Ser Leu Gln Leu Trp Asp Thr Trp Ala Asp Glu Ala Glu Lys Ala Leu
                20                  25                  30 ggt ccc ctg ctt gcc cgg gac cgg aga cag gcc acc gaa tat gag tac    144
Gly Pro Leu Leu Ala Arg Asp Arg Arg Gln Ala Thr Glu Tyr Glu Tyr
            35                  40                  45 cta gat tat gat ttc ctg cca gaa acg gag cct cca gaa atg ctg agg    192
Leu Asp Tyr Asp Phe Leu Pro Glu Thr Glu Pro Pro Glu Met Leu Arg
         50                  55                  60 aac agc act gac acc act cct ctg act ggg cct gga acc cct gag tct    240
Asn Ser Thr Asp Thr Thr Pro Leu Thr Gly Pro Gly Thr Pro Glu Ser
 65                  70                  75                  80 acc act gtg gag cct gct gca agg cgt tct act ggc ctg gat gca gga    288
Thr Thr Val Glu Pro Ala Ala Arg Arg Ser Thr Gly Leu Asp Ala Gly
                 85                  90                  95 ggg gca gtc aca gag ctg acc acg gag ctg gcc aac atg ggg aac ctg    336
Gly Ala Val Thr Glu Leu Thr Thr Glu Leu Ala Asn Met Gly Asn Leu
            100                 105                 110 tcc acg gat tca gca gct atg gag ata cag acc act caa cca gca gcc    384
Ser Thr Asp Ser Ala Ala Met Glu Ile Gln Thr Thr Gln Pro Ala Ala
        115                 120                 125 acg gag gca cag acc act caa cca gtg ccc acg gag gca cag acc act    432
Thr Glu Ala Gln Thr Thr Gln Pro Val Pro Thr Glu Ala Gln Thr Thr
    130                 135                 140 cca ctg gca gcc aca gag gca cag aca act cga ctg acg gcc acg gag    480
Pro Leu Ala Ala Thr Glu Ala Gln Thr Thr Arg Leu Thr Ala Thr Glu
145                 150                 155                 160 gca cag acc act cca ctg gca gcc aca gag gca cag acc act cca cca    528
Ala Gln Thr Thr Pro Leu Ala Ala Thr Glu Ala Gln Thr Thr Pro Pro
                165                 170                 175 gca gcc acg gaa gca cag acc act caa ccc aca ggc ctg gag gca cag    576
Ala Ala Thr Glu Ala Gln Thr Thr Gln Pro Thr Gly Leu Glu Ala Gln
            180                 185                 190 acc act gca cca gca gcc atg gag gca cag acc act gca cca gca gcc    624
Thr Thr Ala Pro Ala Ala Met Glu Ala Gln Thr Thr Ala Pro Ala Ala
        195                 200                 205
```

-continued

```
atg gaa gca cag acc act cca cca gca gcc atg gag gca cag acc act    672
Met Glu Ala Gln Thr Thr Pro Pro Ala Ala Met Glu Ala Gln Thr Thr
210                 215                 220 caa acc aca gcc atg gag gca cag acc act gca cca gaa gcc acg gag    720
Gln Thr Thr Ala Met Glu Ala Gln Thr Thr Ala Pro Glu Ala Thr Glu
225                 230                 235                 240 gca cag acc act caa ccc aca gcc acg gag gca cag acc act cca ctg    768
Ala Gln Thr Thr Gln Pro Thr Ala Thr Glu Ala Gln Thr Thr Pro Leu
                245                 250                 255 gca gcc atg gag gcc ctg tcc aca gaa ccc agt gcc aca gag gcc ctg    816
Ala Ala Met Glu Ala Leu Ser Thr Glu Pro Ser Ala Thr Glu Ala Leu
            260                 265                 270 tcc atg gaa cct act acc aaa aga ggt ctg ttc ata ccc ttt tct gtg    864
Ser Met Glu Pro Thr Thr Lys Arg Gly Leu Phe Ile Pro Phe Ser Val
        275                 280                 285 tcc tct gtt act cac aag ggc att ccc atg gca gcc agc aat ttg tcc    912
Ser Ser Val Thr His Lys Gly Ile Pro Met Ala Ala Ser Asn Leu Ser
    290                 295                 300 gtc aac tac cca gtg ggg gcc cca gac cac atc tct gtg aag cag tgc    960
Val Asn Tyr Pro Val Gly Ala Pro Asp His Ile Ser Val Lys Gln Cys
305                 310                 315                 320 ctg ctg gcc atc cta atc ttg gcg ctg gtg gcc act atc ttc ttc gtg   1008
Leu Leu Ala Ile Leu Ile Leu Ala Leu Val Ala Thr Ile Phe Phe Val
                325                 330                 335 tgc act gtg gtg ctg gcg gtc cgc ctc tcc cgc aag ggc cac atg tac   1056
Cys Thr Val Val Leu Ala Val Arg Leu Ser Arg Lys Gly His Met Tyr
            340                 345                 350 ccc gtg cgt aat tac tcc ccc acc gag atg gtc tgc atc tca tcc ctg   1104
Pro Val Arg Asn Tyr Ser Pro Thr Glu Met Val Cys Ile Ser Ser Leu
        355                 360                 365 ttg cct gat ggg ggt gag ggg ccc tct gcc aca gcc aat ggg ggc ctg   1152
Leu Pro Asp Gly Gly Glu Gly Pro Ser Ala Thr Ala Asn Gly Gly Leu
    370                 375                 380 tcc aag gcc aag agc ccg ggc ctg acg cca gag ccc agg gag gac cgt   1200
Ser Lys Ala Lys Ser Pro Gly Leu Thr Pro Glu Pro Arg Glu Asp Arg
385                 390                 395                 400 gag ggg gat gac ctc acc ctg cac agc ttc ctc cct tag                1239
Glu Gly Asp Asp Leu Thr Leu His Ser Phe Leu Pro
                405                 410
```

<210> SEQ ID NO 4
<211> LENGTH: 412
<212> TYPE: PRT
<213> ORGANISM: Homo sapiens

<400> SEQUENCE: 4

```
Met Pro Leu Gln Leu Leu Leu Leu Ile Leu Leu Gly Pro Gly Asn
  1               5                  10                  15

Ser Leu Gln Leu Trp Asp Thr Trp Ala Asp Glu Ala Glu Lys Ala Leu
                 20                  25                  30

Gly Pro Leu Leu Ala Arg Asp Arg Arg Gln Ala Thr Glu Tyr Glu Tyr
             35                  40                  45

Leu Asp Tyr Asp Phe Leu Pro Glu Thr Glu Pro Pro Glu Met Leu Arg
        50                  55                  60

Asn Ser Thr Asp Thr Thr Pro Leu Thr Gly Pro Gly Thr Pro Glu Ser
 65                  70                  75                  80

Thr Thr Val Glu Pro Ala Ala Arg Arg Ser Thr Gly Leu Asp Ala Gly
                 85                  90                  95

Gly Ala Val Thr Glu Leu Thr Thr Glu Leu Ala Asn Met Gly Asn Leu
```

```
                        100                 105                 110
Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
        130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
            165                 170                 175

Ala Ala Thr Glu Ala Gln Thr Thr Gln Pro Thr Gly Leu Glu Ala Gln
        180                 185                 190

Thr Thr Ala Pro Ala Ala Met Glu Ala Gln Thr Thr Ala Pro Ala Ala
            195                 200                 205

Met Glu Ala Gln Thr Thr Pro Pro Ala Ala Met Glu Ala Gln Thr Thr
        210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
            245                 250                 255

Ala Ala Met Glu Ala Leu Ser Thr Glu Pro Ser Ala Thr Glu Ala Leu
        260                 265                 270

Ser Met Glu Pro Thr Thr Lys Arg Gly Leu Phe Ile Pro Phe Ser Val
            275                 280                 285

Ser Ser Val Thr His Lys Gly Ile Pro Met Ala Ala Ser Asn Leu Ser
        290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
            325                 330                 335

Cys Thr Val Val Leu Ala Val Arg Leu Ser Arg Lys Gly His Met Tyr
        340                 345                 350

Pro Val Arg Asn Tyr Ser Pro Thr Glu Met Val Cys Ile Ser Ser Leu
            355                 360                 365

Leu Pro Asp Gly Gly Glu Gly Pro Ser Ala Thr Ala Asn Gly Gly Leu
        370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
            405                 410

<210> SEQ ID NO 5
<211> LENGTH: 2151
<212> TYPE: DNA
<213> ORGANISM: Homo sapiens

<400> SEQUENCE: 5
atggagctga ggccctggtt gctatgggtg gtagcagcaa caggaacctt ggtcctgcta      60
gcagctgatg ctcagggcca gaaggtcttc accaacacgt gggctgtgcg catccctgga     120
ggcccagcgg tggccaacag tgtggcacgg aagcatgggt cctcaacct gggccagatc      180 ttcgggact attaccactt ctggcatcga ggagtgacga agcggcccct gtcgcctcac      240
cgcccgcggc acagccggct gcagagggag cctcaagtac agtggctgga cagcaggtg      300 gcaaagcgac ggactaaacg ggacgtgtac caggagccca gaccccaa gtttcctcag      360 cagtggtacc tgtctggtgt cactcagcgg gacctgaatg tgaaggcggc ctgggcgcag     420
```

| | |
|---|---|
| ggctacacag ggcacggcat tgtggtctcc attctggacg atggcatcga agaaccac | 480 |
| ccggacttgg caggcaatta tgatcctggg gccagttttg atgtcaatga ccaggaccct | 540 |
| gaccccagc ctcggtacac acagatgaat gacaacaggc acggcacacg gtgtgcgggg | 600 |
| gaagtggctg cggtggccaa caacggtgtc tgtggtgtag gtgtggccta caacgcccgc | 660 |
| attggagggg tgcgcatgct ggatggcgag gtgacagatg cagtggaggc acgctcgctg | 720 |
| ggcctgaacc ccaaccacat ccacatctac agtgccagct ggggccccga ggatgacggc | 780 |
| aagacagtgg atgggccagc ccgcctcgcc gaggaggcct tcttccgtgg ggttagccag | 840 |
| ggccgagggg ggctgggctc catctttgtc tgggcctcgg ggaacggggg ccgggaacat | 900 |
| gacagctgca actgcgacgg ctacaccaac agtatctaca cgctgtccat cagcagcgcc | 960 |
| acgcagtttg gcaacgtgcc gtggtacagc gaggcctgct cgtccacact ggccacgacc | 1020 |
| tacagcagtg gcaaccagaa tgagaagcag atcgtgacga ctgacttgcg gcagaagtgc | 1080 |
| acggagtctc acacgggcac ctcagcctct gccccttag cagccggcat cattgctctc | 1140 |
| accctggagg ccaataagaa cctcacatgg cgggacatgc aacacctggt ggtacagacc | 1200 |
| tcgaagccag cccacctcaa tgccaacgac tgggccacca atggtgtggg ccggaaaagtg | 1260 |
| agccactcat atggctacgg gcttttggac gcaggcgcca tggtggccct ggcccagaat | 1320 |
| tggaccacag tggccccca gcggaagtgc atcatcgaca tcctcaccga gcccaaagac | 1380 |
| atcgggaaac ggctcgaggt gcggaagacc gtgaccgcgt gcctgggcga gcccaaccac | 1440 |
| atcactcggc tggagcacgc tcaggcgcgg ctcaccctgt cctataatcg ccgtggcgac | 1500 |
| ctggccatcc acctggtcag ccccatgggc acccgctcca cctgctggc agccaggcca | 1560 |
| catgactact ccgcagatgg gtttaatgac tgggccttca tgacaactca ttcctgggat | 1620 |
| gaggatccct ctggcgagtg ggtcctagag attgaaaaca ccagcgaagc caacaactat | 1680 |
| gggacgctga ccaagttcac cctcgtactc tatggcaccg ccctgagggg ctgcccgta | 1740 |
| cctccagaaa gcagtggctg caagaccctc acgtccagtc aggcctgtgt ggtgtgcgag | 1800 |
| gaaggcttct ccctgcacca gaagagctgt gtccagcact gccctccagg cttcgccccc | 1860 |
| caagtcctcg atacgcacta tagcaccgag aatgacgtgg agaccatccg ggccagcgtc | 1920 |
| tgcgccccct gccacgcctc atgtgccaca tgccagggc cggccctgac agactgcctc | 1980 |
| agctgcccca gccacgcctc cttggaccct gtggagcaga cttgctcccg gcaaagccag | 2040 |
| agcagccgag agtccccgcc acagcagcag ccacctcggc tgccccggga ggtggaggcg | 2100 |
| gggcaacggc tgcgggcagg gctgctgccc tcacacctgc ctgagtgatg a | 2151 |

<210> SEQ ID NO 6
<211> LENGTH: 1587
<212> TYPE: DNA
<213> ORGANISM: Homo sapiens

<400> SEQUENCE: 6

| | |
|---|---|
| atgcctctgc aactcctcct gttgctgatc ctactgggcc ctggcaacag cttgcagctg | 60 |
| tgggacacct gggcagatga agccgagaaa gccttgggtc cctgcttgc ccgggaccgg | 120 |
| agacaggcca ccgaatatga gtacctagat tatgatttcc tgccagaaac ggagcctcca | 180 |
| gaaatgctga ggaacagcac tgacaccact cctctgactg ggcctggaac ccctgagtct | 240 |
| accactgtgg agcctgctgc aaggcgttct actggcctgg atgcaggagg ggcagtcaca | 300 |
| gagctgacca cggagctggc caacatgggg aacctgtcca cggattcagc agctatggag | 360 |
| atacagacca ctcaaccagc agccacggag gcacagacca ctccactggc agccacagag | 420 |

```
gcacagacaa ctcgactgac ggccacggag gcacagacca ctccactggc agccacagag      480
gcacagacca ctccaccagc agccacggaa gcacagacca ctcaacccac aggcctggag      540
gcacagacca ctgcaccagc agccatggag gcacagacca ctgcaccagc agccatggaa      600
gcacagacca ctccaccagc agccatggag gcacagacca ctcaaaccac agccatggag      660
gcacagacca ctgcaccaga gccacggag gcacagacca ctcaacccac agccacggag       720
gcacagacca ctccactggc agccatggag gccctgtcca cagaacccag tgccacagag      780
gccctgtcca tggaacctac taccaaaaga ggtctgttca tacccttttc tgtgtcctct      840
gttactcaca agggcattcc catggcagcc agcaatttgt ccgtcctgcg gccgcagtct      900
agagacaaaa ctcacacatg cccaccgtgc ccagcacctg aactcctggg gggaccgtca      960
gtcttcctct tccccccaaa acccaaggac accctcatga tctcccggac ccctgaggtc     1020
acatgcgtgg tggtggacgt gagccacgaa gaccctgagg tcaagttcaa ctggtacgtg     1080
gacggcgtgg aggtgcataa tgccaagaca aagccgcggg aggagcagta caacagcacg     1140
taccgtgtgg tcagcgtcct caccgtcctg caccaggact ggctgaatgg caaggagtac     1200
aagtgcaagg tctccaacaa agccctccca gtccccatcg agaaaaccat ctccaaagcc     1260
aaagggcagc cccgagaacc acaggtgtac accctgcccc catcccggga ggagatgacc     1320
aagaaccagg tcagcctgac ctgcctggtc aaaggcttct atcccagcga catcgccgtg     1380
gagtgggaga gcaatgggca gccggagaac aactacaaga ccacgcctcc cgtgctggac     1440
tccgacggct ccttcttcct ctatagcaag ctcaccgtgg acaagagcag gtggcagcag     1500
gggaacgtct tctcatgctc cgtgatgcat gaggctctgc acaaccacta cacgcagaag     1560
agcctctccc tgtccccggg taaatag                                         1587
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattccgtcg actctagag                                                  19

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctctagagtc gacgg                                                      15

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tagcatacgc tctagagcat ggatcccctg ggtgcagcca agc                       43

```
<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccggaattct caggtgaacc aagccgc                                          27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aagtatctgt ccagggcttc caggt                                            25

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aactacccag tgggagcacc agaccacatc tctgtgaagc agtgctag                   48

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aattctagca ctgcttcaca gagatgtggt ctggtgctcc cactgggtag tt              52

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aactacccag tgggagcacc agaccacatc tctgtgaagc agtag                      45

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattctactg cttcacagag atgtggtctg gtgctcccac tgggtagtt                  49

<210> SEQ ID NO 16
```

```
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctagacccgg gatggcatcc atgacaggag gacaacaaat ggtaggccgt ag           52

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aattctacgg cctacccatt tgttgtcctc ctgtcatgga tgccatcccg ggt          53

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctgcggccgc agt                                                     13

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctagactgcg gccgcag                                                 17

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccaggtccaa ctgcaggtcg actctagagg gcacttcttc tgggcccacg             50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tattatctgt gcggccgccc tccagaaccc atggctgctg gttgcagtgg             50

<210> SEQ ID NO 22
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 22
tattatctgt gcggccgcgc agcaggctcc acagtggtag                          40

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tattatctgt gcggccgcgg aggctccgtt tctggcag                            38

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggagacagg ccaccgaatt cctgccagaa acg                                 33

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cctccagaaa tgctgaggca cagcactgac accactcctc                          40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gagctggcca acatggggca actgtccacg gattcagcag                          40

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aattcgagtt cctagatttt g                                              21

<210> SEQ ID NO 28
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 28
aattcaaaat ctaggaactc g                                                    21

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aattcgagta cctagattat gatttcctgc cagaaactga gcctccgc                       48

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggccgcggag gctcagtttc tggcaggaaa tcataatcta ggtactcg                       48

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aattcgagtt cctagattat gatttcctgc cagaaactga gcctccgc                       48

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggccgcggag gctcagtttc tggcaggaaa tcataatcta ggaactcg                       48

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aattcgagtt cctagatttc gatttcctgc cagaaactga gcctccgc                       48

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 34

```
ggccgcggag gctcagtttc tggcaggaaa tcgaaatcta ggaactcg                    48
```

<210> SEQ ID NO 35
<211> LENGTH: 942
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 35

```
atgcctctgc aactcctcct gttgctgatc ctactgggcc ctggcaacag cttgcagctg      60
tgggacacct gggcagatga agccgagaaa gccttgggtc ccctgcttgc ccggaccgg      120
agacaggcca ccgaatatga gtacctagat tatgatttcc tgccagaaac ggagcctcca     180
gaaatgctga ggaacagcac tgacaccact cctctgactg gcctggaac ccctgagtct      240
accactgtgg agcctgctgc gcggccgcac acatgcccac cgtgcccagc acctgaagcc    300
ctggggcac cgtcagtctt cctcttcccc ccaaaaccca aggacaccct catgatctcc     360
cggacccctg aggtcacatg cgtggtggtg gacgtgagcc acgaagaccc tgaggtcaag    420
ttcaactggt acgtggacgg cgtggaggtg cataatgcca agacaaagcc gcgggaggag    480
cagtacaaca gcacgtaccg tgtggtcagc gtcctcaccg tcctgcacca ggactggctg    540
aatggcaagg agtacaagtg caaggtctcc aacaaagccc tcccagtccc catcgagaaa    600
accatctcca aagccaaagg gcagccccga gaaccacagg tgtacaccct gcccccatcc   660
cgggaggaga tgaccaagaa ccaggtcagc ctgacctgcc tggtcaaagg cttctatccc   720
agcgacatcg ccgtggagtg ggagagcaat gggcagccgg agaacaacta caagaccacg   780
cctcccgtgc tggactccga cggctccttc ttcctctata gcaagctcac cgtggacaag   840
agcaggtggc agcaggggaa cgtcttctca tgctccgtga tgcatgaggc tctgcacaac   900
cactacacgc agaagagcct ctccctgtcc ccgggtaaat ga                      942
```

<210> SEQ ID NO 36
<211> LENGTH: 313
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 36

```
Met Pro Leu Gln Leu Leu Leu Leu Ile Leu Leu Gly Pro Gly Asn
  1               5                  10                  15

Ser Leu Gln Leu Trp Asp Thr Trp Ala Asp Glu Ala Glu Lys Ala Leu
             20                  25                  30

Gly Pro Leu Leu Ala Arg Asp Arg Arg Gln Ala Thr Glu Tyr Glu Tyr
         35                  40                  45

Leu Asp Tyr Asp Phe Leu Pro Glu Thr Glu Pro Glu Met Leu Arg
     50                  55                  60

Asn Ser Thr Asp Thr Thr Pro Leu Thr Gly Pro Gly Thr Pro Glu Ser
 65                  70                  75                  80

Thr Thr Val Glu Pro Ala Ala Arg Pro His Thr Cys Pro Pro Cys Pro
                 85                  90                  95

Ala Pro Glu Ala Leu Gly Ala Pro Ser Val Phe Leu Phe Pro Pro Lys
                100                 105                 110
```

```
Pro Lys Asp Thr Leu Met Ile Ser Arg Thr Pro Glu Val Thr Cys Val
        115                 120                 125
Val Val Asp Val Ser His Glu Asp Pro Glu Val Lys Phe Asn Trp Tyr
130                 135                 140
Val Asp Gly Val Glu Val His Asn Ala Lys Thr Lys Pro Arg Glu Glu
145                 150                 155                 160
Gln Tyr Asn Ser Thr Tyr Arg Val Val Ser Val Leu Thr Val Leu His
            165                 170                 175
Gln Asp Trp Leu Asn Gly Lys Glu Tyr Lys Cys Lys Val Ser Asn Lys
        180                 185                 190
Ala Leu Pro Val Pro Ile Glu Lys Thr Ile Ser Lys Ala Lys Gly Gln
    195                 200                 205
Pro Arg Glu Pro Gln Val Tyr Thr Leu Pro Pro Ser Arg Glu Glu Met
210                 215                 220
Thr Lys Asn Gln Val Ser Leu Thr Cys Leu Val Lys Gly Phe Tyr Pro
225                 230                 235                 240
Ser Asp Ile Ala Val Glu Trp Glu Ser Asn Gly Gln Pro Glu Asn Asn
            245                 250                 255
Tyr Lys Thr Thr Pro Pro Val Leu Asp Ser Asp Gly Ser Phe Phe Leu
        260                 265                 270
Tyr Ser Lys Leu Thr Val Asp Lys Ser Arg Trp Gln Gln Gly Asn Val
    275                 280                 285
Phe Ser Cys Ser Val Met His Glu Ala Leu His Asn His Tyr Thr Gln
290                 295                 300
Lys Ser Leu Ser Leu Ser Pro Gly Lys
305                 310

<210> SEQ ID NO 37
<211> LENGTH: 810
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 37
atgcctctgc aactcctcct gttgctgatc ctactgggcc ctggcaacag cttgcagctg      60
tgggacacct gggcagatga agccgagaaa gccttgggtc ccctgcttgc ccgggaccgg     120
agacaggcca ccgaatatga gtacctagat tatgatttcc tgccagaaac ggagcctcca     180
gaaatgctga ggaacagcac tgacaccact cctctgactg gcctggaac ccctgagtct      240 accactgtgg agcctgctgc gcggccgctg tgtgccaacc tagtaccggt gcccatcacc     300
aacgccaccc tggaccagat cactggcaag tggttttata tcgcatcggc ctttcgaaac     360
gaggagtaca ataagtcggt tcaggagatc caagcaacct tcttttactt caccccaac     420 aagacagagg acacgatctt tctcagagag taccagaccc gacaggacca gtgcatctat     480
aacaccacct acctgaatgt ccagcgggaa aatgggacca tctccagata cgtgggaggc     540
caagagcatt tcgctcactt gctgatcctc agggacacca gacctacat gcttgctttt     600 gacgtgaacg atgagaagaa ctggggggctg tctgtctatg ctgacaagcc agagacgacc     660
aaggagcaac tggagagtt ctacgaagct ctcgactgct tgcgcattcc caagtcagat     720
gtcgtgtaca ccgattggaa aaaggataag tgtgagccac tggagaagca gcacgagaag     780
gagaggaaac aggaggaggg ggaatcctag                                      810

<210> SEQ ID NO 38
```

-continued

<211> LENGTH: 269
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 38

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Pro Leu Cys Ala Asn Leu Val Pro
                85                  90                  95

Val Pro Ile Thr Asn Ala Thr Leu Asp Gln Ile Thr Gly Lys Trp Phe
            100                 105                 110

Tyr Ile Ala Ser Ala Phe Arg Asn Glu Glu Tyr Asn Lys Ser Val Gln
        115                 120                 125

Glu Ile Gln Ala Thr Phe Phe Tyr Phe Thr Pro Asn Lys Thr Glu Asp
    130                 135                 140

Thr Ile Phe Leu Arg Glu Tyr Gln Thr Arg Gln Asp Gln Cys Ile Tyr
145                 150                 155                 160

Asn Thr Thr Tyr Leu Asn Val Gln Arg Glu Asn Gly Thr Ile Ser Arg
                165                 170                 175

Tyr Val Gly Gly Gln Glu His Phe Ala His Leu Leu Ile Leu Arg Asp
            180                 185                 190

Thr Lys Thr Tyr Met Leu Ala Phe Asp Val Asn Asp Glu Lys Asn Trp
        195                 200                 205

Gly Leu Ser Val Tyr Ala Asp Lys Pro Glu Thr Thr Lys Glu Gln Leu
    210                 215                 220

Gly Glu Phe Tyr Glu Ala Leu Asp Cys Leu Arg Ile Pro Lys Ser Asp
225                 230                 235                 240

Val Val Tyr Thr Asp Trp Lys Lys Asp Lys Cys Glu Pro Leu Glu Lys
                245                 250                 255

Gln His Glu Lys Glu Arg Lys Gln Glu Glu Gly Glu Ser
            260                 265

<210> SEQ ID NO 39
<211> LENGTH: 1314
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 39
atggtggccg ggacccgctg tcttctagcg ttgctgcttc cccaggtcct cctgggcggc     60
gcggctggcc tcgttccgga gctgggccga aggaagttcg cggcggcgtc gtcgggccgc    120
ccctcatccc agccctctga cgaggtcctg agcgagttcg agttgcggct gctcagcatg    180
ttcggcctga acagagacc cacccccagc agggacgccg tggtgccccc ctacatgcta    240
gacctgtatc gcaggcactc aggtcagccg ggctcacccg ccccagacca ccggttggag    300

-continued

```
aggcagcca gccgagccaa cactgtgcgc agcttccacc atgaagaatc tttggaagaa      360
ctaccagaaa cgagtgggaa acaacccgg agattcttct ttaatttaag ttctatcccc       420
acggaggagt ttatcacctc agcagagctt caggttttcc gagaacagat gcaagatgct      480
ttaggaaaca atagcagttt ccatcaccga attaatattt atgaaatcat aaaacctgca      540
acagccaact cgaaattccc cgtgaccaga cttttggaca ccaggttggt gaatcagaat      600
gcaagcaggt gggaaagttt tgatgtcacc cccgctgtga tgcggtggac tgcacaggga      660
cacgccaacc atggattcgt ggtggaagtg gcccacttgg aggagaaaca aggtgtctcc      720
aagagacatg ttaggataag caggtctttg caccaagatg aacacagctg gtcacagata      780
aggccattgc tagtaacttt tggccatgat ggaaaagggc atcctctcca caaaagagaa      840
aaacgtcagg ccaccgaata tgagtaccta gattatgatt tcctgccaga aacggagcct      900
ccagaaatgc tgaggaacag cactgacacc actcctctga ctgggcctgg aacccctgag      960
tctaccactg tggagcctgc tgcaaggcgg aaacgcctta agtccagctg taagagacac     1020
cctttgtacg tggacttcag tgacgtgggg tggaatgact ggattgtggc tcccccgggg     1080
tatcacgcct tttactgcca cggagaatgc ccttttcctc tggctgatca tctgaactcc     1140
actaatcatg ccattgttca gacgttggtc aactctgtta actctaagat tcctaaggca     1200
tgctgtgtcc cgacagaact cagtgctatc tcgatgctgt accttgacga gaatgaaaag     1260
gttgtattaa agaactatca ggacatggtt gtggagggtt gtgggtgtcg ctag           1314
```

<210> SEQ ID NO 40
<211> LENGTH: 437
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 40

```
Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
```

```
                  180                 185                 190
Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
        210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Thr Glu Tyr Glu
        275                 280                 285

Tyr Leu Asp Tyr Asp Phe Leu Pro Glu Thr Glu Pro Pro Glu Met Leu
    290                 295                 300

Arg Asn Ser Thr Asp Thr Thr Pro Leu Thr Gly Pro Gly Thr Pro Glu
305                 310                 315                 320

Ser Thr Thr Val Glu Pro Ala Ala Arg Arg Lys Arg Leu Lys Ser Ser
                325                 330                 335

Cys Lys Arg His Pro Leu Tyr Val Asp Phe Ser Asp Val Gly Trp Asn
            340                 345                 350

Asp Trp Ile Val Ala Pro Pro Gly Tyr His Ala Phe Tyr Cys His Gly
        355                 360                 365

Glu Cys Pro Phe Pro Leu Ala Asp His Leu Asn Ser Thr Asn His Ala
    370                 375                 380

Ile Val Gln Thr Leu Val Asn Ser Val Asn Ser Lys Ile Pro Lys Ala
385                 390                 395                 400

Cys Cys Val Pro Thr Glu Leu Ser Ala Ile Ser Met Leu Tyr Leu Asp
                405                 410                 415

Glu Asn Glu Lys Val Val Leu Lys Asn Tyr Gln Asp Met Val Val Glu
            420                 425                 430

Gly Cys Gly Cys Arg
        435

<210> SEQ ID NO 41
<211> LENGTH: 795
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 41
atgcctctgc aactcctcct gttgctgatc ctactgggcc ctggcaacag cttgcagctg      60
tgggacacct gggcagatga agccgagaaa gccttgggtc ccctgcttgc ccggaccgg      120 agacaggcca ccgaatatga gtacctagat tatgatttcc tgccagaaac ggagcctcca     180
gaaatgctga ggaacagcac tgacaccact cctctgactg gcctggaac ccctgagtct      240 accactgtgg agcctgctgc gcggccgcca cctggcccc ctcgagtttc cccagaccct      300
cgggccgagc tggacagcac cgtgctcctg acccgctctc tcctggcgga cacgcggcag     360
ctggctgcac agctgaggga caaattccca gctgacgggg accacaacct ggattccctg     420 cccacctgg ccatgagtgc gggggcactg gagctctac agctcccagg tgtgctgaca       480
aggctgcgag cggaccctact gtcctacctg cggcacgtgc agtggctgcg ccgggcaggt    540
ggctcttccc tgaagaccct ggagccgag ctgggcaccc tgcaggcccg actggaccgg     600
```

```
ctgctgcgcc ggctgcagct cctgatgtcc cgcctggccc tgccccagcc accccggac    660 ccgccggcgc cccgctggc gccccctcc tcagcctggg ggggcatcag ggccgccac      720 gccatcctgg ggggctgca cctgacactt gactgggccg tgagggact gctgctgctg    780 aagactcggc tgtga                                                    795
```

<210> SEQ ID NO 42
<211> LENGTH: 264
<212> TYPE: PRT
<213> ORGANISM: Artificial Sequence
<220> FEATURE:
<223> OTHER INFORMATION: Description of Artificial Sequence: Synthetic
   fusion protein

<400> SEQUENCE: 42

```
Met Pro Leu Gln Leu Leu Leu Leu Ile Leu Leu Gly Pro Gly Asn
 1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Pro Pro Gly Pro Pro Arg Val
                85                  90                  95

Ser Pro Asp Pro Arg Ala Glu Leu Asp Ser Thr Val Leu Leu Thr Arg
            100                 105                 110

Ser Leu Leu Ala Asp Thr Arg Gln Leu Ala Ala Gln Leu Arg Asp Lys
        115                 120                 125

Phe Pro Ala Asp Gly Asp His Asn Leu Asp Ser Leu Pro Thr Leu Ala
    130                 135                 140

Met Ser Ala Gly Ala Leu Gly Ala Leu Gln Leu Pro Gly Val Leu Thr
145                 150                 155                 160

Arg Leu Arg Ala Asp Leu Leu Ser Tyr Leu Arg His Val Gln Trp Leu
                165                 170                 175

Arg Arg Ala Gly Gly Ser Ser Leu Lys Thr Leu Glu Pro Glu Leu Gly
            180                 185                 190

Thr Leu Gln Ala Arg Leu Asp Arg Leu Leu Arg Arg Leu Gln Leu Leu
        195                 200                 205

Met Ser Arg Leu Ala Leu Pro Gln Pro Pro Asp Pro Pro Ala Pro
    210                 215                 220

Pro Leu Ala Pro Pro Ser Ser Ala Trp Gly Gly Ile Arg Ala Ala His
225                 230                 235                 240

Ala Ile Leu Gly Gly Leu His Leu Thr Leu Asp Trp Ala Val Arg Gly
                245                 250                 255

Leu Leu Leu Leu Lys Thr Arg Leu
            260
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
   peptide

<400> SEQUENCE: 43

Gln Ala Thr Glu Tyr Glu Tyr Leu Asp Tyr Asp Phe Leu Pro Glu Cys
1               5                   10                  15

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Tyr Leu Asp Tyr Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Phe Leu Asp Tyr Ser
1               5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Asp Arg Arg
1

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid consensus sequence
<220> FEATURE:
<221> NAME/KEY: MOD_RES
<222> LOCATION: (2)
<223> OTHER INFORMATION: Thr or Met
<220> FEATURE:
<221> NAME/KEY: MOD_RES
<222> LOCATION: (8)
<223> OTHER INFORMATION: Pro, Ala, Gln, Glu, or Arg
<220> FEATURE:
<221> NAME/KEY: MOD_RES
<222> LOCATION: (9)
<223> OTHER INFORMATION: Pro or Leu
<220> FEATURE:
<221> NAME/KEY: MOD_RES
<222> LOCATION: (10)
<223> OTHER INFORMATION: Ala or Thr

<400> SEQUENCE: 47

Ala Xaa Glu Ala Gln Thr Thr Xaa Xaa Xaa
1               5                   10

<210> SEQ ID NO 48
<211> LENGTH: 31

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ala Thr Glu Tyr Glu Tyr Leu Asp Tyr Asp Phe Leu Pro Glu Thr
 1               5                  10                  15

Glu Pro Pro Glu Met Leu Arg Asn Ser Thr Asp Thr Thr Pro Thr
                20                  25                  30
```